US006743967B2

(12) United States Patent
Hadlaczky et al.

(10) Patent No.: US 6,743,967 B2
(45) Date of Patent: Jun. 1, 2004

(54) ARTIFICIAL CHROMOSOMES, USES THEREOF AND METHODS FOR PREPARING ARTIFICIAL CHROMOSOMES

(75) Inventors: Gyula Hadlaczky, Szamos (HU); Aladar A. Szalay, Highland, CA (US)

(73) Assignees: Chromos Molecular Systems Inc. (CA); The Biological Research Center of the Hungarian Academy of Sciences (HU)

( * ) Notice: Subject to any disclaimer, the term of this patent is extended or adjusted under 35 U.S.C. 154(b) by 0 days.

(21) Appl. No.: 09/096,648

(22) Filed: Jun. 12, 1998

(65) Prior Publication Data

US 2001/0008025 A1 Jul. 12, 2001

Related U.S. Application Data

(63) Continuation of application No. 08/629,822, filed on Apr. 10, 1996, now abandoned.

(51) Int. Cl.⁷ .......................... C12N 15/00; C12N 5/00; C12N 5/02; C12N 15/63; C12N 15/85
(52) U.S. Cl. .................. 800/25; 800/21; 435/325; 435/455
(58) Field of Search .................. 800/21, 25, 13, 800/18, 22, 3, 4; 435/455, 325, 463, 320.1

(56) References Cited

U.S. PATENT DOCUMENTS

| | | | |
|---|---|---|---|
| 4,441,972 A | 4/1984 | Pohl | 204/180 |
| 4,476,004 A | 10/1984 | Pohl | 204/299 |
| 4,518,584 A | 5/1985 | Mark et al. | 424/85 |
| 4,608,339 A | 8/1986 | Yoakum et al. | 435/172.2 |
| 4,684,611 A | 8/1987 | Schilperoort et al. | 435/172.3 |
| 4,686,186 A | 8/1987 | Sugden | 435/243 |
| 4,736,866 A | 4/1988 | Leder et al. | 800/1 |
| 4,784,737 A | 11/1988 | Ray et al. | 204/180.1 |
| 4,801,540 A | 1/1989 | Hiatt et al. | 435/172.3 |
| 4,806,476 A | 2/1989 | Coons et al. | 435/172.2 |
| 4,873,191 A | 10/1989 | Wagner et al. | 435/172.3 |
| 4,873,316 A | 10/1989 | Meade et al. | 530/412 |
| 4,906,576 A | 3/1990 | Marshall, III | 435/287 |
| 4,923,814 A | 5/1990 | Marshall, III | 435/173 |
| 4,935,350 A | 6/1990 | Patel et al. | 435/69.4 |
| 4,946,952 A | 8/1990 | Kiefer | 536/27 |
| 4,955,378 A | 9/1990 | Grasso | 128/421 |
| 4,970,162 A | 11/1990 | Aksamit | 435/240.26 |
| 4,997,764 A | 3/1991 | Dalla Favera | 435/240.27 |
| 5,019,034 A | 5/1991 | Weaver et al. | 604/20 |
| 5,021,344 A | 6/1991 | Armau et al. | 435/172.3 |

(List continued on next page.)

FOREIGN PATENT DOCUMENTS

| | | |
|---|---|---|
| EP | 0208491 A2 | 1/1987 |
| EP | 0240373 | 10/1987 |
| EP | 0247494 A2 | 12/1987 |
| EP | 0254315 B1 | 1/1988 |
| EP | 0254315 A3 | 1/1988 |
| EP | 0254315 A2 | 1/1988 |
| EP | 0264166 A1 | 4/1988 |
| EP | 0279582 A2 | 8/1988 |
| EP | 0350052 | 1/1990 |
| EP | 0375406 A2 | 6/1990 |
| EP | 0375406 | 6/1990 |
| EP | 0473253 | 3/1992 |
| EP | 0532050 A2 | 9/1992 |
| EP | 0838526 | 4/1998 |
| WO | 8204443 | 12/1982 |
| WO | 8800239 | 1/1988 |
| WO | 8801648 | 3/1988 |
| WO | 8909219 | 10/1989 |
| WO | 9100358 | 1/1991 |
| WO | 9105044 | 4/1991 |
| WO | 9207080 | 4/1992 |
| WO | 9214819 | 9/1992 |
| WO | 9217582 | 10/1992 |
| WO | 9325567 | 12/1993 |
| WO | 9419456 | 9/1994 |
| WO | 9423049 | 10/1994 |
| WO | 9424300 | 10/1994 |
| WO | 9500178 | 1/1995 |
| WO | 9507643 | 3/1995 | ............ A47C/7/20 |
| WO | 9514769 | 6/1995 |
| WO | 9520044 | 7/1995 |
| WO | 9522297 | 11/1995 |
| WO | 9529992 | 11/1995 |
| WO | 9532297 | 11/1995 |
| WO | 9640965 | 12/1996 |
| WO | 9707668 | 3/1997 |
| WO | 9707669 | 3/1997 |
| WO | 9716533 | 5/1997 |
| WO | 9740183 | 10/1997 |
| WO | 9808964 | 3/1998 |
| WO | 9813505 | 4/1998 | ............ C12N/15/82 |

OTHER PUBLICATIONS

Fehilly et al. Nature, vol. 307, Feb. 16, 1984.*
Wall, Theriogenology, vol. 45, pp. 57–68, 1996.*
Jiewen et al., Theriogenology, vol. 45, No. 1, p. 336, Jan. 1, 1996.*

(List continued on next page.)

*Primary Examiner*—Deborah Crouch
*Assistant Examiner*—Thái-An N. Ton
(74) *Attorney, Agent, or Firm*—Stephanie L. Seidman; Fish & Richardson P.C.

(57) ABSTRACT

Methods for preparing cell lines that contain artificial chromosomes, methods for preparation of artificial chromosomes, methods for purification of artificial chromosomes, methods for targeted insertion of heterologous DNA into artificial chromosomes, and methods for delivery of the chromosomes to selected cells and tissues are provided. Also provided are cell lines for use in the methods, and cell lines and chromosomes produced by the methods. In particular, satellite artificial chromosomes that, except for inserted heterologous DNA, are substantially composed of heteroaromatic are provided. Methods for use of the artificial chromosomes, including for gene therapy, production of gene products and production of transgenic plants and animals are also provided.

20 Claims, 5 Drawing Sheets

U.S. PATENT DOCUMENTS

| | | | |
|---|---|---|---|
| 5,063,162 A | 11/1991 | Kiefer | 435/270 |
| 5,081,018 A | 1/1992 | Grummt et al. | 435/69.1 |
| 5,118,620 A | 6/1992 | Armau et al. | 435/172.3 |
| 5,144,019 A | 9/1992 | Rossi et al. | 536/27 |
| 5,149,796 A | 9/1992 | Rossi et al. | 536/27 |
| 5,162,215 A | 11/1992 | Bosselman et al. | 435/172.3 |
| 5,215,914 A | 6/1993 | Lo et al. | 435/253.1 |
| 5,223,263 A | 6/1993 | Hostetler et al. | 424/450 |
| 5,240,840 A | 8/1993 | Feinberg et al. | 435/172.3 |
| 5,240,846 A | 8/1993 | Collins et al. | 435/240.1 |
| 5,260,191 A | 11/1993 | Yang | 435/6 |
| 5,266,600 A | 11/1993 | Tenmyo et al. | 514/691 |
| 5,272,262 A | 12/1993 | Rossi et al. | 536/23.2 |
| 5,288,625 A | 2/1994 | Hadlaczky | 435/172.2 |
| 5,292,658 A | 3/1994 | Cormier et al. | 435/252.33 |
| 5,298,429 A | 3/1994 | Evans et al. | 436/501 |
| 5,300,431 A | 4/1994 | Pierce et al. | 435/172.3 |
| 5,324,655 A | 6/1994 | Kriegler et al. | 435/240.2 |
| 5,354,674 A | 10/1994 | Hodgson | 435/172.3 |
| 5,358,866 A | 10/1994 | Mullen et al. | 435/240.2 |
| 5,364,761 A | 11/1994 | Ariga | 435/6 |
| 5,387,742 A | 2/1995 | Cordell | 800/2 |
| 5,396,767 A | 3/1995 | Suzuki | 60/298 |
| 5,409,810 A | 4/1995 | Larder et al. | 435/5 |
| 5,413,914 A | 5/1995 | Franzusoff | 435/23 |
| 5,418,155 A | 5/1995 | Cormier et al. | 435/189 |
| 5,424,409 A | 6/1995 | Ely et al. | 536/23.71 |
| 5,434,086 A | 7/1995 | Collins et al. | 436/125 |
| 5,434,340 A | 7/1995 | Krimpenfort et al. | 800/2 |
| 5,436,392 A | 7/1995 | Thomas et al. | 800/205 |
| 5,449,604 A | 9/1995 | Schellenberg et al. | 435/6 |
| 5,453,357 A | 9/1995 | Hogan | 435/7.21 |
| 5,457,182 A | 10/1995 | Wiederrecht et al. | 530/402 |
| 5,461,032 A | 10/1995 | Krapcho et al. | 514/12 |
| 5,468,615 A | 11/1995 | Chio et al. | 435/7.2 |
| 5,468,634 A | 11/1995 | Liu | 435/240.2 |
| 5,470,708 A | 11/1995 | Yang et al. | 435/6 |
| 5,470,730 A | 11/1995 | Greenberg et al. | 435/172.3 |
| 5,482,928 A | 1/1996 | De Bolle et al. | 514/12 |
| 5,489,520 A | 2/1996 | Adams et al. | 435/172.3 |
| 5,491,075 A | 2/1996 | Desnick et al. | 435/69.7 |
| 5,491,283 A | 2/1996 | Groffen et al. | 800/2 |
| 5,496,731 A | 3/1996 | Xu et al. | 435/320.1 |
| 5,501,662 A | 3/1996 | Hofmann | 604/20 |
| 5,501,967 A | 3/1996 | Offringa et al. | 435/172.3 |
| 5,503,999 A | 4/1996 | Jilka et al. | 435/172.3 |
| 5,543,319 A | 8/1996 | Fournier et al. | 415/354 |
| 5,712,134 A | 1/1998 | Hadlaczky | 435/172.2 |
| 5,721,118 A | 2/1998 | Scheffler | 435/69.1 |
| 5,721,367 A | 2/1998 | Kay et al. | 800/2 |
| 5,891,691 A | 4/1999 | Hadlaczky | 435/172.3 |
| 6,025,155 A | 2/2000 | Hadlackzky et al. | 435/69.1 |
| 6,077,697 A | 6/2000 | Hadlackzky et al. | 435/172.3 |
| 6,133,503 A | * 10/2000 | Scheffler | 800/21 |

OTHER PUBLICATIONS

Moreadith et al., Journal of Molecular Medicine, vol. 75, pp. 208–216, 1997.*

Seamark, Reprod. Fertil. Dev., vol. 6, pp. 653–657, 1994.*

Mullins et al., Journal of Clinical Investigation, vol. 98, No. 11, pp. S37–S40, 1996.*

Albertsen et al., "Construction and characterization of a yeast artificial chromosome library containing seven haploid human genome equivalents", *PNAS, 87*:4256–42–60 (2000).

Berlani et al., "Genomic organization of two families of highly repeated nuclear DNA sequences of maize selected for autonomous replicating activity in yeast", *Plant Molecular Biol., 11*:161–172 (1988).

Berlani et al., "Sequence analysis of three fragments of maize nuclear DNA which replicate autonomously in yeast", *Plant Molecular Biol., 11*:173–182 (1988).

Blackburn et al., Book:*Telomeres*, Chapter 13, "Plant Telomeres", Cold Spring Harbor Laboratory Press, pp. 371–387 (1995).

Brown et al., "Artificial chromosomes: ideal vectors?", *TIBTECH, 18*:218–223 (2000).

Dausset et al., "The CEPH YAC Library", *Behring Inst. Mitt., 91*:13–20 (1992).

Dixon et al., "Engineering Chimeras for Noah's Ark", *Hastings Cent. Rep.,14(2)*:10–12 (1984).

Dresser, B.L., "Indian Desert Cat Birth Makes History", *Cat News:Issue 11 #19*, pp. 1–3 (1989).

Eckdahl et al., "DNA structures associated with autonomously replicating sequences form plant", *Plant molecular Biol., 12*:507–516 (1989).

Frary et al., "Molecular mapping of the centromeres of tomato chromosomes 7 and 9", *Mol. Gen. Genet., 250*:295–304 (1996).

Giraldo et al., "Size matters: use of YACs, BACs and PACs in transgenic animals", *Transgenic Res., 10*:83–103 (2001).

Hadlaczky et al., "DNA Synthesis And Division In Interkingdom Heterokaryons", *In Vitro, 16(8)*:647–650 (1980).

Houben et al.,"Immunostaining and interphase arrangement of field bean kinetochores", *Chrom. Res., 3*:27–31 (1995).

Jacobovits et al., "Germ–line transmission and expression of a human–derived yeast artificial chromosome", *Nature, 362*:255–258 (1993).

Jiang et al., "A conserved repetitive DNA element located in the centromeres of cereal chromosomes", *Proc. Natl. Acad. Sci. U.S.A., 93*:14210–14213 (1996).

Kaszas et al., "Misdivision analysis of centromere structure in maize", *EMBO J., 15(19)*:5246–5255 (1996).

Kraemer et al., "Intra– and Interspecific Embryo Transfer", *J. Experimental Zoology, 228*:363–371 (1983).

Lanza et al., "Cloning Noah's Ark", *Scientific American*, Nov.:84–89 (2000).

Larin et al., "A method for linking yeast artificial chromosomes", *Nucl. Acid. Res., 24*:4192–4196 (1996).

Libert et al., "Construction of a Bovine Genomic Library of Large Yeast Artificial Chromosome Clones", *Genomics, 18*:270–276 (1993).

Loi et al., "Genetic rescue of an endangered mammal by cross–species nuclear transfer using post–mortem somatic cells", *Nat. Biotechnol., 19*:962–964 (2001).

Marshall et al., "Transfer of YACs up to 2.3 Mb intact into human cells with polyethylenimine", *Gene Therapy, 6*:1634–1637 (1999).

Mole–Bajer et al., "Autoantibodies from a patient with scleroderma CREST recognized kinetochores of the higher plant *Haemanthus*", *Proc. Natl. Acad. Sci. U.S.A., 87*:3599–3603 (1990).

Moore et al., "Centromeric sites and cereal chromosome evolution", *Chromosoma, 105*:321–323 (1997).

Palmieri et al., "Construction of a pilot human YAC library in a recombination–defective yeast strain", *Gene, 188*:169–174 (1997).

Pope et al., "In vitro fertilization in domestic and non–domestic cats including sequences of early nuclear events, development in vitro, cryopreservation and successful intra– and interspecies embryo transfer," *J. Reprod. Fert. Suppl. 47*: 189–201 (1993).

Press Release Advanced Cell Jan. 12, 2001 "Advanced Cell Technology Announces Birth of First Cloned Endangered".

Press Release Advanced Cell Apr. 8, 2003 Collaborative Effort Yields Endangered Species Clone.

Rhodes et al., "Telomere structure and function", *Curr. Opin. Struc. Biol.*, 5:311–322 (1995).

Rorie et al., "A simplified procedure for making reconstituted blastocysts for interspecific and intergeneric transfer", *Vet. Rec.*, 135:186–187 (1994).

Rossant and Frels, "Interspecific Chimeras in Mammals: Sucdessful Production of Live Chimeras Betwen *Mus musculus* and *Mus caroli*", *Science*, 208:419–421 (1980).

Schedl et al., "A method for the generation of YAC transgenic mice by pronuclear microinjection", *Nuc. Acid. Res.*, 21:4783–4787 (1993).

Shen et al., "A structurally defined mini–chromosome vector for the mouse germ line", *Current Biology*, 10:31–34 (2000).

Summers et al., "Interspecific Chimerism–The Characterization And Immunological Responsiveness of *Bos Taurus–Bos Indicus* Haemopoietic Chimeras Produced By Embroyo Transfer", *Aust. J. Exp. Med. Sci.*, 62 (*Pt1*): 27–45 (1984).

Takeda et al., "Construction of a bovine yeast artificial chromosome (YAC) library", *Animal Genetics*, 29:216–219 (1998).

Toye et al., "A yeast artificial chromosome (YAC) library containing 10 haploid chicken genome equivalents", *Mammalian Genome*, 8:274–276 (1997).

Wada et al., "Chimeric YACs were generated at unreduced rates in conditions that suppress coligation", *NAR*, 22:1651–1654 (1994).

Woods et al., "A Mule Cloned from Fetal Cells by Nuclear Transfer", *Scienceexpress published on line*, May 2003.

Voet, D. and Voet, J., Book: *Biochemistry*, Chapter 33, "Eukaryotic Gene Expression", John Wiley & Sons, New York, p. 1033 (1990).

Zhong et al., "Zebrafish Genomic Library in Yeast Artificial Chromosomes", *Genomics*, 48:136–138 (1998).

Zakian, "Telomeres: Beginning to Understand the End", *Science*, 270:1601–1607 (1995).

Brinster et al., Factors affecting the efficiency of introducing foreign DNA into mice by microinjecting eggs, *Proc. Natl. Acad. Sci. USA* 82:4438–4442 (1985).

Bühler et al., Rabbit β–Casein Promoter Directs Secretion of Human Interleukin–2 into the Milk of Transgenic Rabbits, *Bio/Technology* 8:140–143 (1990).

Drohan, Transgenic Animals: "Great and Small," *Journal of Cellular Biochemistry* 49:111–112 (1992).

Ebert et al., Transgenic Production of a Variant of Human Tissue–type Plasminogen Activator in Goat Milk: Generation of Transgenic Goats and Analysis of Expression, *Bio/Technology* 9:835–838 (1991).

Gordon et al., Genetic transformation of mouse embryos by microinjection of purified DNA, *Proc. Natl. Acad. Sci. USA* 77(12):7380–7384 (1980).

Gordon et al., Production of Human Tissue Plasminogen Activator in Transgenic Mouse Milk, *Bio/Technology* 5:1183–1187 (1987).

Haskell et al., Efficient Production of Transgenic Cattle by Retroviral Infection of Early Embryos, *Molecular Reproduction and Development* 40:386–390 (1995).

Hill et al., Production of Transgenic Cattle by Pronuclear Injection, *Theriogenology* 37:222 (1992).

Houdebine, Production of pharmaceutical proteins from transgenic animals, *Journal of Biotechnology* 34:269–287 (1994).

Krimpenfort et al., Generation of transgenic dairy cattle using 'in vitro 'embryo production, *Bio/Technology* 9:844–847 (1991).

Maeda et al., Production of human α–interferon in silkworm using a baculovirus vector *Nature* 315:592–594 (1985).

Palmiter et al., Dramatic growth of mice that develop from eggs microinjected with metallothionein–growth hormone fusion genes, *Nature* 300:611–615 (1982).

Rancourt et al., Wolffish Antifreeze Protein from Transgenic *Drosophila*, *Bio/Technology* 8:453–457 (1990).

Riego et al., Production of Transgenic Mice and Rabbits that Carry and Express the Human Tissue Plasminogen Activator cDNA under the Control of a Bovine Alpha S1 Casein Promoter, *Theriogenology* 39:1173–1185 (1993).

Simons et al., Alteration of the quality of milk by expression of sheep β–lactoglobulin in transgenic mice, *Nature* 328:530–532 (1987).

Simons et al., Gene Transfer into Sheep, *Bio/Technology* 6:179–183 (1988).

Velander et al., High–level expression of a heterologous protein in the milk of transgenic swine using the cDNA encoding human protein C, *Proc. Natl. Acad. Sci. USA* 89:12003–12007 (1992).

Wall et al., High–level synthesis of a heterologous milk protein in the mammary glands of transgenic swine, *Proc. Natl. Acad. Sci. USA* 88:1696–1700 (1991).

Wall et al., Making Transgenic Livestock: Genetic Engineering on a Large Scale, *Journal of Cellular Biochemistry* 49:113–120 (1992).

Wright et al., High level expression of active human alpha–1–antitrypsin in the milk of transgenic sheep, *Bio/Technology* 9:830–834 (1991).

Vos, JM, The simplicity of complex MACs, *Nature Biotechnology* 15:1257–1259 (1997).

Crystal, Transfer of Genes to Humans: Early Lessons and Obstacles to Success, *Science* 270:404–410 (1995).

Cuthbert et al., Construction and characterization of a highly stable human:rodent monochromosomal hybrid panel for genetic complementation and genome mapping studies, *Cytogenet Cell Genet* 71:68–76 (1995).

Garside et al., A method for karyotyping mouse blastocyst embryos developing from in vivo and in vitro fertilized eggs, *Experientia* 41:1183–1184 (1985).

Higgins et al., Organization of a repetitive human 1.8 kb Kpnl sequence localized in the heterochromatin of chromosome 15, *Chromosoma* 93:77–86 (1985).

IJdo et al., Improved telomere detection using a telomere repeat probe $(TTAGGG)_n$ generated by PCR, *Nucleic Acids Research* 19(17):4780 (1991).

Kalitsis et al., A Chromosome 13–Specific Human Satellite I DNA Subfamily with Minor Presence on Chromosome 21: Further Studies on Robertsonian Translocations, *Genomics* 16:104–112 (1993).

Klinger et al., Modulation of the Activity of an Avian Gene Transferred into a Mammalian Cell by Cell Fusion, *Proc. Natl. Acad. Sci.* 71(4):1398–1402 (1974).

Larin et al., *De novo* formation of several features of a centromere following introduction of a Y alphoid YAC into mammalian cells, *Human Molecular Genetics* 3(5):689–695 (1994).

Ledbetter et al., New Somatic Cell Hybrids for Physical Mapping in Distal Xq and the Fragile X Region, *Americal Journal of Medical Genetics* 38:418–420 (1991).

Meyne et al., Chromosome localization and orientation of the simple sequence repeat of human satellite I DNA, *Chromosoma* 103:99–103 (1994).

Rasko et al., Pattern of segregation of chicken HPRT phenotype in Chinese hamster–chick red blood cell hybrids, *Crytogenet Cell Genet* 24:129–137 (1979).

Roberts et al., Ribosomal RNA Gene Amplification: A Selective Advantage in Tissue Culture, *Cancer Genet Cytogenet* 29:119–127 (1987).

Sakai et al., Human Ribosomal RNA Gene Cluster: Identification of the Proximal End Containing a Novel Tandem Repeat Sequence, *Genomics* 26:521–526 (1995).

Takeda et al., Expression of SV40–*lacZ* Gene in Mouse Preimplantation Embryos After Pronuclear Microinjection, *Molecular Reproduction and Development* 30:90–94 (1991).

Thoraval et al., A methylated human 9–kb repetitive sequence on acrocentric chromosomes is homologous to a subtelomeric repeat in chimpanzees, *Proc. Natl. Acad. Sci.* 93:4442–4447 (1996).

Vissel et al., A satellite III sequence shared by human chromosomes 13, 14, and 21 that is contiguous with α satellite DNA, *Cytogenet Cell Genet* 61:81–86 (1992).

Waye et al., Human β satellite DNA: Genomic organization and sequence definition of a class of highly repetitive tandem DNA, *Proc. Natl. Acad. Sci.* 86:6250–6254 (1989).

Worton et al., Human Ribosomal RNA Genes: Orientation of the Tandem Array and Conservation of the 5' End, *Science* 239:64–68 (1988).

Cram et al., "XVII congress of the International Society for Analytical Cytology, Tutorial IV", *Chromosome Analysis and Sorting with Commercial Flow Cytometers* (1994).

Dickson et al., Human ribosomal DNA: conserved sequence elements in a 4.3–kb region downstream from the transcription unit, *Gene* 84:197–200 (1989).

Featherstone and Huxley, Extrachromosomal maintenance and amplification of yeast artificial chromosomes, *Genomics* 17:267–278 (1993).

Financsek et al., Human ribosomal RNA gene: Nucleotide sequence of the transcription initiation region and comparison of three mammalian genes, *Proc. Natl. Acad. Sci.* 79:3092–3096 (1982).

Gonzales and Schmickel, The human 18S ribosomal RNA gene: Evolution and stability, *Am. J. Hum. Genet.* 38:419–427 (1986).

Gonzalez et al., Variation among human 28S ribosomal RNA genes, *Proc. Natl. Acad. Sci.* 82:7666–7670 (1985).

Gray et al., Chromosome measurement and sorting by flow systems, *Proc. Nat. Acad. Sci.* 72:1231–1234 (1975).

Hernandez et al., Conserved features in the mode of replication of eukaryotic ribosomal RNA genes, *EMBO J.* 12(4):1475–1485 (1993).

Hogan, et al., *Manipulating the Mouse Embryo: A Laboratory Manual*, Cold Spring Harbor Laboratory Press, Cold Spring Harbor, NY, pp. 253–289 see, especially pp. 255–264 and Appendix 3, (1994).

Ioannou, et al., A new bacteriophage P1–derived vector for the propagation of large human DNA fragments, *Nature Genetics*, 6:84–89 (1994).

Lebo et al., Design and operation of a dual laser chromosome sorter, *Cytometry* 3:213–219 (1982).

Li et al., Decondensation of hamster chromosomes in the nuclei of 1–cell stage mice embryo following chromosome microinjection, *Theriogenology*, 45(1):336 (1996).

McCallum and Maden, Human 18S ribosomal RNA sequence inferred from DNA sequence, *Biochem. J.* 232:725–733 (1985).

Mendelsohn, et al., Separation of isolated chinese hamster metaphase chromosomes into three size–groups, *J. Mol. Biol.*, 32:101–112 (1968).

Nazar et al., Sequence homologies in mammalian 5.8S ribosomal RNA, *Biochem.* 15(3):505–508 (1976).

Safrany and Hidvegi, New tandem repeat region in the non–transcribed spacer of human ribosomal RNA gene, *Nucl. Acids Resh.* 17(8):3013–3023 (1989).

Stubblefield and Pershouse, Direct formation of microcells from mitotic cells for use in chromosome transfer, *Somatic Cell & Molec. Genet.* 18:485–491 (1992).

Telenius et al., Chromatid contamination can impair the purity of flow–sorted metaphase chromosomes, *Cytometry* 14:97–101 (1993).

Albrecht, et al., "Cationic lipid mediated transfer of c–abl and bcr antisense oligonucleotides to immature normal myeloid cells: Uptake, biological effects and modulation of gene expression*", *Ann Hematol* 72:73–79 (1996).

Baker et al., Suppression of human colorectal carcinoma cell growth by wild–type p53, *Science* 249:912–915 (1990).

Barnett et al., Telomere directed fragmentation of mammalian chromosomes, *Nucleic Acids Res.* 21 (1): 27–36 (1993).

Bartholdi, et al., Chromosome sorting by flow cytometry, *Meth. Enzy.*, 151:253–267, 1987.

Beck von Bodman, et al., "Expression of multiple eukaryotic cells from a single promoter," in *Nicotina, Bio/Technology* 13:587–591, (1995).

Biggin et al., Buffer gradient gels and $^{35}S$ label as an aid to rapid DNA sequence determination, *Proc. Natl. Acad. Sci. USA*, 80:3963–3965 (1983).

Blackburn et al. The molecular structure of centromeres and telomeres, *Ann. Rev. Biochem.*, 53:163–194 (1984).

Blattner et al., Charon phages: Safer derivatives of bacteriophage lambda for DNA cloning, *Science* 196:16 (1977).

Blennow, et al., Swedish survey on extra structurally abnormal chromosomes in 39 105 consecutive prenatal diagnoses: Prevalence and characterization by fluorescence in situ hybridization, *Prenatal Diagnosis*, 14:1019–1028, 1994.

Blumenthal, et al., Rapid isolation of metaphase chromosome containing high molecular weight DNA, *J. Cell Biol.*, 81:255–259, 1979.

Bostock and Clark, Satellite DNA in large marker chromosomes of methotrexate–resistant mouse cells, *Cell* 19:709–715 (1980).

Bostock and Christie, Analysis of the frequency of sister chromatid exchange in different regions of chromosomes of the Kangaroo rat (*Dipodomys ordii*), *Chromosoma* 56:275–287 (1976).

Bower, Constructing a fully defined human minichromosome: Cloning a centromere, *Proc. 4th Eur. Congress Biotechnol.* 3:571 (1987).

Brazolot, et al., "Efficient transfection of chicken cells by lipofection and introduction of transfected blastoderm cells into the embryo", *Mol. Repro. Dev.* 30:304–312, (1993).

Brewer and Fangman, The localization of replication origins on ARS plasmids in *S. cerevisiae*, *Cell* 51:463–471 (1987).

Brisson and Hohn, [27] Plant virus vectors: Cauliflower mosaic vectors, *Methods for Plant Molecular Biology*, Weissbach et al., eds., Academic Press, N.Y., Section VIII, pp. 437–446 (1988).

Brondum–Nielsen and Mikkelsen, A 10–year survey, 1980–1990, of prenatally diagnosed small supernumerary marker chromosomes, indentified by fish analysis. Outcome and follow–up of 14 cases diagnosed in a series of 12 699 prenatal samples, *Prenatal Diagnosis, 15*:615–619, 1995.

Brown, Mammalian artificial chromosomes, *Curr. Opin. Genes Dev. 2*:479–486 (1992).

Brown et al., Mammalian artificial chromosomes, *Curr. Opin. Genet. Devt. 6(3)*: 281–288 (1996).

Bullock and Botchan, Molecular events in the excision of SV40 DNA from the chromosomes of cultured mammalian cells. In: *Gene Amplification.*, Schimke RT, ed. Cold Spring Harbor, NY: Cold Spring Harbor Laboratory Press, pp 215–224 (1982).

Burhans and Huberman, DNA replication origins in animal cells—a question of context? *Science 263*:639–640 (1994).

Burhans et al., Identification of an origin of bidirectional DNA replication in mammalian chromosomes, *Cell 62*:955–965 (1990).

Burke et al., Cloning of large segments of exogenous DNA into yeast by means of artificial chromosome vectors, *Science, 236*:806–812 (1987).

Burki, et al., Zonal fractionation of mammalian metaphase chromosomes and determination of their DNA content, *Prep. Bioch., 3(2)*:157–182 (1973).

Carine et al., Chinese hamster cells with a minichromosome containing centromere region of human chromosome 1, *Somatic Cell Molec. Genet. 12*:479–491 (1986).

Carine et al., Molecular characterization of human minichromosomes with centromere from chromosome 1 in hamster–human hybrids, *Somatic Cell Molec. Genet. 15(5)*:445–460 (1989).

Carrano, et al., Measurement and purification of human chromosomes by flow cytometry and sorting, *Proc. Natl. Acad. Sci. USA, 76(3)*:1382–1384, 1979.

Carrano and Wolff, Distribution of sister chromatid exchanges in the euchromatin and heterochromatin of the Indian muntjac, *Chromosoma 53*: 361–369 (1975).

Carsience, et al., "Germline chimeric chickens from dispersed donor blastodermal cells and compromised recipient embryos", *Develop 117*:669–675, (1993).

Chalfie et al., Green fluorescent protein as a marker for gene expression, *Science 263*:802–804 (1994).

Chang et al., Ribozyme–mediated site–specific cleavage of the HIV–1 genome, *Clin. Biotech. 2*:23–31 (1990).

Chen et al., High–efficiency transformation of mammalian cells by plasmid DNA, *Mol. Cell. Biol. 7*:2745–2752 (1987).

Chen et al., Genetic mechanism of tumor suppression by the human p53 gene, *Science 250*:1576 (1990).

Chick, et al., "Beta cell culture on synthetic capillaries: an artificial endocrine pancreas", Elliot P. Joslin Research Laboratory, Harvard Medical School, p. 847–849, (1975).

Chikashige et al., Composite motifs and repeat symmetry in *S. pombe* centromeres: Direct analysis by integration of NotI restriction sites, *Cell 57*:739–751 (1989).

Chisari et al., A transgenic mouse model of the chronic hepatitis B surface antigen carrier state, *Science 230*: 1157–1160 (1985).

Church, Replication of chromatin in mouse mammary epithelial cells grown in vitro, *Genetics 52*: 843–849 (1965).

Clarke et al., The structure and function of yeast centromeres, *Ann. Rev. Genet. 19*:29–56. (1985).

Coffman, et al., In Vitro replication of plasmids containing human ribsomal gene sequences: Origin localization and dependence on an aprotinin–binding cytosolic protein, *Exp. Cell Resh., 209*:123–132, 1993.

Colbère–Garapin et al., A new dominant hybrid selective marker for higher eukaryotic cells, *J. Mol. Biol. 150*:1–14 (1981).

Collard, et al., Separation and analysis of human chromosomes by combined velocity sedimentation and flow sorting applying single– and dual–laser flow cytometry, *Cytometry, 5*:9–19, 1984.

Collins and Newlon, Chromosomal DNA replication initiates at the same origins in meiosis and mitosis, *Mol Cell Biol 14*:3524–3534. (1994).

Cooke, Non–programmed and engineered chromosome breakage, *Cold Spring Harbor Monograph Series 29*:219–245 (1995).

Cooke et al., pYAC–4 Neo, a yeast artificial chromosome vector which codes for G418 resistance in mammalian cells, *Nuc Acids Res.* 16(24):11817 (1988).

Cooper and Tyler–Smith, The putative centromere–forming sequences of λCM8 is a single copy sequence and is not a component of most human centromeres, *Hum. Mol. Gen. 1(9)*:753–754 (1992).

Couto et al., Inhibition of intracellular *histoplasma capsulatum* replication by murine macrophages that produce human defensin, *Infect. Immun. 62*:2375–2378 (1994).

Cram et al., Polyamine buffer for bivariate human flow cytogenetic analysis and sorting, *Methods in Cell Biology 33*:377–382 (1990).

Cram, et al., Univariate analysis of metaphase chomosomes using the hypotonic potassium chloride–propidium iodide protocol, *Meth. Cell Biol., 33*:369–376, 1990.

Cross et al., The structure of subterminal repeated sequence present on many human chromosomes, *Nucleic Acids Res. 18(22)*: 6649–6657 (1990).

Current state of the art, *Chromos Molecular Systems—News Release* (May 29, 1996) (available at http://www.chromos.com/contents.html).

Cutler, Electroporation: Being developed to transform crops, *Ag Biotechnology News 7*:3 (Sep./Oct. 1990).

Database WPI Derwent Abstract 199442, citing WO 9424300, Transposition construct for introducing genes into eukaryotic cell genome.

Davidson et al., Improved techniques for the induction of mammalian cell hybridisation by polyethylene glycol, *Somatic Cell. Genet. 2*:165–176 (1976).

Dean et al. Multiple mutations in highly conserved residues are found in mildly affected cystic fibrosis patients, *Cell 61*:863–870 (1990).

deJong et al., Mammalian artificial chromosome pilot production facility: large–scale isolation of functional satellite DNA–based artificial chromosomes, *Cytometry* 35:129–133 (1999).

DePamphilis, Eukaryotic DNA replication: Anatomy of an origin, *Annu. Rev. Biochem. 62*:29–63 (1993).

Dhar, et al., "Transfer of Chinese Hamster Chromosome 1 to Mouse Cells and Regional Assignment of 7 Genes: A Combination of Gene Transfer and Microcell Fusion", *Somatic Cell and Molecular Genetics, 10*:(6)547–559, (1984).

DIALOG Abstract 007389041, citing: EP 0254 315.

DIALOG Abstract 007268905, citing: EP 0240 373 A1.

Dieken, et al., "Efficient modification of human chromosomal allesles using recombination–proficient chicken/human microcell hybrids", *Nature Genet. 12*:174–182, (1996).

Dunckley et al., Retroviral–mediated transfer of a dystrophin minigene into *mdx* mouse myoblasts in vitro, *FEBS Lett. 296*:128–34 (1992).

Eissenberg and Elgin, Boundary functions in the control of gene expression, *Trends in Genet., 7*(10):335–340, 1991.

Erlich et al., Recent advances in the polymerase chain reaction, *Science 252*:1643–1651 (1991).

Etches, et al., "Chimeric chickens and their use in manipulation of the chicken genome", *Poultry Sci. 72*:882–889, (1993).

Fangman and Brewer, A question of time: replication origins of eukaryotic chromosomes, *Cell 71*: 363–366 (1992).

Farr et al., Generation of a human X–derived minichromosome using telomere–associated chromosome fragmentation, *EMBO J. 14*:5444–5454 (1995).

Farr, Mammalian telomeres and chromosome fragmentation, *Cell Devtl. Biol. 7*: 41–48 (1996).

Farrel et al., p53 is frequently mutated in Burkitt's lymphoma cell lines, *EMBO J. 10*:2879–2887 (1991).

Fátyol et al., Cloning and molecular characterization of a novel chromosome specific centromere sequence of Chinese hamster, *Nucl. Acids Res. 22*:3728–3736 (1994).

Fechheimer et al., Transfection of mammalian cells with plasmid DNA by scrape loading and sonication loading, *Proc. Natl. Acad. Sci. USA 84*:8463–8467 (1987).

Ford and Fried, Large inverted duplications are associated with gene amplification, *Cell 45*:425–430, (1986).

Fournier, A general high–efficiency procedure for production of microcell hybrids, *Proc. Natl. Acad. Sci,USA 78*:6349–6353 (1981).

Fowler, et al., "Donor lymphoid cells of th2 cytokine phenotype reduce lethal graft versus host disease and facilitats fully allogenetic cell transfers in sublethally irradiated mice", *Advances in Bone Marrow Purging and Processing: Fourth International Symposium*, p. 533–540, (1994).

Frasier, et al., "Efficient incorporation of transfected blastodermal cells into chimeric chicken embryos", *Int. J. Dev. Biol. 37*:381–385, (1993).

French et al., Construction of a retroviral vector incorporating mouse VL30 retrotransposon–derived, transcriptional regulatory sequences, *Anal. Biochem. 228*:354–355 (1995).

Frohman and Martin, Cut, paste, and save: new Approaches to altering specific genes in mice, *Cell 56*:145–147 (1989).

Fromm et al., Expression of genes transferred into monocot and dicot plant cells by electroporation, *Proc. Natl. Acad. Sci.USA 82*:5824–5828 (1985).

Fu S et al., Molecular cytogenetic study of an extra small chromosome, (CHINA) 1992, 19(4):294–7, MEDLINE Abstract: 93103732.

Gaub, et al., "The chicken ovalbumin promoter is under negative control which is relieved by steriod hormones", *The EMBO Journal, 6*:(8)2313–2320, (1987).

Gillespie et al., Tissue–specific expression of human CD4 in transgenic mice, *Mol. Cell. Biol. 13*:2952–2958 (1993).

Gluzman, SV40–transformed simian cells support the replication of early SV40 mutants, *Cell 23*:175–182 (1981).

Gogel, et al., Mapping of replication initiation sites in the mouse ribosomal gene cluster, *Chromosoma, 104*:511–518, 1996.

Gonzalez and Sylvester, Complete sequence of the 43–kb human ribosomal DNA repeat: Analysis of the intergenic space, *Genomics, 27*:320–328, 1985.

Goodfellow et al., Techniques for mammalian genome transfer, in *Genome Analysis a Practical Approach*, K.E. Davies, ed., IRL Press, Oxford, Washington DC. pp. 1–17 (1989).

Gout, et al., Prolactin–stimulated growth of cell cultures established from malignant Nb rat lymphomas, *Cancer Res., 40*:2433–2436, 1980.

Graham, and van der Eb, A new technique for the assay of infectivity of human adenovirus 5 DNA, *Virology 52*:456–457 (1973).

Gravholt and Friedrich, Molecular cytogenetic study of supernumerary marker chromosomes in an unselected group of children, *Am. J. Med. Gen., 56*:106–111, 1995.

Green et al., Systematic screening of yeast artificial–chromosome libraries by use of the polymerase chain reaction, *Proc. Natl. Acad. Sci USA 87*:1213–1217 (1990).

Green, et al., "Chromosomal region of the cystic fibrosis gene in yeast artificial chromosomes: A model for human genome mapping", *Science 250*:94–98, (1990).

Grierson et al. *Plant Molecular Biology*, 2d Ed., Blackie, London, Ch. 7–9 (1988).

Gritz et al., Plasmid–encoded hygromycin B resistance: the sequence of hygromycin B phosphotransferase gene and its expression in *Escherichia coli* and *Saccharomyces cerevisiae, Gene 25*:179–188 (1983).

Guide to Techniques in Mouse Development, *Methods in Enzymology 25*:803–932 (1993).

Gunning et al., A human β–actin expression vector system directs high–level accumulation of antisense transcripts, *Proc. Natl. Acad. Sci.USA 84*:4831–4835 (1987).

Haaf et al., Integration of Human α–satellite DNA into simian chromosomes: centromere protein binding and disruption of normal chromosome segregation, *Cell, 70*:681–696 (1992).

Haas and Dowding, Aminoglycoside–modifying enzymes, *Meth. Enzymol., 43*:611–628, 1975.

Haase et al., Transcription inhibits the replication of autonomously replicating plasmids in human cells, *Mol. Cell. Biol. 14*:2516–2524 (1994).

Hadlaczky and Szalay, Mammalian artificial chromosomes: Potential vectors for gene therapy, Abstract from International Symposium on *Gene Therapy of Cancer, AIDS and Genetic Disorders*, Trieste (Italy) (Apr. 10–13, 1996) (available at http://www.chromos.com/contents. html).

Hadlaczky et al., Centromere formation in mouse cells cotransformed with human DNA and a dominant marker gene, *Proc. Natl. Acad. Sci.USA 88*:8106–8110 (1991).

Hadlaczky, Structure of metaphase chromosomes of plants, *Internatl. Rev. Cytol. 94*:57–76 (1985).

Hadlaczky et al., Direct evidence for the non–random localization of mammalian chromosomes in the interphase nucleus, *Exp. Cell Res. 167*:1–15 (1986).

Hadlaczky and Szalay, Mammalian artificial chromosomes: Introduction of novel genes into mammalian artificial chromosomes, Abstract from International Symposium on *Gene Therapy of Cancer, AIDS and Genetic Disorders*, Trieste (Italy) (Apr. 10–13, 1996) (available at http://www.chromos.com/contents.html).

Hadlaczky et al., Protein depleted chromosomes, *Chromosoma 81*:537–555 (1981).

Hadlaczky et al., Structure of isolated protein–depleted chromosomes of plants. *Chromosoma 86*:643–659 (1982).

Hadlaczky et al., Centromere proteins, *Chromosoma* 97:282–288 (1989).

Hall et al., Expression and regulation of *Escherichia coli* lacZ gene fusions in mammalian cells, *J. Mol. Appl. Gen* 2:101–109 (1983).

Handeli et al., Mapping replication units in animal cells, *Cell* 57 909–920 (1989).

Hanna et al., Specific expression of the human CD4 gene in mature $CD4^+$ $CD8^-$ and immature $CD4^+$ $CD8^+$ T cells and in macrophages of transgenic mice, *Mol. Cell. Biol.* 14:1084–1094 (1994).

Harper et al., Localization of single copy DNA sequences on G–banded human chromosomes by in situ hybridization, *Chromosoma* 83:431–439 (1981).

Harrington, et al., Formation of *de novo* centromeres and construction of first–generation human artificial microchromosomes, *Nature Genetics*, 15:345–355, 1997.

Hassan et al., Replication and transcription sites are colocalized in human cells. *J. Cell. Sci.* 107:425–434 (1994).

Heller et al., Mini–chromosomes derived from the human Y chromosome by telomere directed chromosome breakage, *Proc. Natl. Acad. Sci. USA* 93:7125–7130 (1996).

Henikoff et al., Position–effect variegation after 60 years, *Trends in Genetics 6*: 422–426 (1990).

Hilwig and Gropp, Decondensation of constitutive heterochromatin in L cell chromosomes by a benzimidazole compound ("33258 Hoechst"), *Exp Cell Res* 81: 474–477 (1973).

Hogan et al., *Manipulating the Mouse Embryo: A Laboratory Manual*, Cold Spring Harbor Laboratory Press, Cold Spring Harbor, NY, pp. 253–289, see, especially pp. 255–264 and Appendix 3 (1994).

Hollo et al., Evidence for a megareplicon covering megabases of centrome segments, *Chromosome Research* 4:1–14 (1996) (available at http://www.chromos.com/contents.html).

Holmen, et al., "Efficient Lipid–mediated transfection of DNA into Primary Rat Hepatocytes", *In Vitro Cell, Dev. Biol.* 30:347–351, (1995).

Holmquist and Comings, Sister chromatid exchange and chromosome organisation based on a bromodeoxyuridine Giemsa–C–banding technique (TC–banding), *Chromosoma* 52:245–259 (1975).

Hsu and Markvong, Chromosomes and DNA in *Mus*: Terminal DNA synthetic sequences in three species, *Chromosoma* 51:311–322 (1975).

Huberman et al., The in vivo replication origin of the yeast 2 μm plasmid. *Cell 51*:473–481 (1987).

Huberman and Riggs, On the mechanism of DNA replication in mammalian chromosomes, *J Mol Biol* 32:327–341 (1968).

Huxley, Mammalian artificial chromosomes: a new tool for gene therapy, *Gene Therapy, 1*:7–12 (1994).

Hyde et al., Correction of the ion transport defect in cystic fibrosis transgenic mice by gene therapy, *Nature 362*: 250–255 (1993).

Hyrien et al., The multicopy appearance of large inverted duplication and the sequence at the inversion joint suggest a new model for gene amplification, *EMBO J 7*:407–417 (1988).

Ikeno et al., Construction of YAC–based mammalian artificial chromosomes, *Nature Biotech* 16:431–439 (1998).

Ioannou, et al., A new bacteriophage P1–derived vector for the propogation of large human DNA fragments, *Nature Genetics, 6*:84–89, 1994.

Ish–Horowitz et al., Rapid and efficient cosmid cloning, *Nucleic Acids Res. 9*:2989–2998 (1981).

Jabs, et al., "Characterization of a cloned DNA sequence that is present at centromeres of all human autosomes and the X chromosome and shows polymorphic variation", *Proc. Natl. Acad.* 81:4884–4888, (1984).

Jacob et al., On the regulation of DNA replication in bacteria, *Cold Spring Harb Symp Quant Biol* 28:329–348 (1963).

Johnson, et al., Genetic mapping of variable length of rDNA segments to centromeric regions of mouse Chromosomes 11, 12, 15, 16, and 18, *Mammalian Genome, 4*:49–52, 1993.

Johnston et al., Construction of a mammalian artificial chromosome, Abstract from CGAT grant application, Sep. 1994.

Joy and Gopinathan, Expression of microinjected foreign DNA in the silkworm, *Bombex mori, Current Science* 66:145–150 (1991).

Kappel et al., Regulating gene expression in transgenic animals, *Current Biology*, p. 548–553 (1992).

Keown et al., Methods for introducing DNA into mammalian cells, *Meth. Enzymol.* 185:527–537 (1990).

Kerem et al., Identification of the cystic fibrosis gene: genetic analysis, *Science 245*:1073–1080 (1989).

Kereso et al., De novo chromosome formations by large–scale amplification of the centromeric region of mouse chromosomes, *Chromosome Research* 4:1–14 (1996) (available at http://www.chromos.com/contents.html).

Killary, et al., "Microcell Fusion", *Methods in Enzymology*, 254:133–152, (1995).

Kitsberg et al., Replication structure of the human b–globin gene domain, *Nature* 366:588–590 (1993).

Klotman et al. Transgenic models of HIV–1, *Current Sci Ltd. 9*:313–324, (1995).

Korenberg et al., Human genome organization: Alu, LINES, and the molecular structure of metaphase chromosome bands, *Cell* 53:391–400 (1988).

Kornberg and Baker, *DNA Replication.* 2nd. ed., New York: W.H. Freeman and Co, p. 474 (1992).

Lalande, et al., Molecular detection and differntiation of deletions in band 13q14 in human retinoblastoma, *Cancer Genet Cytogenet, 23*:151–157, 1986.

Lamb, B. et al., YAC transgenics and the study of genetics and human disease, *Curr. Opinion: Genetics & Dev. 6*, 342–348 (1995).

Lambert et al., Functional complementation of ataxia–telangiectasia group D (AT–D) cells by microcell–mediated chromosome transfer and mapping of the AT–D locus to the region 11q22–23, *Proc. Natl. Acad. Sci. USA* 88:5907–59 (1991).

Larsson et al. Reduced β2–microglobulin mRNA levels in transgenic mice expressing a designed hammerhead ribozyme, *Nucleic Acids Research* 22:2242–2248, (1994).

Lawrence et al. Sensitive, high–resolution chromatin and chromosome mapping in situ: Presence and orientation of two closely integrated copies of EBV in a lymphoma line, *Cell* 52:51–61 (1988).

Le Bolc'h, et al., "Cationic phosphonolipids as non viral vectors for DNA transfection", *Tetrahedron Lett.* 36:6681–6684, (1995).

Leder et al., EK2 derivatives of bacteriophage lambda useful in the cloning of DNA from higher organisms: The λgtWES system, *Science* 196:175–177 (1977).

Lee et al., Human gamma X satellite DNA: an X chromosome specific centromeric DNA sequence, *Chromosoma* 104: 103–112 (1995).

Lin et al., Isolation and identification of a novel tandemly repeated DNA sequence in the centromeric region of human chromosome 8, *Chromosoma* 102: 333–339 (1993).

Little, et al., Intiation and termination of DNA replication in human rRNA genes, *Molec. and Cell. Biol.,* 13(10):6600–6613, 1993.

Liu et al., The pro region of human neutrophil defensin contains a motif that is essential for normal subcellular sorting, *Blood* 85:1095–1103 (1995).

Locardi et al., Persistent infection of normal mice with human immunodeficiency virus, *J. Virol.* 66:1649–1654 (1992).

Loefler, et al., "Gene Transfer into Primary and Established Mammalian Cell Lines wiht Lipopolyamine–Coated DNA", *Methods for Transforming Animal and Plant Cells* 217:599–618, (1993).

Looney et al., The dihydrofolate reductase amplicons in different methotrexate–resistant Chinese hamster cell lines share at least a 273–kilobase core sequence, but the amplicons in some cell lines are much larger and remarkably uniform in structure, *Mol. Cell Biol.* 8:5268–5279 (1988).

Lorenz et al. Isolation and expression of a cDNA encoding *Renilla reniformis* luciferase, *Proc. Natl. Acad. Sci. USA* 88:4438–4442 (1991).

Lorenz et al., Expression of the *Renilla reniformis* luciferase gene in mammalian cells, *J. Biolum. Chemilum.* 11:31–37 (1996).

Love, et al., "Transgenic birds by microinjection", *Bio/Technology* 12:60–63, (1994).

Ma et al., Organisation and genesis of dihydrofolate reductase amplicons in the genome of a methotrexate–resistant Chinese hamster ovary cell line, *Mol. Cell Biol.* 8:2316–2327 (1988).

Ma et al., Sister chromatid fusion initiates amplification of the dihydrofolate reductase gene in Chinese hamster cells, *Genes Develop.* 7:605–620 (1993).

Madan et al., Fluorescence analysis of late DNA replication in mouse metaphase chromosomes using BUdR and 33258 Hoechst, *Exp. Cell Res.* 99:438–444 (1976).

Maden, et al., Clones of human ribosomal DNA containing the complete 18 S–rRNA and 28 S–rRNA genes, *J. Biochem.,* 246:519–527, 1987.

Maniatis et al., The isolation of structural genes from libraries of eucaryotic DNA, *Cell* 15:687–701 (1978).

Mansour et al., Disruption of the proto–oncogene *int*–2 in mouse embryo–derived stem cells: a general strategy for targeting mutations to non–selectable genes, *Nature* 336:348–352 (1988).

Manuelidis, Heterochromatic features of an 11–megabase transgene in brain cells, *Proc. Natl. Acad. Sci. USA,* 88:1049–1053, 1991.

Matthews et al., Purification and properties of *Renilla reniformis* luciferase, *Biochemistry* 16:85–91 (1977).

Maxwell et al., Regulated expression of a diphtheria toxin A–chain gene transfected into human cells: possible strategy for inducing cancer cell suicide, *Cancer Res.* 46:4660–4664 (1986).

McCormick et al., Construction of human chromosomes 21–specific yeast artificial chromosomes, *Proc. Natl. Acad. Sci. USA* 86:9991–9995 (1989).

McGill et al., λCM8, a human sequence with putative centromeric function, does not map to the centromere but is present in one or two copies at 9qter, *Hum. Mol. Gen.* 1(9):749–751.

McGuigan et al., Replication of yeast DNA and novel chromosome formation in mouse cells, *Nuclic Acids Res.* 24(12): 2271–2280 (1996).

McLean, "Improved techniques for immortalizing animal cells", *TIBTECH* 11:232–238, (1993).

Meinkoth and Wahl, Hybridization of nucleic acids immobilized on solid supports, *Anal. Biochem.* 138:267–284 (1984).

Meyne et al., Distribution of non–telomeric sites of the $(TTAGGG)_n$ telomeric sequence in vertebrate chromosomes, *Chromosoma* 99:3–10, (1990).

Miesfeld and Arnheim, Indentification of the in vivo and in vitro origin of transcription in human rDNA, *Nucleic Acid Rsch.*, vol. 10, No. 13, 1982.

Miller and Rosman, Improved retroviral vectors for gene transfer and expression, *Biotechniques* 7:980–990 (1989).

Miller, Is the centromeric heterochromatin of *Mus musculus* late replicating? *Chromosoma* 55:165–170 (1976).

Miller et al., High–efficiency ligation and recombination of DNA fragments by vertebrate cells, *Science* 220:606–609.

Miller, in *Experiments in Molecular Genetics*, Cold Spring Harbor Press, pp. 352–355 (1972).

Mitani et al., Delivering therapeutic genes—matching approach and application, *Trends Biotech.* 11:162–166 (1993).

Morgan and French Anderson, Human gene therapy, *Annu. Rev. Biochem.* 62:191–217 (1993).

Morgenstern et al., Advanced mammalian gene transfer: High titre retroviral vectors with multiple drug selection markers and a complementary helper–free packaging cell line, *Nucleic Acids Res.* 18:3587–3596 (1990).

Mulligan, The basic science of gene therapy, *Science* 260:926–932 (1993).

Murray et al., Construction of artificial chromosomes in yeast, *Nature* 305:189–193 (1983).

Nabel et al., Site–specific gene expression in vivo by direct gene transfer into the arterial wall, *Science* 249:1285–1288 (1990).

Naider, et al., Reversible alkylation of a methionyl residue near the active site of B–Galactosidase, *Biochemistry,* 11(17):3202–3210, 1972.

Nikolaev et al., Microinjection of recombinant DNA into early embryos of the mulberry silkworm *Bombyx mori*, *Mol. Biol. (Moscow)* 23:1177–87 (1989).

O'Keefe et al., Dynamic organization of DNA replication in mammalian cell nuclei: Spatially and temporally defined replication of chromosome–specific a–satellite DNA sequences, *J. Cell Biol.* 116:1095–1110 (1992).

Ohnuki, Structure of chromosomes, *Chromosoma* (Berl), 25:402–428, 1968.

Osborne et al., A mutation in the second nucleotide binding fold of the cystic fibrosis gene, *Am. J. Hum. Genetics* 48:608–612 (1991).

Park, et al., "Modulation of Transcriptional Activity of the Chicken ovalbumin gene promoter in primary cultures of chicken oviduct cells: effect of putative regulatory elements in the 5'–flanking region", *Biochem and Mol Biol International 36*:(4)811–816, (1995).

Paszowski and Saul, [28]. Direct gene transfer to plants, *Methods for Plant Molecular Biology*, Weissbach et al., eds., Academic Press, N.Y., Section VIII, pp. 447–463 (1988).

Perry and Wolff, A new Giemsa method for the differential staining of sister chromatids, *Nature 251*:156–158 (1974).

Petitte, et al., "Production of somatic and germline chimeras in the chicken by transfer of early blastodermal cells", *Development 108*:185–189, (1990).

Pierce and Sternberg, Using Bacteriophage P1 system to clone high molecular weight genomic DNA, *Meth. Enzymol., 216*:549–574, 1992.

Pierce, et al., A positive selection vector for cloning high molecular weight DNA by the bacteriophage P1 system: Improved cloning efficacy, *Proc. Natl. Acad. Sci. USA, 89*:2056–2060, 1992.

Pinkel et al., Cytogenic analysis using quantitative, high–sensitivity, fluorescence hybridization, *Proc. Natl. Acad. Sci. USA, 83*:2934–2938 (1986).

Pluta et al., Structure of the human centromere at metaphase, *TIBS 15*:181–185 (1990).

Prasher et al., Primary structure of the *Aequorea victoria* green–fluorescent protein, *Gene 111*:229–233 (1992).

Praznovszky et al., De novo chromosome formation in rodent cells, *Proc. Natl. Acad. Sci. USA 88*:11042–11046 (1991).

Priest, Cytogenetics. In *Medical Technology Series*. R.M. French, M. Eichman, B. Fiorella, and H.F. Weisberg, eds. (Lea and Febiger, Philadelphia) pp. 189–190 (1969).

Quastler et al., Cell population kinetics in the intestinal epithelium of the mouse, *Exp. Cell Res. 17*:420–438 (1959).

Raimondi, et al., "X–ray mediated size reduction, molecular characterization and transfer in model systems of a human artificial minichromosome", Abstract from International Symposium on *Gene Therapy of Cancer, AIDS and Genetic Disorders*, Trieste (Italy) Apr. 10–13, 1996.

Raimondi, Gene targeting to the centromeric DNA of a human minichromosome. *Hum. Gene Ther. 7*:1103–1109 (1996).

Raynal et al., Complete nucleotide sequence of mouse 18 S rRNA gene: comparison with other available homologs, *FEBS Lett. 167* (2): 263–367 (1984).

Raynal et al., Complete nucleotide sequence of mouse 18 SrRNA gene: comparison with other available homologs, *FEBS Lett. 167* (2): 263–367 (1984).

Remy, et al., "Gene Transfer with a Series of Lipophilic DNA–Binding Molecules", *Bioconjugate Chem. 5*:647–654, (1994).

Report and recommendations of the panel to assess the NIH investment in research on gene therapy, Orkin and Motulsky, co–chairs (Dec. 7, 1995) (available at http://www.nih.gov/news/panelrep.html).

Richie and Lo, Introduction of human DNA into mouse eggs by injection of dissected chromosome fragments, *Science 245*:175–177 (1989).

Riordan et al., Identification of the cystic fibrosis gene: cloning and characterization of complementary DNA, *Science 245*:1066–1072 (1989).

Robertson et al., Germ–line transmission of genes introduced into cultured pluripotential cells by retroviral vector, *Nature 323*:445–448 (1986).

Rogers et al., [26] Gene transfer in plants: Production of transformed plants using Ti plasmid vectors, *Methods for Plant Molecular Biology*, Weissbach et al., eds., Academic Press, N.Y., Section VIII, pp. 423–436 (1988).

Rommens et al., Identification of the cystic fibrosis gene: chromosome walking and jumping, *Science 245*:1059–1065 (1989).

Rosenfeld et al., In vivo transfer of the human cystic fibrosis transmembrane conductance regulator gene to the airway epithelium, *Cell 68*:143–155 (1992).

Roslaniec, et al., Development of a high speed optical chromosome sorter based on photoinduced cross–linking of DNA with psoralens, International Society for Analytical Cytology Abstracts, 1994.

Roth, et al., "Artifizielle chromosomen", *Natur Wissenschaften 74*:78–85, (1987).

Roth et al., Illegitimate Recombination in Mammalian Cells, Chapter 21 621–653.

Rowe, et al., Genetic mapping of 18S ribosomal RNA–related loci to mouse chromosomes 5, 6, 9, 12, 17, 18, 19, and X, *Mammalian Genome, 7*:886–889, 1996.

Sambrook et al., *Molecular Cloning: A Laboratory Manual*, Vol. 1, 2d Ed., Cold Spring Harbor Laboratory Press,, Section 2.18 (1989).

Sanes et al., Use of a recombinant retrovirus to study post–implantation cell lineage in mouse embryos, *EMBO J. 5(12)*:3133–3142 (1986).

Sanford, et al., "General Protocol for Microcell–Mediated Chromosome Transfer", *Somatic Cell and Molecular Genetics, 13*:(3)279–284, (1987).

Sang, et al., "Transgenic chickens—methods and potential application", *TIBTECH 12*:415–420.

Sanger et al., Cloning in single–stranded bacteriophage as an aid to rapid DNA sequencing, *J. Mol. Biol. 143*:161–178 (1980).

Saxon et al., Selective transfer of individual human chromosomes to recipient cells, *Mol. Cell. Biol. 1*:140–146 (1985).

Schedl et al., A method for the generation of YAC transgenic mice by pronuclear microinjection, *Nuc. Acids Res. 21*:4783–4787 (1993).

Schneider et al., Procedure for production of hybrid genes and proteins and its use in assessing significance of amino acid differences in homologous tryptophan synthetase α polypeptides, *Proc. Natl. Acad. Sci, USA* 78(4):2169–2173.

Scientists report a major step in ralizing the commerical potential of engineered artificial chromosomes in significant life sciences sectors, including gene therapy, *Chromos Molecular Systems—News Release* (May 29, 1996) (available at http://www.chromos.com/contents.html).

Selig et al., Regulation of mouse satellite DNA replication time, *EMBO J. 7*:419–426 (1988).

Sher, et al., "Role of T–Cell derived cytokines in the downregulation of immune responses in parasitic and retroviral infection", *Immunolical Reviews* (127)183–204, (?).

Shizuya, et al., Cloning and stable maintenance of 300–kilobase–pair fragments of human DNA in *Escherichia coli* using an F–factor–based vector, *Proc. Natl. Acad. Sci. USA, 89*:8794–8797, 1992.

Shwarchuk, et al., Substructure in the radiation survival response at low dose: asynchronous and partially synchronized V79–WNRE cells, *Int. J. Radiat. Biol.,* 64(5):601–612, 1993.

Sillar and Young, A new method for the preparation of metaphase chromosomes for flow analysis, *J. Histo. Cytoch.,* 29:74–78, 1981.

Smith, et al., "Amplification of large artificial chromosomes", *Proc. Natl. Acad. Sci. USA,* 87:8242–8246, (1990).

Smith et al., Distinctive chromosomal structures are formed very early in the amplification of CAD genes in Syrian hamster cells, *Cell* 63:1219–1227 (1990).

Solus et al., Characterization of single–copy probe from vicinity of centromere of human chromosome 1, *Somatic Cell Mol. Genet.* 14:381–391 (1988).

Sternberg, Bacteriophage P1 cloning system for the isolation, amplification, and recovery of DNA fragments as large as 100 kilobase pairs, *Proc. Natl. Acad. Sci. USA* 87:103–107 (1990).

Stoehr, et al., A reliable preparation of mono–dispersed chromosome suspensions for flow cytometry, *Histochemistry,* 74:57–61, 1982.

Strauss, "Transfection of Mammalian Cells via Lipofection", *Meth Biol* 54:307–327, (1996).

Strojek et al. The use of transgenic animal techniques for livestock improvement, *Genetic Engineering: Principles and Methods* 10:221–246, (1988).

Stubblefield and Wray, Isolation of specific human metaphase chromosomes, *Bioch. and Biophys. Res. Commun.,* 83(4):1404–1414, 1978.

Sugden et al., A vector that replicates as a plasmid and can be efficiently selected in B–lymphoblast transformed by Epstein–Barr virus, *Mol. Cell. Biol.* 5:410–413 (1985).

Sumner, Scanning electron microscopy of mammalian chromosomes from prophase to telophase. *Chromosoma* 100:410–418 (1991).

Sumner, A simple technique for demonstrating centromeric heterochromatin, *Cell Res.* 75:304–306 (1972).

Sun et al., Human artificial episomal chromosomes for cloning large DNA fragments in human cells, *Nature Genetics* 8:33–41 (1994).

Szybalska, et al., "DNA–Mediated heritable transformation of biochemical trait", *Proc. N.A.S.* 48:2026–2034, (1962).

Szybalsky et al. Genetic studies with human cell lines, *Natl. Cancer Inst. Monogr.* 7:75–89 (1982).

Tamura et al., Microinjection of DNA into early embryo of Bombyx mori, *Bio Ind.* 8:26–31 (1991) (Chemical Abstracts # 114(21)200502z).

Taylor et al., Analysis of extrachromosomal structures containing human centromeric alphoid satellite DNA sequences in mouse cells, *Chromosoma* 105:70–81 (1996).

Teifel, et al., "New Lipid Mixture for Efficient Lipid–Mediated Transfection of BHK Cells", *Biotechniques* 19:79–82, (1995).

Toledo et al., Co–amplified markers alternate in megabase long chromosomal inverted repeats and cluster independently in interphase nuclei at early steps of mammalian gene amplification, *EMBO J.* 11:2665–2673 (1992).

Tomizuka et al., Functional expression and germline transmission of a human chromosome fragment in chimaeric mice, *Nature Genetics* 16:133–143 (1997).

Tonghua et al., Effects of antisense epidermal growth factor and its receptor retroviral expression vectors on cell growth of human pancreatic carcinoma cell line, *Chin. Med. J. (Beijing, Engl. Ed.)* 108:653–659 (1995).

Tora, et al., "Cell–specific activity of a GGTCA half–palindromic oestrogen–responsive element in the chicken ovalbumin gene promoter", *The EMBO Journal* 7:(12)3771–3778, (1988).

Torczynski et al., Cloning and sequencing of a human 18S ribosomal RNA gene, DNA 4 (4): 283–291 (1985).

Transfection of DNA into eukaryotic cells, *Current Protocols in Molecular Biology,* vol. 1, Wiley Inter–Science, Supplement 14, Unit 9.1.1–9.1.9 (1990).

Traver et al., Rapid screening of a human genomic lubrary in yeast artificial chromosomes for single–copy sequences, *Proc. Natl. Acad. Sci. USA* 86:5898–5902 (1989).

Tyler–Smith et al., Mammalian chromosome structure, *Curr. Opin. Genet. Devt. 3:* 390–397 (1993).

Uchimiya et al., Transgenic plants, *J. Biotechnol. 12:* 1–20 (1989).

Van den Engh, et al., Preparation and bivariate analysis of suspensions of human chromosomes, *Cytometry,* 6:92–100, 1985.

Van den Engh, et al., Improved resolution of flow cytometric measurements of Hoechst–and Chromomycin–A3–stained human chromosomes after addition of citrate and sulfite, *Cytometry,* 9:266–270, 1988.

Van den Engh, et al., Preparation of chromosomes suspensions for flow cytometry, *Cytometry,* 5:108–117, 1984.

Van Dilla, et al., Human chromosome–specific DNA libraries: Construction and availability, *Bio/Technology,* 4:537–552, 1986.

Vig and Richards, Formation of primary constriction and heterochromatin in mouse does not require minor satellite DNA, *Exp. Cell Res.* 201:292–298 (1992).

Wang and Fedoroff, Banding of human chromosomes treated with trypsin, *Nature* 235:52–54 (1972).

Waring, et al., "Nucleotide sequence repetition: A rapidly reassociating fraction of mouse DNA", *Science* 154:791–794, (1966).

Weber et al., Formation of genes coding for hybrid proteins by recombination between related, cloned genes in *E. coli, Nuc Acids Res,* 11(16):5661–5669 (1983).

Weinberg, Tumor suppressor genes, *Science* 254:1138–1146 (1991).

White et al., A frame–shift mutation in the cystic fibrosis gene, *Nature* 344:665–667 (1990).

Why are MACs in vogue, *Chromos Molecular Systems— News Release* (May 29, 1996) (available at http://www.chromos.com/contents.html).

Wigler et al., DNA–mediated transfer of the adenine phosphoribosyltransferase locus into mammalian cells, *Proc. Natl. Acad. Sci. USA* 76:1373–1376 (1979).

Willard, Chromosome manipulation: a systematic approach toward understanding human chromosome structure and function, *Proc. Natl. Acad. Sci. USA* 93:6847–6850 (1996).

Willard and Waye, Hierarchical order in chromosome specific human alpha satellite DNA, *Trends Genet. 3:*192–198 (1987).

Williams and Blattner, Construction and characterization of the hybrid bacteriophage lambda charon vectors for DNA cloning, *J. Virol.* 29:555–575 (1979).

Wilmut, et al., Viable offspring derived from fetal and adult mammalian cells, *Nature, 385:*810–813, 1997.

Wong et al., Sequence organisation and cytological localization of the minor satellite of mouse, *Nucl. Acids Res.* *16*:11645–11661 (1988).

Yamada et al., Multiple chromosomes carrying tumor suppressor activity for a uterine endometrial carcinoma cell line identified by microcell–mediated chromosome transfer, *Oncogene* *5*:1141–1147 (1990).

Yates et al., A *cis*–acting element from the Epstein–Barr viral genome that permits stable replication of recombinant plasmids in latently infected cells, *Proc. Natl. Acad. Sci. USA* *81*:3806–3810 (1984).

Yates et al., Stable replication of plasmids derived from Epstein–Barr virus in various mammalian cells, *Nature* *313*:812–815 (1985).

Yeung et al., Human CD4–major histocompatibility complex (Dqw6) transgenic mice in an endogenous CD4/CD8–deficient background: reconstitution of phenotype and humano–restricted function, *J. Exp. Med. 180*:1911–1920 (1994).

Yoon, et al., Mapping of replication initiation sites in human ribosomal DNA by Nascent–Strand abundance analysis, *Mol. Cell. Bio.*, p. 2482–2489, May 1995.

Yurov, Identification and characterization of two distinct polymorphic α–satellite DNA sequences from centromeric regions of the chromosomes 13 and 21 (A2299), *Cytogenet. Cell Genet. 51*:1114 (1989).

Yurov, Collection of α–satellite DNA probes: Highly polymorphic markers for centromeric regions of all human chromosomes (A2298), *Cytogenet. Cell Genet. 51*:1114 (1989).

Zang, et al., "Production of recombinant proteins in Chinese hamster ovary cells using a protein–free cell culture medium", *Bio/Technology 13*:389–392, (1995).

Zemskova and Escher, IAP DNA sequences and mouse chromosome instability, Loma Linda University APC Conference, Mar., 1997.

Zhang, et al., "T–Cell cytokine responses in human infection with *Mycobacterium tuberculosis*", *Infection and Immunity*, p. 3231–3234, (1995).

\* cited by examiner

EC3/7 MOUSE LMTK FIBROBLAST CELL LINE WITH neo-CENTROMERE
(HADLACZKY ET AL. PROC. NATL. ACAD. SCI. USA, 88: 8106-8110, 1991)
   DEPOSITED IN THE EUROPEAN COLLECTION OF ANIMAL CELL CULTURE (ECACC) ACCESSION NUMBER 9005 1001
   SINGLE-CELL SUBCLONING EC3/7CS MOUSE LMTK FIBROBLAST CELL LINES WITH neo-MINICHROMOSOME
(HADLACZKY ET AL. PROC. NATL. ACAD. SCI. USA, 88: 8106-8110, 1991)
   COTRANSFECTION WITH PLASMIDS pH132 (HIVRIBOZYME, HYGROMYCIN RESISTANCE) pCH110 (β-GALACTOSIDASE), AND LAMBDA PHAGE (λC1 875 SAM7) DNA, SELECTION WITH HYGROMYCIN B.

TF1004G-19C5* - MOUSE LMTK FIBROBLAST CELL LINES WITH neo-MINICHROMOSOME, AND STABLE "SAUSAGE" CHROMOSOME
   FUSION WITH CHINESE HAMSTER (CHO K20) CELL LINE, SELECTION WITH HYGROMYCIN B AND HAT.

19C5xHa4 - MOUSE-HAMSTER HYBRID CELL LINE CARRYING THE neo-MINICHROMOSOME AND THE "SAUSAGE" CHROMOSOME, CONTAINING COMPLETE HAMSTER GENOME AND PARTIAL MOUSE GENOME.
   BrdU TREATMENT, SINGLE CELL CLONING, SELECTION: G418 (NEOMYCIN) OR HYGROMYCIN, OR BOTH G3D5* - MOUSE-HAMSTER HYBRID CELL LINE CARRYING THE neo-MINICHROMOSOME AND THE MEGACHROMOSOME, CONTAINING COMPLETE HAMSTER GENOME AND PARTIAL MOUSE GENOME.

H1D3* - MOUSE-HAMSTER HYBRID CELL LINE CARRYING NO neo-MINICHROMOSOME BUT THE MEGACHROMOSOME, IS PRESENT, CONTAINING COMPLETE HAMSTER GENOME AND PARTIAL MOUSE GENOME.
   FUSION WITH CD4+ HeLa CELL LINE CARRYING THE CD4 AND NEOMYCIN RESISTANCE GENE PLASMID CONSTRUCT (CD4neo), SELECTION WITH G418 AND HYGROMYCIN B H1xHe41* - MOUSE-HAMSTER-HUMAN HYBRID CELL LINE CARRYING THE MEGACHROMOSOME PRESENT, CONTAINING COMPLETE HAMSTER GENOME, AND PARTIAL MOUSE GENOME, AND A SINGLE HUMAN CHROMOSOME WITH INTEGRATED CD4neo CONSTRUCT (UNPUBLISHED).
   REPEATED BrdU TREATMENT, SINGLE-CELL CLONING 1B3 - SAME AS H1xHe41, BUT APPROXIMATELY 25% OF THE CELLS ARE CARRYING A TRUNCATED MEGACHROMOSOME

Figure 4

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
      (A) LENGTH: 1293 base pairs
      (B) TYPE: nucleic acid
      (C) STRANDEDNESS: single
      (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(ix) FEATURE:

(xi) SEQUENCE DESCRIPTION: SEQ ID NO:1:

```
GAATTCATCA TTTTTCANGT CCTCAAGTGG ATGTTTCTCA TTTNCCATGA TTTTAAGTTT      60

TCTCGCCATA TTCCTGGTCC TACAGTGTGC ATTTCTCCAT TTTNCACGTT TTNCAGTGAT     120

TTCGTCATTT TCAAGTCCTC AAGTGGATGT TTCTCATTTN CCATGAATTT CAGTTTTCTN    180

GCCATATTCC ACGTCCTACA GNGGACATTT CTAAATTTNC CACCTTTTTC AGTTTTCCTC    240

GCCATATTTC ACGTCCTAAA ATGTGTATTT CTCGTTTNCC GTGATTTTCA GTTTTCTCGC    300

CAGATTCCAG GTCCTATAAT GTGCATTTCT CATTTNNCAC GTTTTTCAGT GATTTCGTCA    360

TTTTTTCAAG TCGGCAAGTG GATGTTTCTC ATTTNCCATG ATTTNCAGTT TTCTTGNAAT    420

ATTCCATGTC CTACAATGAT CATTTTTAAT TTTCCACCTT TTCATTTTTC CACGCCATAT    480

TTCATGTCCT AAAGTGTATA TTTCTCCTTT TCCGCGATTT TCAGTTTTCT CGCCATATTC    540

CAGGTCCTAC AGTGTGCATT CCTCATTTTT CACCTTTTTC ACTGATTTCG TCATTTTTCA    600

AGTCGTCAAC TGGATCTTTC TAATTTTCCA TGATTTTCAG TTATCTTGTC ATATTCCATG    660

TCCTACAGTG GACATTTCTA AATTTTCCAA CTTTTTCAAT TTTTCTCGAC ATATTTGACG    720

TGCTAAAGTG TGTATTTCTT ATTTTCCGTG ATTTTCAGTT TTCTCGCCAT ATTCCAGGTC    780

CTAATAGTGT GCATTTCTCA TTTTTCACGT TTTTCAGTGA TTTCGTCATT TTTTCCAGTT    840
```

```
GTCAAGGGGA TGTTTCTCAT TTTCCATGAG TGTCAGTTTT CTTGCTATAT TCCATGTCCT      900

ACAGTGACAT TTCTAAATAT TATACCTTTT TCAGTTTTTC TCACCATATT TCACGTCCTA      960

AAGTATATAT TTCTCATTTT CCCTGATTTT CAGTTTCCTT GCCATATTCC AGGTCCTACA     1020

GTGTGCATTT CTCATTTTTC ACGTTTTTCA GTAATTTCTT CATTTTTTAA GCCCTCAAAT     1080

GGATGTTTCT CATTTTCCAT GATTTTCAGT TTTCTTGCCA TATACCATGT CCTACAGTGG     1140

ACATTTCTAA ATTATCCACC TTTTTCAGTT TTTCATCGGC ACATTTCACG TCCTAAAGTG     1200

TGTATTTCTA ATTTTCAGTG ATTTTCAGTT TTCTCGCCAT ATTCCAGGAC CTACAGTGTG     1260

CATTTCTCAT TTTTCACGTT TTTCAGTGAA TTC                                  1293

(2) INFORMATION FOR SEQ ID NO:2:

(i) SEQUENCE CHARACTERISTICS:
        (A) LENGTH: 1044 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(ix) FEATURE:

(xi) SEQUENCE DESCRIPTION: SEQ ID NO:2:

AGGCCTATGG TGAAAAAGGA AATATCTTCC CCTGAAAACT AGACAGAAGG ATTCTCAGAA       60

TCTTATTTGT GATGTGCGCC CCTCAACTAA CAGTGTTGAA GCTTTCTTTT GATAGAGCAG      120

TTTTGAAACA CTCTTTTTGT AAAATCTGCA AGAGGATATT TGGATAGCTT TGAGGATTTC      180

CGTTGGAAAC GGGATTGTCT TCATATAAAC CCTAGACAGA AGCATTCTCA GAAGCTTCAT      240

TGGGATGTTT CAGTTGAAGT CACAGTGTTG AACAGTCCCC TTTCATAGAG CAGGTTTGAA      300

ACACTCTTTT TTGTAGTATC TGGAAGTGGA CATTTGGAGC GATCTCAGGA CTGCGGTGAA      360

AAAGGAAATA TCTTCCAATA AAAGCTAGAT AGAGGCAATG TCAGAAACCT TTTTCATGAT      420

GTATCTACTC AGCTAACAGA GTTGAACCTT CCTTTGAGAG AGCAGTTTTG AAACACTCTT      480

TTTGTGGAAT CTGCAAGTGG ATATTTGTCT AGCTTTGAGG ATTTCGTTGG GAAACGGGAT      540

TACATATAAA AAGCAGACAG CAGCATTCCC AGAAACTTCT TTGTGATGTT TGCATTCAAG      600

TCACAGAGTT GAACATTCCC TTTCATAGAG CAGGTTTGAA ACACACTTTT TGATGTATCT      660

GGATGTGGAC ATTTGCAGCG CTTTCAGGCC TAAGGTGAAA AGGAAATATC TTCCCCTGAA      720

AACTAGACAG AAGCATTCTC AGAAACTTAT TTGTGATGTG CGCCCTCAAC TAACAGTGTT      780

GAAGCTTTCT TTTGATAGAG GCAGTTTTGA AACACTCTTT TGTGGAATCT GCAAGTGGAT      840

ATTTGTCTAG CTTTGAGGAT TTCTTTGGAA ACGGGATTAC ATATAAAAAG CAGACAGCAG      900

CATTCCCAGA ATCTTGTTTG TGATGTTTGC ATTCAAGTCA CAGAGTTGAA CATTCCCTTT      960

CAGAGAGCAG GTTGAACAC TCTTTTTATA GTATCTGGAT GTGGACATTT GGAGCGCTTT     1020

CAGGGGGGAT CCTCTAGAAT TCCT                                           1044

(2) INFORMATION FOR SEQ ID NO:3:

(i) SEQUENCE CHARACTERISTICS:
```

(A) LENGTH: 2492 base pairs
(B) TYPE: nucleic acid
(C) STRANDEDNESS: single
(D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(ix) FEATURE:

(xi) SEQUENCE DESCRIPTION: SEQ ID NO:3:

```
CTGCAGCTGG GGGTCTCCAA TCAGGCAGGG GCCCCTTACT ACTCAGATGG GGTGGCCGAG     60

TAGGGGAAGG GGGTGCAGGC TGCATGAGTG GACACAGCTG TAGGACTACC TGGGGGCTGT    120

GGATCTATGG GGGTGGGGAG AAGCCCAGTG ACAGTGCCTA GAAGAGACAA GGTGGCCTGA    180

GAGGGTCTGA GGAACATAGA GCTGGCCATG TTGGGGCCAG GTCTCAAGCA GGAAGTGAGG    240

AATGGGACAG GCTTGAGGAT ACTCTACTCA GTAGCCAGGA TAGCAAGGAG GGCTTGGGGT    300

TGCTATCCTG GGGTTCAACC CCCCAGGTTG AAGGCCCTGG GGGAGATGGT CCCAGGACAT    360

ATTACAATGG ACACAGGAGG TTGGGACACC TGGAGTCACC AAACAAAACC ATGCCAAGAG    420

AGACCATGAG TAGGGGTGTC CAGTCCAGCC CTCTGACTGA GCTGCATTGT TCAAATCCAA    480

AGGGCCCCTG CTGCCACCTA GTGGCTGATG GCATCCACAT GACCCTGGGC CACACGCGTT    540

TAGGGTCTCT GTGAAGACCA AGATCCTTGT TACATTGAAC GACTCCTAAA TGAGCAGAGA    600

TTTCCACCTA TTCGAAACAA TCACATAAAA TCCATCCTGG AAAAAGCCTG GGGGATGGCA    660

CTAAGGCTAG GGATAGGGTG GGATGAAGAT TATAGTTACA GTAAGGGGTT TAGGGTTAGG    720

GATCAACGTT GGTTAGGAGT TAGGGATACA GTAGGGTACC GGTAGGGTTA GGGGTTAGGG    780

TTAGGGGTTA GGGTTAGGGT TAGGGTTAGG GTTAGGGTTA GGGGTTAGGG GTTAGGGTTA    840

GGGTTAGGTT TTGGGGTGGC GTATTTTGGT CTTATACGCT GTGTTCCACT GGCAATGAAA    900

AGAGTTCTTG TTTTTCCTTC AGCAATTTGT CATTTTTAAA AGAGTTTAGC AATTCTAACA    960

GATATAGACC AGCTGTGCTA TCTCATTGTG GTTTTCAATT GTAACCACAT TGTGGTTTCA   1020

ATGTGTTTAC TTGCCATCTG TAGATCTTCT TTGCGTGAGG TGTCTGTTCA GATGTGTGTG   1080

CATTTCTTGN NTTTNGGCTG TTTAACTTAT TGTTTAGTTT TAATAATTTT TTATATATTT   1140

GAAGACAAAT CTTTCTCAGA TGTGTATTTG CAAATATTTC TTCAATATGA GGCTTGCTTT   1200

TGTCTCTAAC AAGGTCTCTT CAGAGATAAC TTAAATATAA GAAATCCACA CTGTCACTTC   1260

TTTTGTGTAT ATCTACCTTT TGTGTCATTT GTTAAAATTC ATTACCAAAC CCAAAGGCAG   1320

ATAGCTTTTC TTCTATTGTT TCTTCTAGAA ATTTGTATAG TTTTGCATTT TTAGTGTAAG   1380

GATGATTTTG AGTGATTATT TGTGTAAGTT GTAAAGTTTT CGTCTATATC CATATCATTT   1440

CTTATGGTTT CCAATTAATC GTTCCCTCAC TATTTTTGGG AAAGACACAG GATAGTGGGC   1500

TTTGTTAGAG TAGATAGGTA GCTAGACATG AACAGGAGGG GGCCTCCTGG AAAAGGGAAA   1560

GTCTGGGAAG GCTCACCTGG AGGACCACCA AAAATTCACA TATTAGTAGC ATCTCTAGTG   1620

CTGGAGTGGA TGGGCACTTG TCAATTGTGG GTAGGAGGGA AAAGAGGTCC TATGCAGAAA   1680

GAAACTCCCT AGAACTCCTC TGAAGATGCC CCAATCATTC ACTCTGCAAT AAAAATGTCA   1740

GAATATTGCT AGCTACATGC TGATAAGGNN AAAGGGGACA TTCTTAAGTG AAACCTGGCA   1800
```

```
CCATAAGTAC AGATTAGGGC AGAGAAGGAC ATTCAAAAGA GGCAGGCGCA GTAGGTACAA    1860

ACGTGATCGC TGTCAGTGTG CCTGGGATGG CGGGAAGGAG GCTGGTGCCA GAGTGGATTC    1920

GTATTGATCA CCACACATAT ACCTCAACCA ACAGTGAGGA GGTCCCACAA GCCTAAGTGG    1980

GGCAAGTTGG GGAGCTAAGG CAGTAGCAGG AAAACCAGAC AAAGAAAACA GGTGGAGACT    2040

TGAGACAGAG GCAGGAATGT GAAGAAATCC AAAATAAAAT TCCCTGCACA GGACTCTTAG    2100

GCTGTTTAAT GCATCGCTCA GTCCCACTCC TCCCTATTTT TCTACAATAA ACTCTTTACA    2160

CTGTGTTTCT TTTCAATGAA GTTATCTGCC ATCTTTGTAT TGCCTCTTGG TGAAAATGTT    2220

TCTTCCAAGT TAAACAAGAA CTGGGACATC AGCTCTCCCC AGTAATAGCT CCGTTTCAGT    2280

TTGAATTTAC AGAACTGATG GGCTTAATAA CTGGCGCTCT GACTTTAGTG GTGCAGGAGG    2340

CCGTCACACC GGGACCAAGA GTGCCCTGCC TAGTCCCCAT CTGCCCGCAG GTGGCGGCTG    2400

CCTCGACACT GACAGCAATA GGGTCCGGCA GTGTCCCCAG CTGCCAGCAG GGGGCGTACG    2460

ACGACTACAC TGTGAGCAAG AGGGCCCTGC AG                                  2492
```

(2) INFORMATION FOR SEQ ID NO:4:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(ix) FEATURE:

(xi) SEQUENCE DESCRIPTION: SEQ ID NO:4:

```
GGGGAATTCA TTGGGATGTT TCAGTTGA                                        28
```

(2) INFORMATION FOR SEQ ID NO:5:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(ix) FEATURE:

(xi) SEQUENCE DESCRIPTION: SEQ ID NO:5:

```
CGAAAGTCCC CCCTAGGAGA TCTTAAGGA                                       29
```

(2) INFORMATION FOR SEQ ID NO:6:

(i) SEQUENCE CHARACTERISTICS:
        (A) LENGTH: 47 base pairs

```
        (B) TYPE: nucleic acid
        (C) STRANDEDNESS: single
        (D) TOPOLOGY: linear (ii) MOLECULE TYPE: RNA (iii) HYPOTHETICAL: NO (iv) ANTI-SENSE: NO (v) FRAGMENT TYPE:

(vi) ORIGINAL SOURCE:

(ix) FEATURE:

(xi) SEQUENCE DESCRIPTION: SEQ ID NO:6:

CCGCTTAATA CTCTGATGAG TCCGTGAGGA CGAAACGCTC TCGCACC                47

(2) INFORMATION FOR SEQ ID NO:7:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(ix) FEATURE:

(xi) SEQUENCE DESCRIPTION: SEQ ID NO:7:

CGATTTAAAT TAATTAAGCC CGGGC                                        25

(2) INFORMATION FOR SEQ ID NO:8:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(ix) FEATURE:

(xi) SEQUENCE DESCRIPTION: SEQ ID NO:8:

TAAATTTAAT TAATTCGGGC CCGTCGA                                      27

(2) INFORMATION FOR SEQ ID NO:9:

(i) SEQUENCE CHARACTERISTICS:
        (A) LENGTH: 69 base pairs
        (B) TYPE: nucleic acid
        (C) STRANDEDNESS: single
        (D) TOPOLOGY: linear
```

(ii) MOLECULE TYPE: Genomic DNA (ix) FEATURE:
    (D) OTHER INFORMATION: IL-2 signal sequence (xi) SEQUENCE DESCRIPTION: SEQ ID NO:9:

| ATG | TAC | AGG | ATG | CAA | CTC | CTG | TCT | TGC | ATT | GCA | CTA | AGT | CTT | GCA | CTT | 48 |
|---|---|---|---|---|---|---|---|---|---|---|---|---|---|---|---|---|
| Met | Tyr | Arg | Met | Gln | Leu | Leu | Ser | Cys | Ile | Ala | Leu | Ser | Leu | Ala | Leu | |
| 1 | | | | 5 | | | | | 10 | | | | | 15 | | |

| GTC | ACA | AAC | AGT | GCA | CCT | ACT | 69 |
|---|---|---|---|---|---|---|---|
| Val | Thr | Asn | Ser | Ala | Pro | Thr | |
| | | | | 20 | | | |

(2) INFORMATION FOR SEQ ID NO:10:

(i) SEQUENCE CHARACTERISTICS:
        (A) LENGTH: 945 base pairs
        (B) TYPE: nucleic acid
        (C) STRANDEDNESS: single
        (D) TOPOLOGY: linear (ii) MOLECULE TYPE: cDNA (vi) ORIGINAL SOURCE:

(ix) FEATURE:
        (A) NAME/KEY: Coding Sequence
        (B) LOCATION: 1...942
        (D) OTHER INFORMATION: Renilla Reinformis Luciferase (x) PUBLICATION INFORMATION:
        (H) DOCUMENT NUMBER: 5,418,155

(xi) SEQUENCE DESCRIPTION: SEQ ID NO:10:

| AGC | TTA | AAG | ATG | ACT | TCG | AAA | GTT | TAT | GAT | CCA | GAA | CAA | AGG | AAA | CGG | 48 |
|---|---|---|---|---|---|---|---|---|---|---|---|---|---|---|---|---|
| Ser | Leu | Lys | Met | Thr | Ser | Lys | Val | Tyr | Asp | Pro | Glu | Gln | Arg | Lys | Arg | |
| 1 | | | | 5 | | | | | 10 | | | | | 15 | | |

| ATG | ATA | ACT | GGT | CCG | CAG | TGG | TGG | GCC | AGA | TGT | AAA | CAA | ATG | AAT | GTT | 96 |
|---|---|---|---|---|---|---|---|---|---|---|---|---|---|---|---|---|
| Met | Ile | Thr | Gly | Pro | Gln | Trp | Trp | Ala | Arg | Cys | Lys | Gln | Met | Asn | Val | |
| | | | 20 | | | | | 25 | | | | | 30 | | | |

| CTT | GAT | TCA | TTT | ATT | AAT | TAT | TAT | GAT | TCA | GAA | AAA | CAT | GCA | GAA | AAT | 144 |
|---|---|---|---|---|---|---|---|---|---|---|---|---|---|---|---|---|
| Leu | Asp | Ser | Phe | Ile | Asn | Tyr | Tyr | Asp | Ser | Glu | Lys | His | Ala | Glu | Asn | |
| | | 35 | | | | | 40 | | | | | 45 | | | | |

| GCT | GTT | ATT | TTT | TTA | CAT | GGT | AAC | GCG | GCC | TCT | TCT | TAT | TTA | TGG | CGA | 192 |
|---|---|---|---|---|---|---|---|---|---|---|---|---|---|---|---|---|
| Ala | Val | Ile | Phe | Leu | His | Gly | Asn | Ala | Ala | Ser | Ser | Tyr | Leu | Trp | Arg | |
| | | 50 | | | | | 55 | | | | | 60 | | | | |

| CAT | GTT | GTG | CCA | CAT | ATT | GAG | CCA | GTA | GCG | CGG | TGT | ATT | ATA | CCA | GAT | 240 |
|---|---|---|---|---|---|---|---|---|---|---|---|---|---|---|---|---|
| His | Val | Val | Pro | His | Ile | Glu | Pro | Val | Ala | Arg | Cys | Ile | Ile | Pro | Asp | |
| 65 | | | | 70 | | | | | 75 | | | | | 80 | | |

| CTT | ATT | GGT | ATG | GGC | AAA | TCA | GGC | AAA | TCT | GGT | AAT | GGT | TCT | TAT | AGG | 288 |
|---|---|---|---|---|---|---|---|---|---|---|---|---|---|---|---|---|
| Leu | Ile | Gly | Met | Gly | Lys | Ser | Gly | Lys | Ser | Gly | Asn | Gly | Ser | Tyr | Arg | |
| | | | 85 | | | | | 90 | | | | | 95 | | | |

| TTA | CTT | GAT | CAT | TAC | AAA | TAT | CTT | ACT | GCA | TGG | TTG | AAC | TTC | TTA | ATT | 336 |
|---|---|---|---|---|---|---|---|---|---|---|---|---|---|---|---|---|
| Leu | Leu | Asp | His | Tyr | Lys | Tyr | Leu | Thr | Ala | Trp | Leu | Asn | Phe | Leu | Ile | |
| | | | 100 | | | | | 105 | | | | | 110 | | | |

| TAC | CAA | AGA | AGA | TCA | TTT | TTT | GTC | GGC | CAT | GAT | TGG | GGT | GCT | TGT | TTG | 384 |
|---|---|---|---|---|---|---|---|---|---|---|---|---|---|---|---|---|
| Tyr | Gln | Arg | Arg | Ser | Phe | Phe | Val | Gly | His | Asp | Trp | Gly | Ala | Cys | Leu | |
| | | 115 | | | | | 120 | | | | | 125 | | | | |

| GCA | TTT | CAT | TAT | AGC | TAT | GAG | CAT | CAA | GAT | AAG | ATC | AAA | GCA | ATA | GTT | 432 |
|---|---|---|---|---|---|---|---|---|---|---|---|---|---|---|---|---|
| Ala | Phe | His | Tyr | Ser | Tyr | Glu | His | Gln | Asp | Lys | Ile | Lys | Ala | Ile | Val | |
| | | 130 | | | | | 135 | | | | | 140 | | | | |

| CAC | GCT | GAA | AGT | GTA | GTA | GAT | GTG | ATT | GAA | TCA | TGG | GAT | GAA | TGG | CCT | 480 |
|---|---|---|---|---|---|---|---|---|---|---|---|---|---|---|---|---|
| His | Ala | Glu | Ser | Val | Val | Asp | Val | Ile | Glu | Ser | Trp | Asp | Glu | Trp | Pro | |
| 145 | | | | 150 | | | | | 155 | | | | | 160 | | |

| GAT | ATT | GAA | GAA | GAT | ATT | GCG | TTG | ATC | AAA | TCT | GAA | GAA | GGA | GAA | AAA | 528 |
|---|---|---|---|---|---|---|---|---|---|---|---|---|---|---|---|---|

```
            Asp Ile Glu Glu Asp Ile Ala Leu Ile Lys Ser Glu Glu Gly Glu Lys
                        165                 170                 175

ATG GTT TTG GAG AAT AAC TTC TTC GTG GAA ACC ATG TTG CCA TCA AAA              576
Met Val Leu Glu Asn Asn Phe Phe Val Glu Thr Met Leu Pro Ser Lys
            180                 185                 190

ATC ATG AGA AAG TTA GAA CCA GAA GAA TTT GCA GCA TAT CTT GAA CCA              624
Ile Met Arg Lys Leu Glu Pro Glu Glu Phe Ala Ala Tyr Leu Glu Pro
        195                 200                 205

TTC AAA GAG AAA GGT GAA GTT CGT CGT CCA ACA TTA TCA TGG CCT CGT              672
Phe Lys Glu Lys Gly Glu Val Arg Arg Pro Thr Leu Ser Trp Pro Arg
    210                 215                 220

GAA ATC CCG TTA GTA AAA GGT GGT AAA CCT GAC GTT GTA CAA ATT GTT              720
Glu Ile Pro Leu Val Lys Gly Gly Lys Pro Asp Val Val Gln Ile Val
225                 230                 235                 240

AGG AAT TAT AAT GCT TAT CTA CGT GCA AGT GAT GAT TTA CCA AAA ATG              768
Arg Asn Tyr Asn Ala Tyr Leu Arg Ala Ser Asp Asp Leu Pro Lys Met
                245                 250                 255

TTT ATT GAA TCG GAT CCA GGA TTC TTT TCC AAT GCT ATT GTT GAA GGC              816
Phe Ile Glu Ser Asp Pro Gly Phe Phe Ser Asn Ala Ile Val Glu Gly
            260                 265                 270

GCC AAG AAG TTT CCT AAT ACT GAA TTT GTC AAA GTA AAA GGT CTT CAT              864
Ala Lys Lys Phe Pro Asn Thr Glu Phe Val Lys Val Lys Gly Leu His
        275                 280                 285

TTT TCG CAA GAA GAT GCA CCT GAT GAA ATG GGA AAA TAT ATC AAA TCG              912
Phe Ser Gln Glu Asp Ala Pro Asp Glu Met Gly Lys Tyr Ile Lys Ser
    290                 295                 300

TTC GTT GAG CGA GTT CTC AAA AAT GAA CAA TAA                                  945
Phe Val Glu Arg Val Leu Lys Asn Glu Gln
305                 310
```

(2) INFORMATION FOR SEQ ID NO:11:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(ix) FEATURE:

(xi) SEQUENCE DESCRIPTION: SEQ ID NO:11:

```
TTTGAATTC A TGTACAGGAT GCAACTCCTG                                             30
```

(2) INFORMATION FOR SEQ ID NO:12:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO -continued

```
    (v) FRAGMENT TYPE:

(vi) ORIGINAL SOURCE:

(ix) FEATURE:

(xi) SEQUENCE DESCRIPTION: SEQ ID NO:12:

TTTGAATTCA GTAGGTGCAC TGTTTGTCAC                                    30
```

ARTIFICIAL CHROMOSOMES, USES THEREOF AND METHODS FOR PREPARING ARTIFICIAL CHROMOSOMES

RELATED APPLICATIONS

This application is a continuation of U.S. application Ser. No. 08/629,822, filed Apr. 10, 1996 now abandoned. This application is related to U.S. application Ser. No. 08/759,558, now U.S. Pat. No. 5,288,625 and to U.S. application Ser. No. 08/375,271, filed Jan. 19, 1995, which is a continuation of U.S. application Ser. No. 08/080,097, filed Jun. 23, 1993 which is a continuation of U.S. application Ser. No. 07/892,487, filed Jun. 3, 1992, which is a continuation of U.S. application Ser. No. 07/521,073, filed May 9, 1990.

The subject matter of each of the above-listed U.S. applications is incorporated in its entirety by reference thereto.

FIELD OF THE INVENTION

The present invention relates to methods for preparing cell lines that contain artificial chromosomes, to methods for isolation of the artificial chromosomes, targeted insertion of heterologous DNA into the chromosomes, isolation of the chromosomes, and delivery of the chromosomes to selected cells and tissues. Also provided are cell lines for use in the methods, and cell lines and chromosomes produced by the methods.

BACKGROUND OF THE INVENTION

Several viral vectors, non-viral, and physical delivery systems for gene therapy have been developed [see, e.g., Mitani et al. (1993) *Trends Biotech.* 11:162–166]. The presently available systems, however, have numerous limitations, particularly where persistent, stable, or controlled gene expression is required. These limitations include: (1) size limitations because there is a limit, generally on order of about ten kilobases [kB], at most, to the size of the DNA insert [gene] that can be accepted by viral vectors, whereas a number of mammalian genes of possible therapeutic importance are well above this limit, especially if all control elements are included; (2) the inability to specifically target integration so that random integration is required which carries a risk of disrupting vital genes or cancer suppressor genes; (3) the expression of randomly integrated therapeutic genes may be affected by the functional compartmentalization in the nucleus and are affected by chromatin-based position effects; (4) the copy number and consequently the expression of a given gene to be integrated into the genome cannot be controlled. Thus, improvements in gene delivery and stable expression systems are needed [see, e.g., Mulligan (1993) *Science* 260:926–932].

In addition, safe and effective gene therapy methods and vectors should have numerous features that are not assured by the presently available systems. For example, a safe vector should not contain DNA elements that can promote unwanted changes by recombination or mutation in the host genetic material, should not have the potential to initiate deleterious effects in cells, tissues, or organisms carrying the vector, and should not interfere with genomic functions. In addition, it would be advantageous for the vector to be non-integrative, or designed for site-specific integration. Also, the copy number of therapeutic gene(s) carried by the vector should be controlled and stable, the vector should secure the independent and controlled function of the introduced gene(s); and the vector should accept large (up to Mb size) inserts and ensure the functional stability of the insert.

The limitations of existing gene delivery technologies, however, argue for the development of alternative vector systems suitable for transferring large [up to Mb size or larger] genes and gene complexes together with regulatory elements that will provide a safe, controlled, and persistent expression of the therapeutic genetic material.

At the present time, none of the available vectors fulfill these requirements. Some of these characteristics, however, are possessed by chromosomes. Thus, an artificial chromosome would be an ideal vector for gene therapy, as well as for production of gene products that require coordination of expression of numerous genes or that are encoded by large genes, and other uses. Artificial chromosomes for expression of heterologous genes in yeast are available, but construction of a mammalian artificial chromosome has not been achieved. Such construction has been hindered by the lack of an isolated, functional, mammalian centromere and uncertainty regarding the requisites for its production and stable replication. Unlike in yeast, there are no selectable genes in close proximity to a mammalian centromere, and the presence of long runs of highly repetitive pericentric heterochromatic DNA makes the isolation of a mammalian centromere using presently available methods, such as chromosome walking, virtually impossible. Other strategies are required for production of mammalian artificial chromosomes, and some have been developed. For example, U.S. Pat. No. 5,288,625 provides a cell line that contains an artificial chromosome, a minichromosome, that is about 20 to 30 megabases. Methods provided for isolation of these chromosomes, however, provide preparations of only about 10–20% purity. Thus, development of alternative artificial chromosomes and perfection of isolation methods as well as development of more versatile chromosomes and further characterization of the minichromosomes is required to realize the potential of this technology.

Therefore, it is an object herein to provide mammalian artificial chromosomes and methods for introduction of foreign DNA into such chromosomes. It is also an object herein to provide methods for introduction of the artificial mammalian chromosome into selected cells, and to provide the resulting cells, as well as transgenic animals and plants that contain the artificial chromosomes. It is also an object herein to provide methods for gene therapy and expression of gene products using artificial chromosomes. It is a further object herein to provide methods for constructing species-specific artificial chromosomes.

SUMMARY OF THE INVENTION

Mammalian artificial chromosomes [MACs] are provided. Also provided are artificial chromosomes for other higher eukaryotic species, such as insects and fish, produced using the MACS are provided herein. Methods for generating and isolating such chromosomes. Methods using the MACs to construct artificial chromosomes from other species, such as insect and fish species are also provided. The artificial chromosomes are fully functional stable chromosomes. Two types of artificial chromosomes are provided. One type, herein referred to as SATACs [satellite artificial chromosomes] are stable heterochromatic chromosomes, and the another type are minichromosomes based on amplification of euchromatin.

Artificial chromosomes permit targeted integration of megabase pair size DNA fragments that contain single or multiple genes. Thus methods using the MACs to introduce the genes into cells, animals and tissues are also provided. The artificial chromosomes with integrated heterologous DNA are to be used in methods of gene therapy, in methods of production of gene products, particularly products that require expression of multigene biosynthetic pathways, and also are intended for delivery into the nuclei of germane cells, such as embryo-derived stem cells [ES cells] for production of transgenic animals.

Mammalian artificial chromosomes provide extragenomic specific integration sites for introduction of genes encoding proteins of interest and permit megabase size DNA integration so that, for example, genes encoding an entire metabolic pathway or a very large gene, such as the cystic fibrosis [CF; ~600 kb] gene, several genes, such as a series of antigens for preparation of a multivalent vaccine, can be stably introduced into a cell. Vectors for targeted introduction of such genes, including the tumor suppressor genes, such as p53, the cystic fibrosis transmembrane regulator gene [CFTR], anti-HIV ribozymes, such as an anti-HIV gag ribozyme, into the artificial chromosomes also provided.

The chromosomes provided herein are generated by introducing heterologous DNA that includes DNA encoding a selectable marker into cells, preferably a stable cell line, growing the cells under selective conditions, and identifying from among the resulting clones those that include chromosomes with more than one centromere or that have chromosomes that are fragments of chromosomes that had more than one centromere. The amplification that produces the additional centromere occurs in cells that contain chromosomes in which the heterologous DNA has integrated near the centromere in the pericentric region of the chromosome. The selected clonal cells are then used to generate artificial chromosomes.

In preferred embodiments, the DNA with the selectable marker that is introduced includes sequences that target it to the pericentric region of the chromosome. For example, vectors, such as pTEMPUD, which includes such DNA specific for mouse satellite DNA, are provided. Also provided are derivatives of pTEMPUD that specifically target human satellite sequences. Upon integration, these vectors can induce the amplification.

Artificial chromosomes are generated by culturing the cells with the dicentric chromosomes under conditions whereby the chromosome breaks to form a minichromosome and formerly dicentric chromosome. The artificial chromosomes [the SATACs] are generated, not from the minichromosome fragment as, for example, in U.S. Pat. No. 5,288,625, but from the fragment of the formerly dicentric chromosome.

Among the MACs provided herein are the SATACs, which are primarily made up of repeating units of short satellite DNA and are fully heterochromatic, so that absent insertion of heterologous or foreign DNA, the chromosomes do not contain genetic information. They can thus be used as "safe" vectors for delivery of DNA to mammalian hosts because they do not contain any potentially harmful genes.

In addition to MACs methods for generating euchromatic minichromsomes and the use thereof are also provided herein. Methods for generating one type of MAC the minichromosome, previously described in U.S. Pat. No. 5,288,625, and the use thereof for expression of heterologous DNA are provided. Cell lines containing the minichromosome and the use thereof for cell fusion are also provided.

In one embodiment, a cell line containing the mammalian minichromosome is used as recipient cells for donor DNA encoding a selected gene or multiple genes. The donor DNA is linked to a second selectable marker and is targeted to and integrated into the minichromosome. The resulting chromosome is transferred by cell fusion into an appropriate recipient cell line, such as a Chinese hamster cell line [CHO]. After large scale production of the cells carrying the engineered chromosome, the chromosome is isolated. In particular, metaphase chromosomes are obtained, such as by addition of colchicine, and they are purified from the cell lysate. These chromosomes are used for cloning, sequencing and for delivery of heterologous DNA into cells.

Also provided are SATACs of various sizes that are formed by repeated culturing under selective conditions and subcloning of cells that contain chromosomes produced from the formerly dicentric chromosomes. These chromosomes are based on repeating units 7.5 to 10 Mb referred to herein as megareplicons, that are tandem blocks of satellite DNA flanked by heterologous non-satellite DNA. Amplification produces a tandem array of identical chromosome segments [each called an amplicon] that contain two inverted megareplicons bordered by heterologous ["foreign"] DNA. Repeated cell fusion, growth on selective medium and/or BrdU [5-bromodeoxyuridine] treatment or other genome destabilizing reagent or agent, such as ionizing radiation, including X-rays, and subcloning results in cell lines that carry stable heterochromatic or partially heterochromatic chromosomes, including a 150–200 Mb "sausage" chromosome, a 500–1000 Mb gigachromosome, a stable 250–400 Mb megachromosome and various smaller stable chromosomes derived therefrom. These chromosomes are based on these repeating units and can include heterologous DNA that is expressed.

Thus methods for producing MACs of both types are provided. These methods are applicable to any higher eukaryotic cell, including mammals, insects and plants.

The resulting chromosomes can be purified by methods provided herein to provide vectors for introduction of the heterologous DNA into selected cells for production of the gene product encoded by the heterologous DNA, for production of transgenic animals and plants or for gene therapy. Vectors for chromosome fragmentation are provided. These vectors will be used to produce an artificial chromosome that contains a megareplicon, a centromere and two telomeres and will be between about 10 Mb and about 60 Mb, preferably between about 10 Mb-15 Mb and 30 Mb. Such artificial chromosomes may be produced by other methods. Isolation of the 7.5 Mb [or 15 Mb amplicon containing two 7.5 Mb inverted repeats] or a 30 Mb multimer thereof should provide a stable chromosomal vector that can be manipulated in vitro.

In addition, methods and vectors for fragmenting the minichromosomes and SATACs are provided. Such methods and vectors can be used for in vivo generation of smaller stable artificial chromosomes. Methods for reducing the size of the MACs to generate smaller stable self-replicating artificial chromosomes are also provided.

Methods and vectors for targeting heterologous DNA into the artificial chromosomes are also provided as are methods and vectors for fragmenting the chromosomes to produce smaller but stable and self-replicating artificial chromosomes. Vectors for targeted introduction of heterologous DNA into artificial chromosomes are provided.

The chromosomes are introduced into cells to produce stable transformed cell lines or cells, depending upon the source of the cells. Introduction is effected by any suitable method including, but not limited to electroporation, direct uptake, such as by calcium phosphate [see, e.g., Wigler et al.

(1979) *Proc. Natl. Acad. Sci. U.S.A.* 76:1373–1376; and *Current Protocols in Molecular Biolog, Vol.* 1, Wiley Inter-Science, Supplement 14, Unit 9.1.1–9.1.9 (1990)]. precipitation, uptake of isolated chromosomes by lipofection, by microcell fusion [see, EXAMPLES, see, also Lambert (1991) *Proc. Natl. Acad. Sci. U.S.A.* 88:5907–5911, U.S. Pat. No. 5,396,767] or other suitable method. The resulting cells can be used for production of proteins in the cells. The chromosomes can be isolated and used for gene delivery.

Methods for isolation of the chromosomes based on the DNA content of the chromosomes, which differs from the authentic chromsomes are provided.

These artificial chromosomes can be used in gene therapy, gene product production systems, production of humanized organs, production of transgenic plants and animals, including invertebrates, vertebrate, reptiles and insects, any organism or device that would employ chromosomal elements as information storage vehicles, and also for analysis and study of centromere function, for the production of artificial chromosome vectors that can be constructed in vitro, and for the preparation of species- specific artificial chromosomes. The artificial chromosomes can be introduced into cells using microinjection, cell fusion, microcell fusion, electroporation, electrofusion, projectile bombardment, calcium phosphate precipitation, site-specific targeting and other such methods. Cells particularly suited for use with the artificial chromosomes include, but are not limited to plant cells, particularly tomato, arabidopsis, and others, insect cells, including silk worm cells, insect larvae, fish, reptiles, amphibians, arachnids, mammalian cells, embryonic stem cells, embryos and cells for use in methods of genetic therapy, such as lymphocytes that are used in methods of adoptive immunotherapy and nerve or neural cells. Thus methods of producing gene products and transgenic animals and plants are provided. Also provided are the resulting transgenic animals and plants.

Exemplary cell lines that contain these chromosomes are also provided.

Methods for preparing artificial chromosomes for particular species and for cloning centromeres are also provided. In particular, a method for cloning a centromere from an animal or plant by preparing a library of DNA fragments that contain the genome of the plant or animal, introducing the each of the fragments into a mammalian satellite artificial chromosome [SATAC] that contains a centromere from a different species, generally a mammal, from the selected plant or animal, generally a non-mammal, and a selectable marker. The selected plant or animal is one in which the mammalian species centromere does not function. Each of the SATACs is introduced into the cells, which are grown under selective conditions, and cells with SATACs are identified. Such SATACS should contain a centromere encoded by the DNA from the library.

Also provided are libraries in which the relatively large fragments of DNA are contained on artificial chromosomes.

Transgenic animals, invertebrates and vertebrates, plants and insects, fish, reptiles, amphibians, arachnids and mammals are also provided. Of particular interest are transgenic animals that express genes that confer resistance or reduce susceptibility to disease. Since multiple genes can be introduced on a MAC, a series of genes encoding an antigen can be introduced, which up expression will serve to immunize [in a manner similar to a multivalent vaccine] the host animal against the diseases for which exposure to the antigens provide immunity or some protection.

Methods for cloning centromeres, such as mammalian centromeres, are also provided. In particular, in one embodiment, a library composed of fragments of the SATACs are cloned into YACs [yeast artificial chromosomes] that include a detectable marker, such as DNA encoding tyrosinase and then introduced into mammalian cells, such as albino mouse embryos. Mice produced from YACs that include a centromere that functions in mammals will express the detectable marker. Thus, if albino mice will be pigmented or have regions of pigmentation.

DESCRIPTION OF THE DRAWINGS

FIG. 4 sets forth the relationships among the some of the exemplary cell lines described herein.

DETAILED DESCRIPTION OF PREFERRED EMBODIMENTS

Definitions

Figure 1:
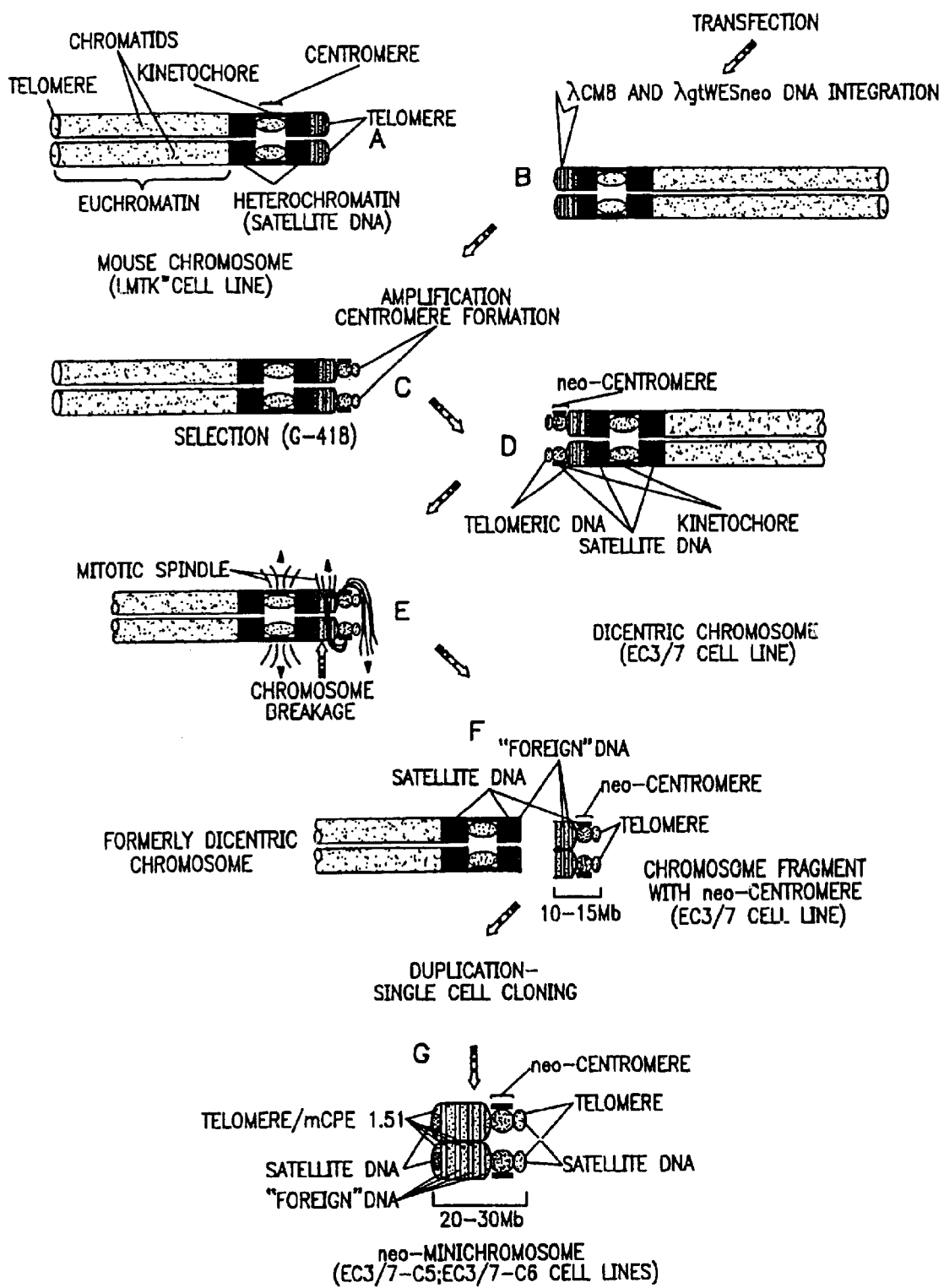
FIG. 1 is a schematic drawing depicting formation of the MMCneo [the minichromosome] chromosome. A-G represents the successive events consistent with observed data that would lead to the formation and stabilization of the minichromosome.

Unless defined otherwise, all technical and scientific terms used herein have the same meaning as is commonly understood by one of skill in the art to which this invention belongs. All patents and publications referred to herein are incorporated by reference.

As used herein, a mammalian artificial chromosome [MAC] is piece of DNA that can stably replicate and segregate alongside endogenous chromosomes. It has the capacity to accommodate and express heterologous genes inserted therein. It is referred to as a mammalian artificial chromosome because it includes an active mammalian centromere. Plant artificial chromosomes and an insect artificial chromosomes refer to chromosomes that include plant and insect centromeres, respectively. A human specific chromosome [HAC] refers to chromosomes that include human centromeres, BUGACs refer to artificial insect chromosomes, and AVACs refer to avian artificial chromosomes.

As used herein, stable maintenance of chromosomes, occurs when at least about 85%, preferably 90%, more preferably 95%, of the cells retain the chromosome. Stability is measured in the presence of selective agent. Preferably these chromosomes are also maintained in the absence of a selective agent. Stable chromosomes also retain their structure during cell culturing, suffering neither intrachromosomal nor interchromosomal rearrangements.

As used herein, growth under selective conditions, means growth of a cell under conditions that require expression of a selectable marker for survival.

As used herein, euchromatin and heteroaromatic have their recognized meanings, euchromatin refers to DNA that contains genes, and heteroaromatic refers to chromatin that has been thought to be inactive. Highly repetitive DNA sequences [satellite DNA] are located in regions of centromeric heteroaromatic [pericentric heteroaromatic]. Constitutive heteroaromatic refers to heteroaromatic that contains the highly repetitive DNA and that is constitutively condensed.

As used herein, BrdU refers to 5-bromodeoxyuridine, which during replication is inserted in place of thymidine. BrdU is used as mutagen; it also inhibits condensation of metaphase chromosomes during cell division.

As used herein, a dicentric chromosome is a chromosome that contains two centromeres. A multicentric chromosome contains more than two centromeres.

As used herein, a formerly dicentric chromosome is a chromosome that is produced when a dicentric chromosome fragments and acquires new telomeres so that two chromosomes, each having one of the centromeres, are produced. Each of the fragments, are replicable chromosomes. If one of the chromosomes undergoes amplification of euchromatic DNA to produce a full functionally chromosome that contains the heterologous DNA and primarily [at least more than 50%] euchromatin, it is a minichromosome. The remaining chromosome is a formerly dicentric chromosome. If one of the chromosomes undergoes amplification, whereby heteroaromatic [satellite DNA] is amplified, a euchromatic portion [or arm remains], it is referred to as a sausage chromosome. A chromosome that is substantially all heteroaromatic, except for portions of heterologous DNA, is called a SATAC. Such chromosomes [SATACs] can be produced from sausage chromosomes by culturing the cell containing the sausage chromosome under conditions, such as BrdU treatment and/or growth under selective conditions, that destabilize the chromosome so that a satellite artificial chromosomes [SATAC] is produced. For purposes herein, it is understand that SATACs may not necessarily be produced in multiple steps, but may appear after the initial introduction of the heterologous DNA and growth under selective conditions, or they may appear after several cycles of growth under selective conditions and BrdU treatment.

As used herein an amplicon is the smallest repeated unit that contains heterologous DNA in the MACs provided herein. A megareplicon contains at least one amplicon, an inverted repeat thereof, and a megareplicator. A megareplicator is a primary replication initiation site.

As used herein, the minichromosome refers to a chromosome derived from a dicentric chromosome [see, e.g., FIG. 1] that contains more euchromatic than heterochromatic DNA.

As used herein, a megachromosome refers to a chromosome that, except for introduced heterologous DNA is substantially composed of heterochromatin. Megachromosomes are made of a tandem array of amplicons that contain two inverted megareplicons bordered by introduced heterologous DNA [see, e.g., FIG. 3 for a schematic drawing of a megachromosome]. For purposes herein, a megachromosome is about 50 to 400 Mb, generally about 250–400 Mb. Shorter variants, are also referred to as a truncated megachromosomes [about 90 to 120 or 150 Mb], dwarf megachromosomes [~150–200 Mb] and cell lines, and a micromegachromosome [~60–90 Mb]. For purposes herein, the term megachromosome refers to the overall repeated structure based on a tandem array of repeated chromosomal segments [amplicons] that contain two inverted megareplicons bordered by any inserted heterologous DNA. The size will be specified.

As used herein, genetic therapy involves the transfer of heterologous DNA to the certain cells, target cells, of an individual afflicted with a disorder for which such therapy is sought. The DNA is introduced into the selected target cells in a manner such that the heterologous DNA is expressed and a product encoded thereby is produced. Alternatively, the heterologous DNA may in some manner mediate expression of DNA that encodes the therapeutic product, it may encode a product, such as a peptide or RNA that in some manner mediates, directly or indirectly, expression of a therapeutic product. Genetic therapy may also be used to introduce therapeutic compounds, such as TNF, that are not normally produced in the host or that are not produced in therapeutically effective amounts or at a therapeutically useful time. The heterologous DNA encoding the therapeutic product may be modified prior to introduction into the cells of the afflicted host in order to enhance or otherwise alter the product or expression thereof.

As used herein, heterologous or foreign DNA and RNA are used interchangeably and refer to DNA or RNA that does not occur naturally as part of the genome in which it is present or which is found in a location or locations in the genome that differ from that in which it occurs in nature. It is DNA or RNA that is not endogenous to the cell and has been exogenously introduced into the cell. Examples of heterologous DNA include, but are not limited to, DNA that encodes a gene or gene(s) of interest, introduced for purposes of gene therapy or for production of the encoded protein. Other examples of heterologous DNA include, but are not limited to, DNA that encodes traceable marker proteins, such as a protein that confers drug resistance, DNA that encodes therapeutically effective substances, such as anti-cancer agents, enzymes and hormones, and DNA that encodes other types of proteins, such as antibodies. Antibodies that are encoded by heterologous DNA may be secreted or expressed on the surface of the cell in which the heterologous DNA has been introduced.

As used herein, a therapeutically effective product is a product that is encoded by heterologous DNA that, upon introduction of the DNA into a host, a product is expressed that effectively ameliorates or eliminates the symptoms, manifestations of an inherited or acquired disease or that cures said disease.

As used herein, transgenic plants refer to plants in which heterologous or foreign DNA is expressed or in which the expression of a gene naturally present in the plant has been altered.

As used herein, operative linkage of heterologous DNA to regulatory and effector sequences of nucleotides, such as promoters, enhancers, transcriptional and translational stop sites, and other signal sequences refers to the relationship between such DNA and such sequences of nucleotides. For example, operative linkage of heterologous DNA to a promoter refers to the physical relationship between the DNA and the promoter such that the transcription of such DNA is initiated from the promoter by an RNA polymerase that specifically recognizes, binds to and transcribes the DNA in reading frame.

As used herein, isolated, substantially pure DNA refers to DNA fragments purified according to standard techniques employed by those skilled in the art, such as that found in Maniatis et al. [(1982) *Molecular Cloning: A Laboratory Manual*, Cold Spring Harbor Laboratory Press, Cold Spring Harbor, N.Y.].

As used herein, expression refers to the process by which nucleic acid is transcribed into mRNA and translated into peptides, polypeptides, or proteins. If the nucleic acid is derived from genomic DNA, expression may, if an appropriate eukaryotic host cell or organism is selected, include splicing of the mRNA.

As used herein, vector or plasmid refers to discrete elements that are used to introduce heterologous DNA into cells for either expression of the heterologous DNA or for replication of the cloned heterologous DNA. Selection and use of such vectors and plasmids are well within the level of skill of the art.

As used herein, transformation/transfection refers to the process by which DNA or RNA is introduced into cells to for gene expression. Transfection refers to the taking up of an expression vector by a host cell whether or not any coding sequences are in fact expressed. Numerous methods of transfection are known to the ordinarily skilled artisan, for example, by direct uptake using calcium phosphate [CaPO4; see, e.g., Wigler et al. (1979) *Proc. Natl. Acad. Sci. U.S.A.* 76:1373–1376] and polyethylene glycol [PEG]-mediated DNA uptake and electroporation. Successful transfection is generally recognized when any indication of the operation of this vector occurs within the host cell. Transformation means introducing DNA into an organism so that the DNA is replicable, either as an extrachromosomal element or by chromosomal integrant.

As used herein, injected refers to the microinjection [use of a small syringe] of DNA into a cell.

As used herein, substantially homologous DNA refers to DNA that includes a sequence of nucleotides that is sufficiently similar to another such sequence to form stable hybrids under specified conditions.

It is well known to those of skill in this art, that nucleic acid fragments with different sequences may, under the same conditions, hybridize detectably to the same "target" nucleic acid. Two nucleic acid fragments hybridize detectably, under stringent conditions over a sufficiently long hybridization period, because one fragment contains a segment of at least about 14 nucleotides in a sequence which is complementary [or nearly complementary] to the sequence of at least one segment in the other nucleic acid fragment. If the time during which hybridization is allowed to occur is held constant, at a value during which, under preselected stringency conditions, two nucleic acid fragments with exactly complementary base-pairing segments hybridize detectably to each other, departures from exact complementarity can be introduced into the base-pairing segments, and base-pairing will nonetheless occur to an extent sufficient to make hybridization detectable. As the departure from complementarity between the base-pairing segments of two nucleic acids becomes larger, and as conditions of the hybridization become more stringent, the probability decreases that the two segments will hybridize detectably to each other.

Two single-stranded nucleic acid segments have "substantially the same sequence," within the meaning of the present specification, if (a) both form a base-paired duplex with the same segment, and (b) the melting temperatures of said two duplexes in a solution of 0.5×SSPE differ by less than 10° C. If the segments being compared have the same number of bases, then to have "substantially the same sequence", they will typically differ in their sequences at fewer than 1 base in 10. Methods for determining melting temperatures of nucleic acid duplexes are well known [see, e.g., Meinkoth and Wahl (1984) *Anal. Biochem.* 138:267–284 and references cited therein].

As used herein, a nucleic acid probe is a DNA or RNA fragment that includes a sufficient number of nucleotides to specifically hybridize to DNA or RNA that includes identical or closely related sequences of nucleotides. A probe may contain any number of nucleotides, from as few as about 10 and as many as hundreds of thousands of nucleotides. The conditions and protocols for such hybridization reactions are well known to those of skill in the art as are the effects of probe size, temperature, degree of mismatch, salt concentration and other parameters on the hybridization reaction. For example, the lower the temperature and higher the salt concentration at which the hybridization reaction is carried out, the greater the degree of mismatch that may be present in the hybrid molecules.

To be used as an hybridization probe, the nucleic acid is generally rendered detectable by labelling it, with a detectable moiety or label, such as $^{32}P$, $^{3}H$ and $^{14}C$, or by other means, including chemical labelling, such as by nick-translation in the presence of deoxyuridylate biotinylated at the 5'-position of the uracil moiety. The resulting probe includes the biotinylated uridylate in place of thymidylate residues and can be detected [via the biotin moieties] by any of a number of commercially available detection systems based on binding of streptavidin to the biotin. Such commercially available detection systems can be obtained, for example, from Enzo Biochemicals, Inc. [New York, N.Y.]. Any other label known to those of skill in the art, including non-radioactive labels, may be used as long as it renders the probes sufficiently detectable, which is a function of the sensitivity of the assay, the time available [for culturing cells, extracting DNA, and hybridization assays], the quantity of DNA or RNA available as a source of the probe, the particular label and the means used to detect the label.

Once sequences with a sufficiently high degree of homology to the probe are identified, they can readily be isolated by standard techniques, which are described, for example, by Maniatis et al. ((1982) *Molecular Cloning: A Laboratory Manual*, Cold Spring Harbor Laboratory Press, Cold Spring Harbor, N.Y.).

As used herein, conditions under which DNA molecules form stable hybrids and are considered substantially homologous are such that the DNA molecules with at least about 60% complementarity form stable hybrids. Such DNA fragments are herein considered to be "substantially homologous". For example, DNA that encodes a particular protein is substantially homologous to an other DNA fragment if the DNA forms stable hybrids such that the sequences of the fragments are at least about 60% complementary and if a protein encoded by the DNA retains its activity.

For purposes herein, the following stringency conditions are defined:

1) high stringency: 0.1×SSPE, 0.1% SDS, 65° C.
2) medium stringency: 0.2×SSPE, 0.1% SDS, 50° C.
3) low stringency: 1.0×SSPE, 0.1% SDS, 50° C.

or any combination of salt and temperature and other reagents that result in selection of the same degree of mismatch or matching.

As used herein, immunoprotective refers to the ability of a vaccine or exposure to an antigen or immunity-inducing agent to confer upon a host to whom the vaccine or antigen is administered or introduced the ability to resist infection by a disease causing pathogen or to have reduced symptoms. The selected antigen is typically an antigen that is presented by the pathogen.

As used herein, all assays and procedures, such as hybridization reactions and antibody-antigen reactions, unless otherwise specified, are conducted under conditions recognized by those of skill in the art as standard conditions.

A. Preparation of Cell Lines Containing MACs

The methods, cells and MACs provided herein are produced by virtue of the discovery of the existence of a higher-order replication unit [megareplicon] of the centromeric region. This megareplicon is delimited by a primary replication initiation site [megareplicator], and appears to facilitate replication of the centromeric heterochromatin, and most likely, centromeres. Integration of heterologous DNA into the megareplicator region or in close proximity thereto, initiates a large-scale amplification of megabase-size chromosomal segments, which leads to de novo chromosome formation.

Cell lines containing MACs can be prepared using cells, preferably a stable cell line, transforming it with a heterologous DNA fragment that encodes a selectable marker, culturing under selective conditions, and identifying cells that have a dicentric chromosome. These cells can then be manipulated as described herein to produce the minichromosomes and other MACs, particularly the heterochromatic SATACs as described herein.

Development of a dicentric chromosome appears to require integration of the heterologous DNA in the pericentric heterochromatin. Thus, the probability of incorporation can be increased by including DNA, such as satellite DNA, in the heterologous fragment that encodes the selectable marker. The resulting cell lines can then be treated as the exemplified cells herein to produce cell in which the dicentric chromosome has fragmented and to introduce additional selective markers into the dicentric chromosome, whereby amplification of the pericentric heterochromatin will produce the heterochromatic chromosomes. The following discussion is with reference to the EC3/7 line and use of resulting cells. The same procedures can be applied and to any other cells, particularly cell lines to prepare create SATACs and euchromatic minichromosomes.

1. Formation of De novo Chromosomes

De novo centromere formation in a transformed mouse LMTK-fibro-blast cell line [EC3/7] after cointegration of λ constructs [λCM8 and λgtWESneo] carrying human and bacterial DNA [Hadlaczky et al. (1991) Proc. Natl. Acad. Sci. U.S.A. 88:8106–8110 and U.S. application Ser. No. 08/375,271] has been shown. The integration of the "heterologous" human and phage DNA, and the subsequent amplification of mouse and heterologous DNA that led to the formation of a dicentric chromosome, occurred at the centromeric region of the short arm of a mouse chromosome. By G-banding this chromosome was identified as mouse chromosome 7. Because of the presence of two functionally active centromeres on the same chromosome, regular breakages occur between the centromeres. Such specific chromosome breakages gave rise to the appearance [in approximately 10% of the cells] of a chromosome fragment carrying the neo-centromere. From the EC3/7 cell line [see, U.S. Pat. No. 5,288,625, deposited at the European Collection of Animal cell Culture (hereinafter ECACC) under accession no. 90051001]; see, also Hadlaczky et al. (1991) Proc. Natl. Acad. Sci. U.S.A. 88:8106–8110, and U.S. application Ser. No. 08/375,271 and the corresponding published European application EP 0 473 253] carrying either the dicentric chromosome or a chromosome fragment with the neo-centromere, two sublines [EC3/7C5 and EC3/7C6] were selected by repeated single-cell cloning. In these cell lines, the neo-centromere was found exclusively on a minichromosome [neo-minichromosome]), while the formerly dicentric chromosome carried traces of "heterologous" DNA.

It has now been discovered that integration of DNA encoding a selectable marker in the heterochromatic region of the centromere led to formation of the dicentric chromosome.

2. The Neo-minichromosome

The chromosome breakage in the EC3/7 cells, which separates the neo-centromere from the mouse chromosome, occurred in the G-band positive "heterologous" DNA region. This is supported by the observation of traces of λ and human DNA sequences at the broken end of the formerly dicentric chromosome. Comparing the G-band pattern of the chromosome fragment carrying the neo-centromere with that of the stable neo-minichromosome, it is apparent that the neo-minichromosome is an inverted duplicate of the chromosome fragment that bears the neo-centromere. This is supported by the observation that although the neo-minichromosome carries only one functional centromere, both ends of the minichromosome are heterochromatic, and mouse satellite DNA sequences were found in these heterochromatic regions by in situ hybridization.

Mouse cells containing the minichromosome, which is composed of multiple repeats of the heterologous DNA, which in the exemplified embodiment is lambda DNA and neo DNA, can be used as recipient cells in cell transformation. Donor DNA, such as selected heterologous DNA linked to a second selectable marker, such as hygromycin resistance [hyg], can be introduced into the mouse cells and integrated into the minichromosomes by homologous recombination of lambda DNA in the donor DNA with that in the minichromosomes. Integration is verified by in situ hybridization and Southern blot analyses. Transcription and translation of the heterologous DNA is confirmed by primer extension and immunoblot analyses.

For example, DNA has been targeted into the λ-neo minichromosome in EC3/7C5 cells using a lambda DNA-containing construct [pNem1ruc] that also contains DNA encoding hygromycin resistance and the Renilla luciferase gene linked to a promoter, such as the cytomegalovirus [CMV] early promoter, and the bacterial neo encoding DNA. Integration of the donor DNA into the chromosome in selected cells [designated PHN4] was confirmed by nucleic acid amplification [PCR] and in situ hybridization. Events that would produce a neo-minichromosome are depicted in FIG. 1.

The resulting engineered minichromosome that contains the heterologous DNA can then transferred by cell fusion into a recipient cell line, such as Chinese hamster kidney cells [CHO] and correct expression of the heterologous DNA can be verified. Following production of the cells, metaphase chromosomes are obtained, such as by addition of colchicine, and the chromosomes purified by addition of AT and GC specific dyes on a dual laser beam based cell sorter. Preparative amounts of chromosomes [2–3 mls of $10^6$ chromosomes/ml] at a purity of 95% or higher can be obtained. The resulting chromosomes are used for delivery to cells by methods, such as microinjection, liposome packaged transfer.

Thus, the neo-minichromosome is stably maintained in cells, replicates autonomously, and permits the persistent long-term expression of neo gene under non-selective culture conditions. It also contains megabases of heterologous known DNA [lambda DNA in the exemplified embodiments] that serves as target sites form homologous recombination and integration of DNA of interest. The neo-minichromosome is, thus, a vector for genetic engineering of cells.

The methods herein provide means to induce the events that led to formation of the neo-minichromosome by introducing heterologous DNA with a selective marker [preferably a dominant selectable marker] and culturing under selective conditions. As a result, cells that contain a dicentric chromosome or fragments thereof produced by amplification, will be produced. Cells with the dicentric chromosome can then be treated to destabilize the genome with agents, such as BrdU and/or culturing under selective conditions, resulting in cells in which the dicentric chromosome has formed two chromosomes, a so-called minichromosome, and a formerly dicentric chromosome that has typically undergone amplification in the heterochromatin where the heterologous DNA has integrated to produce a generally a SATAC or a sausage chromosome [discussed below]. These cells can be fused with other cells to separate the minichromosome from the formerly dicentric chromosome into different cells so that each type of MAC can be manipulated separately.

3. Preparation of SATACs

Figure 2:
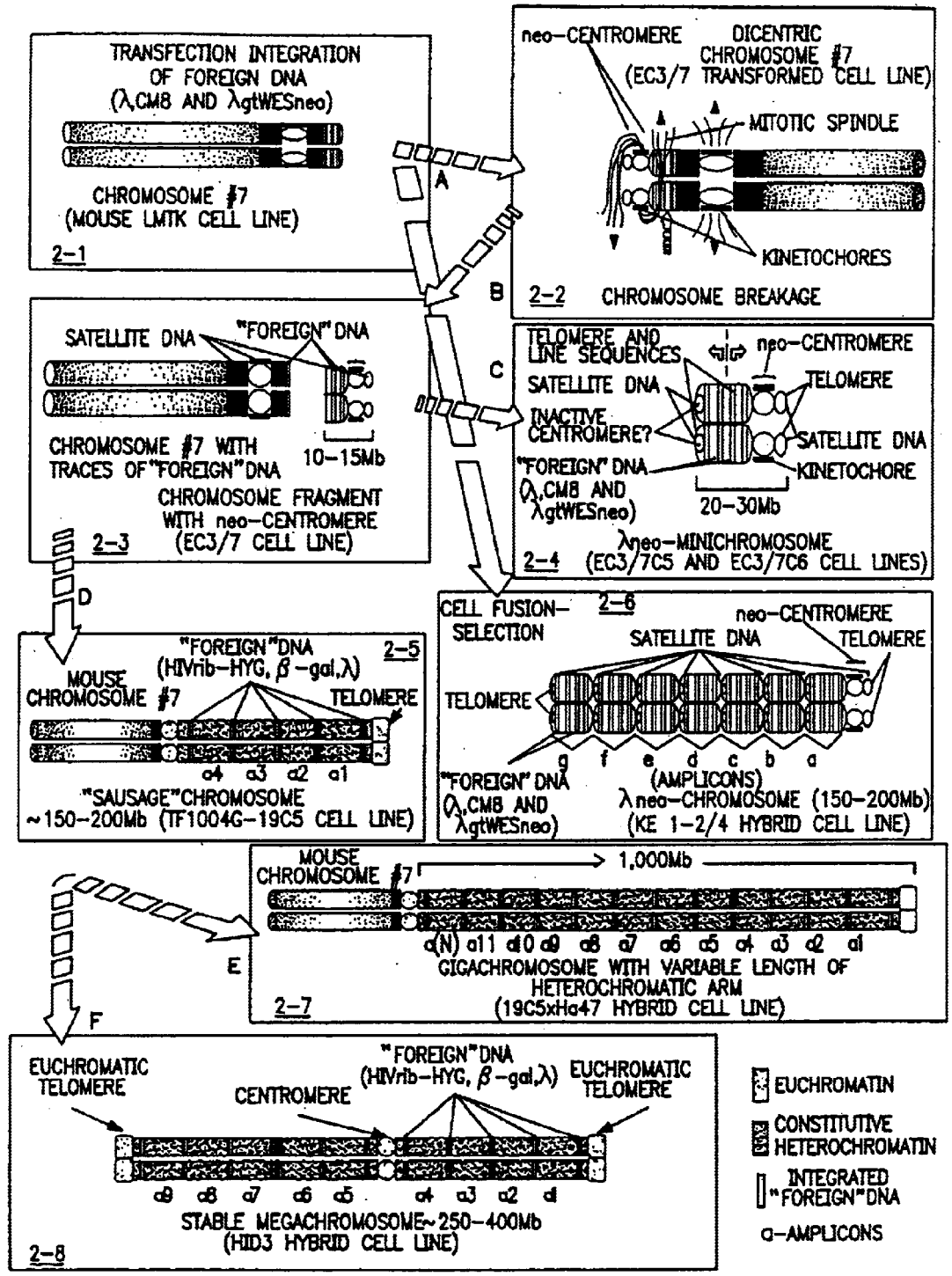
FIG. 2 shows a schematic summary of the manner in which the observed new chromosomes would form, and the relationships among the different de novo formed chromosomes. In particular, this figure shows a schematic drawing of the de novo chromosome formation initiated in the centromeric region of mouse chromosome 7. (A) A single E-type amplification in the centromeric region of chromosome 7 generates a neo-centromere linked to the integrated "foreign" DNA, and forms a dicentric chromosome (FIG. 2-1). Multiple E-type amplification forms the $\lambda$ neo-chromosome, which was derived from chromosome 7 and stabilized in a mouse-hamster hybrid cell line (FIGS. 2-2 and 2-6); (B) Specific breakage between the centromeres of a dicentric chromosome 7 generates a chromosome fragment with the neo-centromere, and a chromosome 7 with traces of heterologous DNA at the end (FIG. 2-3); (C) Inverted duplication of the fragment bearing the neo-centromere results in the formation of a stable neo-minichromosome (FIG. 2-4); (D) Integration of exogenous DNA into the heterologous DNA region of the formerly dicentric chromosome 7 initiates H-type amplification, and the formation of a heterochromatic arm. By capturing a euchromatic terminal segment, this new chromosome arm is stabilized in the form of the "sausage" chromosome (FIG. 2-5); (E) BrdU [5-bromodeoxyuridine], treatment and/or drug selection induce further H-type amplification, which results in the formation of an unstable gigachromosome (FIG. 2-7); (F) Repeated BrdU treatments and/or drug selection induce further H-type amplification including a centromere duplication, which leads to the formation of another heterochromatic chromosome arm. It is split off from the chromosome 7 by chromosome breakage, and by acquiring a terminal segment, the stable megachromosome is formed (FIG. 2-8).

An Exemplary protocol for preparation of SATACs is illustrated in FIG. 2 [particularly C, D and F] and FIG. 4 [see, also the EXAMPLES, particularly EXAMPLES 4–7].

To prepare a SATAC, the starting materials are a cell, preferably a stable cell line, such as a fibroblast cell line, and a DNA fragment that includes DNA that encodes a selective marker. To insure integration of the DNA fragment in the heterochromatin, it is preferable to start with DNA that will be targeted to the pericentric heterochromatic region of the chromosome, such as λCM8 and vectors provided herein, such as pTEMPUD [FIG. 5] that include satellite DNA. After introduction of the DNA, the cells are grown under selective conditions. The resulting cells are examined and any that have dicentric chromosomes [or heterochromatic chromosomes or sausage chromosomes or other such structure [see, FIGS. 2C, 2D, 2E and 2F] are selected.

In particular, if a cell with a dicentric chromosome is selected, it can be grown under selective conditions, or, preferably, additional DNA encoding a second selectable marker is introduced, and the cells grown under conditions selective for the second marker. The resulting cells should include chromosomes that have structures similar to those depicted in FIGS. 2D, 2E, 2F. Cells with a structure, such as the sausage chromosome, FIG. 2D, can be selected and fused with a second cell line to eliminate other chromosomes that are not of interest. If desired cells with other chromosomes can be selected and treated as described herein. If a cell with a sausage chromosome is selected, it is treated with an agent, such as BrdU, that destabilizes the chromosome so that the heterochromatic arm forms a chromosome that is substantially heterochromatin [megachromosome, see, FIG. 2F]. Structures such as the gigachromsome in which the heterochromatic arm has amplified but not broken off from the euchromatic arm, will also be observed. The megachromosome is a stable chromosome. Further manipulation, such as fusions and growth in selective conditions and/or BrdU treatment or other such treatment, can lead to fragmentation of the megachromosome to form smaller chromosomes that have the amplicon as the basic repeating unit.

Figure 5:
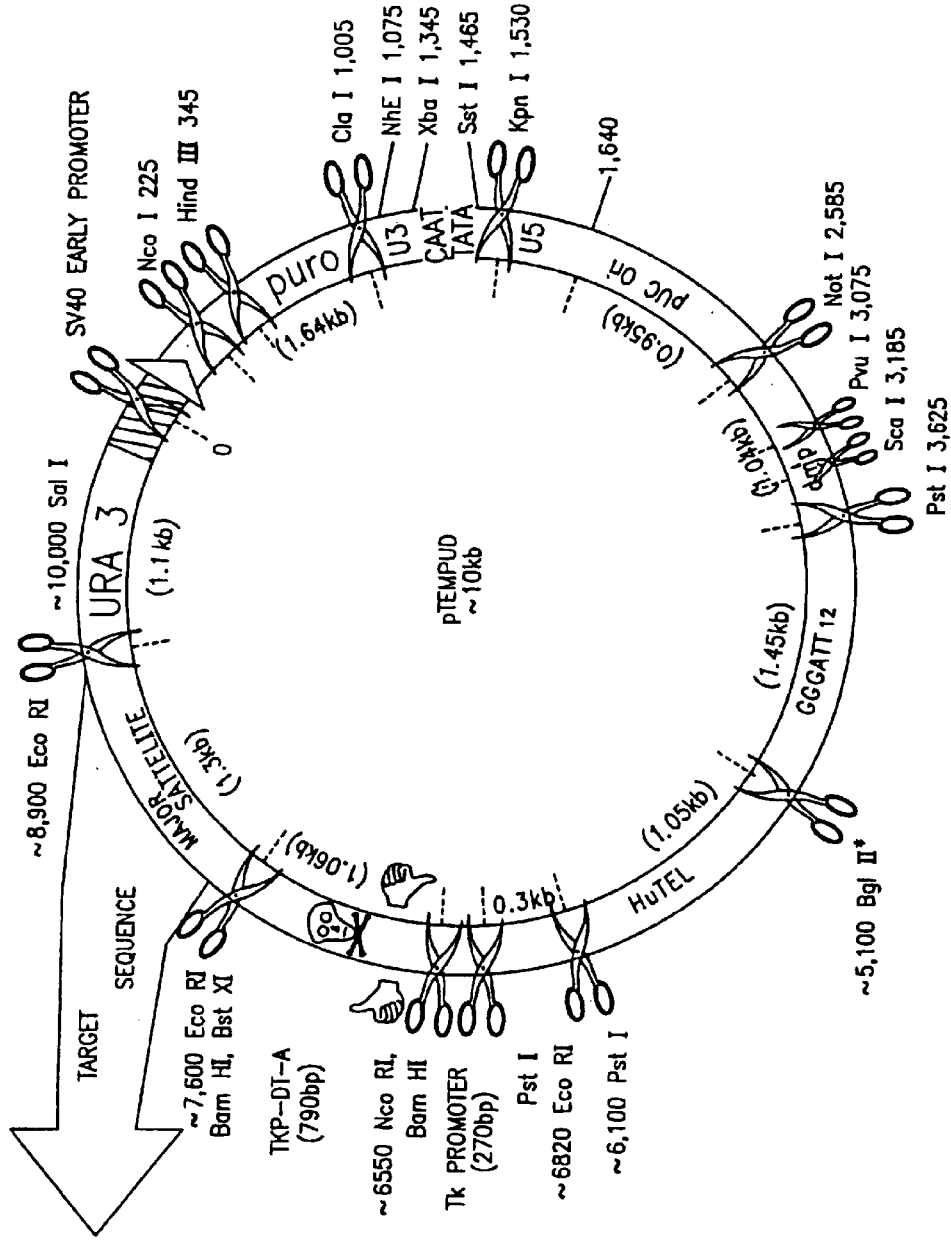
FIG. 5 is diagram of the plasmid pTEMPUD.

The megachromosome can be further fragmented in vivo using a chromosome fragmentation vector, such as pTEMPUD [see, FIG. 5 and EXAMPLE 12] to ultimately produce a chromosome that comprises the smallest stable replicable unit, about 15 Mb–50 Mb, containing two to four megareplicons.

Thus, The stable chromosomes formed de novo that originate from the short arm of mouse chromosome 7 have been analyzed. This chromosome region shows a capacity for amplification of large chromosome segments, and promotes de novo chromosome formation. Large-scale amplification at the same chromosome region leads to the formation of dicentric and multicentric chromosomes, a minichromosome, the 150–200 Mb size λ neo-chromosome, the "sausage" chromosome, the 500–1000 Mb gigachromosome, and the stable 250–400 Mb megachromosome.

A clear segmentation is observed along the arms of the megachromosome, and analyses show that the building units of this chromosome are amplicons of ~30 Mb composed of mouse major satellite DNA with the integrated "foreign" DNA sequences at both ends. The ~30 Mb amplicons are composed of two ~15 Mb inverted doublets of ~7.5 Mb mouse major satellite DNA blocks, which are separated from each other by a narrow band of non-satellite sequences [see, e.g., FIG. 3]. The wider non-satellite regions at the amplicon borders contain integrated, exogenous [heterologous] DNA, while the narrow bands of non-satellite DNA sequences within the amplicons are integral parts of the pericentric heterochromatin of mouse chromosomes. These results indicate that the ~7.5 Mb blocks flanked by non-satellite DNA are the building units of the pericentric heterochromatin of mouse chromosomes, and the ~15 Mb size pericentric regions of mouse chromosomes contain two ~7.5 Mb units.

Apart from the euchromatic terminal segments, the whole megachromosome is heterochromatic, and has structural homogeneity. Therefore, this large chromosome offers a unique possibility for obtaining information about the amplification process, and for analyzing some basic characteristics of the pericentric constitutive heterochromatin, as vector for heterologous DNA, and as target for further fragmentation.

As shown herein, this phenomenon is generalizable and can be observed with other chromosomes. Also, although these de novo formed chromosome segments and chromosomes appear different, there are, similarities that indicate that a similar amplification mechanism plays a role in their formation: (i) in each case, the amplification is initiated in the centromeric region of the mouse chromosomes and large (Mb size) amplicons are formed; (ii) mouse major satellite DNA sequences are constant constituents of the amplicons, either by providing the bulk of the heterochromatic amplicons [H-type amplification], or by bordering the euchromatic amplicons [E-type amplification]; (iii) formation of inverted segments can be demonstrated in the λ neo-chromosome and megachromosome; (iv) chromosome arms and chromosomes formed by the amplification are stable and functional.

The presence of inverted chromosome segments seems to be a common phenomenon in the chromosomes formed de novo at the centromeric region of mouse chromosome 7. During the formation of the neo-minichromosome, the event leading to the stabilization of the distal segment of mouse chromosome 7 that bears the neo-centromere may have been the formation of its inverted duplicate. Amplicons of the megachromosome are inverted doublets of ~7.5 Mb mouse major satellite DNA blocks.

4. Cell Lines

Cell lines that contain MACs, such as the minichromosome, the λ-neo chromosome, and the SATACs are provided herein or can be produced by the methods herein. Such cell lines provide a convenient source of these chromosomes and can be manipulated, such as by cell fusion or production of microcells for fusion with selected cell lines, to deliver the chromosome of interest into hybrid cell lines. Exemplary cell lines are described herein and some have been deposited with the ECACC.

a. EC3/7C5 and EC3/7C6

Two cell lines EC3/7C5 and EC3/7C6 produced by single cell cloning of EC3/7 were examined. For exemplary purposes EC3/7C5 has been deposited with the ECACC. These cell lines contain a minichromosome and the formerly dicentric chromosome from EC3/7. The stable minichromosomes in cell lines [EC3/7C5 and EC3/7C6] appear to be virtually identical and they seem to be a duplicated derivatives of the ~10–15 Mb "broken-off" fragment of the dicentric chromosome. Their identical size in these independently generated cell lines might indicate that ~20–30 Mb is the minimal or close to the minimal physical size for a stable minichromosome.

b. TF1004G/19

Introduction of additional heterologous DNA, including a second selectable marker hygromycin and also a detectable marker, β-galactosidase, into the EC3/7C5 cell line and growth under selective conditions produced cells designated TF1004G/19. In particular, this cell line was produced from the EC3/7C5 cell line by cotransfection with plasmids pH132, which contains an anti-HIV ribozyme, and hygromycin resistance gene, pCH110 [encodes β-galactosidase] and λ phage [λcl 875 Sam 7] DNA and selection with hygromycin B.

Detailed analysis of TF1004G/19 cell line by in situ hybridization with lambda phage and plasmid DNA sequences revealed the formation of the sausage chromosome. The formerly dicentric chromosome of EC3/7C5 cell translocated to the end of another acrocentric chromosome. The heterologous DNA integrated into the pericentric heterochromatin of formerly dicentric chromosome and is amplified several times with megabases of mouse pericentric heterochromatic satellite DNA sequences [FIG. 2D]) forming the "sausage" chromosome. Subsequently the acrocentric mouse chromosome was substituted by a euchromatic telomere.

In situ hybridization with biotin labeled subfragments of the hygromycin resistance and β-galactosidase genes resulted in hybridization signal only in the heterochromatic arm of the sausage chromosome, indicating that in TF1004G/19 transformant cells these genes are localized in the pericentric heterochromatin. A high level of gene expression, however, was detected.

In general, heterochromatin has a silencing effect in Drosophila, yeast and on the HSV-tk gene introduced into satellite DNA at mouse centromere. Thus, it was of interest to study the TF1004G/19 transformant cell line in to confirm that gene expression [of the β-gal] was indeed localized in the heterochromatin contrary to recognized dogma.

For this purpose, subclones of TF1004G/19 containing a different a sausage chromosome [see FIG. 2D] by single cell cloning were established. Southern DNA hybridization with subfragments of hygromycin resistance and β-galactosidase genes showed close correlation to the intensity of hybridization and the length of sausage chromosome. This finding supports the conclusion that these genes are localized in the heterochromatic arm of the sausage chromosome.

(1) TF1004G-19C5

TF1004G-19C5 is a mouse LMTK⁻ fibroblast cell line containing neo-minchromosomes and stable "sausage" chromosomes. It is a subclone of TF1004G/19. It has been deposited as an exemplary cell line and exemplary source of a sausage chromosome. Subsequent fusion of this cell line with CHO K2O cells and selection with hygromycin and hat resulted in hybrid cells that carry the sausage chromosome and/or the neo-minichromosome. BrdU treatment, single cell cloning and selection with G418 and/or hygromycin produced various cells that carry chromosomes of interest, including G3D5.

(2) Other Subdlones

G3D5, which has been deposited is a mouse hamster hybrid cell line that carries the neo-minichromosome and the megachromosome. H1D3 is a subclone thereof that carries the megachromosome. Fusion of this cell line with the CD4⁺ Hela cell line and also DNA encoding an additional selection gene, neo, produced cells that carry the megachromosome as well as a human chromosome that carries CD4neo [H1D3 cells]. Further BrdU treatment and single cell cloning produced cell lines, such as 1B3 that include cells with a truncated megachromosome.

5. DNA Constructs used to Transform the Cells

Heterologous DNA can be introduced into the cells by transfection or other suitable method at any stage during preparation of the chromosomes [see, e.g., FIG. 4]. In general integration of such DNA is assured by relying on site directed integration, such as by inclusion of λ-DNA for the exemplified chromosomes and also an additional selective marker gene. For example, cells with a MAC, such as the minichromosome or a SATAC can be cotransfected with a plasmid encoding the desired heterologous DNA, such as HIV ribozyme, cystic fibrosis gene, and a second selectable marker, such as hygromycin resistance. Selection is effected with the agent that selects for the new selectable marker cells containing chromosomes that include the DNA in the MAC are identified. Fusion with a second cell line can provide a means to produce cell lines that contain one particular type of chromosomal structure or MAC.

Various vectors for this purpose are provided herein [see, Examples] and others can be readily constructed. The vectors should include DNA that will target the DNA to the MAC, a selectable marker and the selected heterologous gene of interest. Based on the disclosure herein and the knowledge of the skilled artisan, one of skill can construct such vectors.

Of particular interest herein is the vector pTEMPUD and derivatives thereof that can target DNA into the heterochromatic region of selected chromosomes. These vectors can also serve as fragmentation vectors [see, e.g., Example 12].

Heterologous genes of interest include any gene that encodes a therapeutic gene and DNA encoding gene products of interest. These genes and DNA include, but are not limited to: the cystic fibrosis gene [CF] cystic fibrosis transmembrane regulator (CFTR) [see, e.g., U.S. Pat. No. 5,240,846; Rosenfeld et al. (1992) *Cell* 68:143–155; Hyde et al. (1993) *Nature* 362: 250–255; Kerem et al. (1989) *Science* 245:1073–1080; Riordan et al. (1989) *Science* 245:1066–1072; Rommens et al. (1989) *Science* 245:1059–1065; Osborne et al. (1991) *Am. J. Hum. Genetics*

48:6089–6122; White et al. (1990) *Nature* 344:665–667; Dean et al. (1990) *Cell* 61:863–870; Erlich et al. (1991) *Science* 252:1643; and U.S. Pat. Nos. 5,453,357, 5,449,604, 5,434,086, and 5,240,846, which provides a retroviral vector encoding the normal CFTR gene].

B. Isolation of Artificial Chromosomes

The MACs provided herein can be isolated by any suitable method known to those of skill in the art. Also, a method is provided herein for effecting substantial purification. SATACs have been isolated by fluorescence activated cell sorting [FACS]. This method takes advantage of the nucleotide base content of the SATACs, which by virtue of their heterochromatic content will differ from any other chromosomes in a cell. In particular, metaphase chromosomes are isolated and stained with base specific dyes, such as Hoechst 33258 and chromocycin A3. Fluorescence ctivated cell sorting will separate the SATACs from the genomic chromosomes. A dual-laser cell sorter [FACStar Plus and FAXStar Vantage Becton Dickinson Immunocytometry System] in which two lasers were set to excite the dyes separately, allowed a bivariate analysis of the chromosomes by size and base-pair composition. Cells containing such SATACs can be similarly sorted.

C. Introduction of Artificial Chromosomes into Cells, Tissues, Animals and Plants Suitable hosts for introduction of the MACs provided herein, include but are not limited to any animal or plant, cell or tissue thereof, including, but not limited to: mammals, birds, reptiles, amphibians, insects, fish, arachnids, tobacco, tomato, wheat, monocots, dicots and algae. The MACs may be introduced by cell fusion or microcell fusion or subsequent to isolation by any method known to those of skill in this art, including but not limited to: direct DNA transfer, electroporation, lipofection, liposomes, microprojectile bombardment, microinjection and any other suitable method.

Other methods for introducing DNA into cells, include nuclear microinjection, electroporation, bacterial protoplast fusion with intact cells. Polycations, such as polybrene and polyornithine, may also be used. For various techniques for transforming mammalian cells, see e.g., Keown et al. *Methods in Enzymology* (1990) Vol.185, pp. 527–537; and Mansour et al. (1988) *Nature* 336:348–352.

DNA may be introduced by direct DNA transformation; microinjection in cells or embryos, protoplast regeneration for plants, electroporation, microprojectile gun and other such methods [see, e.g., Weissbach et al. (1988) Methods for Plant Molecular Biology, Academic Press, N.Y., Section VIII, pp. 421–463; Grierson et al. (1988) Plant Molecular Biology, 2d Ed., Blackie, London, Ch. 7–9; see, also U.S. Pat. Nos. 5,491,075; 5,482,928; and 5,424,409; see, also, e.g., U.S. Pat. No. 5,470,708, which describes particle-mediated transformation of mammalian unattached cells].

For example, isolated purified artificial chromosomes can be injected into an embryonic cell line such as a human kidney primary embryonic cell line [ATCC CRL 1573] or embryonic stem cells [see, e.g., Hogan et al. (1994) *Manipulating the Mouse Embryo, A :Laboratory Manual*, Cold Spring Harbor Laboratory Press, Cold Spring Harbor, N.Y., see, especially, pages 255–264 and Appendix 3]. Preferably the chromosomes are introduced by microinjection, using a system such as the Eppendorf automated microinjection system, and grown under selective conditions, such as hygromycin B or neomycin resistance.

1. Methods for Introduction of Chromosomes into Hosts

Depending on the host cell used, transformation is done using standard techniques appropriate to such cells. These methods include any, including those described herein, known to those of skill in the art.

a. DNA uptake

For mammalian cells without such cell walls, the calcium phosphate precipitation method [see, e.g., Graham et al. (1978) *Virology* 52:456–457 is often preferred. DNA uptake can be accomplished by DNA alone or in the presence of polyethylene glycol [PEG-mediated gene transfer], which is a fusion agent, with plant protoplasts or by any variations of such methods known to those of skill in the art [see, et al. U.S. Pat. No. 4,684,611].

A commonly used approach for gene transfer in land plants involves the direct introduction of purified DNA into protoplasts. The three basic methods for direct gene transfer include: 1) polyethylene glycol [PEG]-mediated DNA uptake, 2) electroporation -mediated DNA uptake and 3) microinjection. In addition, plants may be transformed using ultrasound treatment [see, e.g., International PCT application No. WO 91/00358].

b. Electroporation

Electroporation, which involves providing high-voltage electrical pulses to a solution containing a mixture of protoplasts and foreign DNA to create reversible pores in the membranes of plant protoplasts as well as other cells. Electroporation is generally used for prokaryotes or other cells, such as plants that contain substantial cell-wall barriers. Methods for effecting electroporation are well known [see, e.g., U.S. Pat. Nos. 4,784,737, 5,501,967, 5,501,662, 5,019,034, 5,503,999; see, also Fromm et al. (1985) *Proc. Natl. Acad. Sci. U.S.A.* 82:5824–5828].

For example, electroporation is often used for transformation of plants [see, e.g., Ag Biotechnology News, Vol. 7 p. 3 and 17 (September/October 1990)]. In this technique, plant protoplasts are electroporated in the presence of the DNA of interest that also includes a phenotypic marker. Electrical impulses of high field strength reversibly permeabilize biomembranes allowing the introduction of the plasmids. Electroporated plant protoplasts reform the cell wall, divide, and form plant callus. Transformed plant cells will be identified by virtue of the expressed phenotypic marker. The exogenous DNA may be added to the protoplasts in any form such as, for example, naked linear, circular or supercoiled DNA, DNA encapsulated in liposomes, DNA in spheroplasts, DNA in other plant protoplasts, DNA complexed with salts, and other methods.

c. Microcells

The chromosomes can be transferred by preparing microcells containing an artificial chromosome and then fusing with selected target cells. Methods for such preparation and fusion or microcells are well known [see, e.g., U.S. Pat. Nos. 5,240,840, 4,806,476, 5,298,429, Fournier (1981) *Proc. Natl. Acad. Sci. U.S.A.* 78:6349–6353; and Lambert et al. (1991) *Proc. Natl. Acad. Sci. U.S.A.* 88:5907–59].

2. Hosts

Suitable host include any host known to be useful for introduction and expression of heterologous DNA. Of particular interest herein, animal and plant cells and tissues, including, but not limited to insect cells and larvae, plants, and animals, particularly transgenic animals, and animal cells. Other hosts include, but are not limited to mammals, birds, reptiles, amphibians, insects, fish, arachnids, tobacco, tomato, wheat, monocots, dicots and algae, and any host into which introduction of heterologous DNA is desired. Such introduction can be effected using the MACs provided herein, or, if necessary by using the MACs provided herein to identify species-specific centromeres and/or functional chromosomal units and then using the resulting centromeres or chromosomal units as artificial chromosomes, or alternatively, using the methods exemplified herein for production of MACs to produce species-specific artificial chromosomes.

a. Introduction of DNA into Embryos for Production of Transgenic Animals and Introduction of DNA into Animal Cells Transgenic animals can be produced by introducing exogenous genetic material into a pronucleus of a mammalian zygote by microinjection [see, e.g., U.S. Pat. Nos. 4,873,191 and 5,354,674; see, also, International PCT application No. WO95/14769, which is based on U.S. application Ser. No. 08/159,084]. The zygote is capable of development into a mammal. The embryo or zygote is transplanted into a host female uterus and allowed to develop. Detailed protocols and examples are set forth below.

DNA can be introduced into animal cells using any known procedure, including, but not limited to: direct uptake, incubation with polyethylene glycol [PEG], microinjection, electroporation, lipofection, cell fusion, microcell fusion, particle bombardment, including microprojectile bombardment [see, e.g., U.S. Pat. No. 5,470,708, which provides a method for transforming unattached mammalian cells via particle bombardment], and any other such method. For example, the transfer of plasmid DNA in liposomes directly to human cells in situ has been approved by the FDA for use in humans [see, e.g., Nabel, et al. (1990) *Science* 249:1285–1288 and U.S. Pat. No. 5,461,032].

b. Introduction of Heterologous DNA into Plants.

Numerous methods for producing or developing transgenic plants are available to those of skill in the art. The method used is primarily a function of the species of plant. These methods include, but are not limited to: direct transfer of DNA by processes, such as PEG-induced DNA uptake, protoplast fusion, microinjection, electroporation, and microprojectile bombardment [see, e.g., Uchimiya et al. (1989) *J. of Biotech.* 12: 1–20 for a review of such procedures, see, also, e.g., U.S. Pat. Nos. 5,436,392 and 5,489,520 and many others]. For purposes herein, when introducing a MAC, microinjection and protoplast fusion are preferred Plant species, including tobacco, rice, maize, rye, soybean, *Brassica napus,* cotton, lettuce, potato and tomato, have been used to produce transgenic plants. Tobacco and other species, such as petunias, often serve as experimental models in which the methods have been developed and the genes first introduced and expressed.

DNA uptake can be accomplished by DNA alone or in the presence of PEG, which is a fusion agent, with plant protoplasts or by any variations of such methods known to those of skill in the art [see, e.g., U.S. Pat. No. 4,684,611 to Schilperoot et al.]. Electroporation, which involves high-voltage electrical pulses to a solution containing a mixture of protoplasts and foreign DNA to create reversible pores, has been used, for example, to successfully introduce foreign genes into rice and *Brassica napus.* Microinjection of DNA into plant cells, including cultured cells and cells in intact plant organs and embryoids in tissue culture and microprojectile bombardment [acceleration of small high density particles, which contain the DNA, to high velocity with a particle gun apparatus, which forces the particles to penetrate plant cell walls and membranes] have also been used. All plant cells into which DNA can be introduced and that can be regenerated from the transformed cells can be used to produce transformed whole plants which contain the transferred chromosome. The particular protocol and means for introduction of the DNA into the plant host may need to be adapted or refined to suit the particular plant species or cultivar. c.

Insect Cells

Insects are useful hosts for introduction of artificial chromosomes for numerous reasons, including, but not limited to: (a) amplification of genes encoding useful proteins can be accomplished in the artificial mammalian chromosome to obtain higher protein yields in insect cells; (b) insect cells support required post translational modifications, such as glycosylation and phosphorylation, that can be required for protein biological functioning; (c) insect cells do not support mammalian viruses, and, thus, eliminate the problem of cross-contamination of products with such infectious agents; (d) this technology circumvents traditional recombinant baculovirus systems for production of nutritional, industrial or medicinal proteins in insect cell systems; (e) the low temperature optimum for insect cell growth (28° C.) permits reduced energy cost of production; (f) serum free growth medium for insect cells permits lower production costs; (g) artificial chromosome-containing cells can be stored indefinitely at low temperature; and (h) insect larvae will be biological factories for production of nutritional, medicinal or industrial proteins by microinjection of fertilized insect eggs [see, e.g., Joy et al. (1991) *Current Science* 66:145–150, which provides a method for microinjecting heterologous DNA into *Bombyx mori* eggs].

Either MACs or insect-specific [BUGACs] will used to introduce genes into insects. As described in the Examples, it appears that MACs will function in insects to direct expression of heterologous DNA contained thereon.

Insect host cells include, but are not limited to, hosts such as *Spodoptera frugiperda* [caterpillar], *Aedes aegypti* [mosquito], *Aedes albopictus* [mosquito], *Drosphila melanogaster* [fruitfly], *Bombyx mori* [silkworm] and *Trichoplusia ni* [cabbage looper]. Effort haves been directed toward propagation of insect cells in culture. Such efforts have focused on the fall armyworm, Spodoptera frugiperda. The cell lines have been developed also from other insects such as the cabbage looper, trichoplusia ni and the silkworm, *Bombyx mori.* It has also been suggested that analogous cell lines can be created using the tobacco hornworm, or Manduca sexta. To introduce DNA into an insect, it should be introduced into the larvae, and allowed to proliferate, and then the hemolymph recovered from the larvae so that the proteins can be isolated therefrom. The preferred method herein is microinjection [see, e.g., Tamura et al. (1991) *Bio Ind.* 8:26–31; Nikolaev et al. (1989) *Mol. Biol.* (Moscow) 23:1177–87; and methods exemplified and discussed herein].

D. Applications for and Uses of Artificial Chromosomes

Artificial chromosomes provide convenient and useful vectors, and in some instances the only vectors for introduction of heterologous genes into hosts. Virtually any gene of interest is amenable to introduction into a host via an artificial chromosomes. Such genes include, but are not limited to genes that encode receptors, cytokines, enzymes, proteases, hormones, growth factors, tumor suppressor genes, therapeutic products and multigene pathways.

The artificial chromosomes provided herein will be used in methods of protein and gene product production, particularly using insects as host cells for production of such products. They are also intended for use in methods of gene therapy, and in for production of transgenic plants and animals [discussed above, below and in the EXAMPLES].

1. Gene Therapy

Any therapeutic gene product or product of a multigene pathway may be introduced into a host animal, such as a human, or into a target cell line for introduction into an animal, for therapeutic purposes. Such therapeutic purposes include, genetic therapy to cure or to provide gene products that are missing or defective, to deliver agents, such as anti-tumor agents, to targeted cells or to an animal, and to provide gene products that will confer resistance or reduce susceptibility to a pathogen or ameliorate symptoms of a disease or disorder. The following are some exemplary genes and gene products. Such exemplification is not intended to be limiting.

a. Anti-HIV Ribozymes

As exemplified below, DNA encoding anti-HIV ribozymes can be introduced and expressed using MACs, including the euchromatin-based minichromosomes and the SATACs. These MACs can be used to make a transgenic mouse with that express a ribozyme and, thus, serve as a model for testing the activity of such ribozymes or from which ribozyme-producing cell lines can be made. Also, introduction of a MAC into human cells that encodes an anti-HIV ribozyme will serve as treatment for HIV infection.

b. Tumor Suppressor Genes

Tumor suppressor genes are genes that, in their wild-type alleles, express proteins that suppress abnormal cellular proliferation. When the gene coding for a tumor suppressor protein is mutated or deleted, the resulting mutant protein or the complete lack of tumor suppressor protein expression may fail to correctly regulate cellular proliferation, and abnormal cellular proliferation may take place, particularly if there is already existing damage to the cellular regulatory mechanism. A number of well-studied human tumors and tumor cell lines have been shown to have missing or nonfunctional tumor suppressor genes.

Examples of tumor suppression genes include, but are not limited to, the retinoblastoma susceptibility gene or RB gene, the p53 gene, the deleted in colon carcinoma [DCC] gene and the neurofibromatosis type 1 [NF-1] tumor suppressor gene [see, e.g., U.S. Pat. No. 5,496,731; Weinberg et al. (1991) 254:1138–1146]. Loss of function or inactivation of tumor suppressor genes may play a central role in the initiation and/or progression of a significant number of human cancers.

The p53 Gene

Somatic cell mutations of the p53 gene are said to be the most frequently mutated gene in human cancer [see, e.g., Weinberg et al. (1991) Science 254:1138–1146]. The normal or wild-type p53 gene is a negative regulator of cell growth, which, when damaged, favors cell transformation. The p53 expression product is found in the nucleus, where it may act in parallel with or cooperatively with other gene products. Tumor cell lines in which p53 has been deleted have been successfully treated with wild-type p53 vector to reduce tumorigenicity [see, Baker et al. (1990) Science 249:912–915].

DNA encoding the p53 gene and plasmids containing this DNA are well known [see, e.g., U.S. Pat. No. 5,260,191; see, also Chen et al. (1990) Science 250:1576; Farrel et al. (1991) EMBO J. 10:2879–2887, plasmids containing the gene are available from the ATCC, and the sequence is in the GenBank Database, accession nos. X54156, X60020, M14695, M16494, K03199].

c. The CFTR gene

Cystic fibrosis [CF] is an autosomal recessive disease that affects epithelia of the airways, sweat glands, pancreas, and other organs. It is a lethal genetic disease associated with a defect in Cl transport, and is caused by mutations in the gene coding for cystic fibrosis transmembrane conductance regulator [CFTR], a 1480 amino acid protein that has been associated with the expression of chloride conductance in a variety of eukaryotic cell types. Defects in CFTR destroy or reduce the ability of epithelial cells in the airways, sweat glands, pancreas and other tissues to secret Cl in response to cAMP-mediated agonists and impair activation of apical membrane channels by cAMP-dependent protein kinase A [PKA]. Given the high incidence and devastating nature of this disease, development of effective CF treatments is imperative.

The CFTR gene [~600 kb] can be transferred, such as from a CF-YAC [see Green et al. Science 250:94–98] by construction of a selectable CF YAC by inserting a selectable marker, such as puromycin or hygromycin resistance and λ-DNA by site specific integration into the neo-minichromosome or into a SATAC. The CF-YAC can be introduced into cells, such as EC3/7C5 or 19C5xHa4 by yeast protoplast fusion or microinjection of yeast nuclei into mammalian cells, select stable transformants, and establish antibiotic-resistant cell lines.

2. Disease Resistant Animals and Plants

Artificial chromosomes are ideally suited for preparing disease resistant animals, including vertebrates and invertebrates, including fish as well as mammals. In particular, multivalent vaccines can be prepared. Such vaccines will be encoded by multiple antigens that can be included in a MAC and either delivered to a host to induce immunity, or incorporated into embryos to produce disease-resistant animals and plants [or plants and animals that are less susceptible].

Fish and crustaceans will serve as model hosts for production of disease resistant animals.

3. Use of MACs and Other Artificial Chromosomes for Preparation of and Screening of Libraries Since large fragments can incorporated into each SATAC, entire genomes can be readily screened. For example, DNA encoding tree growth factors can be introduced into trees. Libraries can be prepared, introduce large fragments into chromosomes, and introduce them all into trees, thereby insuring expression.

The following examples are included for illustrative purposes only and are not intended to limit the scope of the invention.

EXAMPLE 1

General Materials and Methods

The following materials and methods are exemplary of methods that are used in the following Examples and that can be used to pre. Other suitable materials and methods known to those of skill in the art may used. Modifications of these materials methods known to those of skill in the art may also be employed.

A. Culture of cell lines, cell fusion, and transfection of cells

1. Chinese hamster K20 cells and mouse A9 fibroblast cells were cultured in F-12 medium. EC3/7 [see, U.S. Pat. No. 5,288,625, and deposited at the European Collection of Animal cell Culture (ECACC) under accession no. 90051001; see, also Hadlaczky et al. (1991) Proc. Natl. Acad. Sci. U.S.A. 88:8106–8110 and U.S. application Ser. No. 08/375,271] and EC3/7C5 [see, U.S. Pat. No. 5,288,625 and Praznovszky et al. (1991) Proc. Natl. Acad. Sci. U.S.A. 88:11042–11046] mouse cell lines, and the KE1-2/4 hybrid cell line were maintained in F-12 medium containing 400 µg/ml G-418 [SIGMA, St. Louis, Mo.].

2. TF1004G19 and TF1004G19C5 mouse cells, described below, and the 19xHa4 hybrid, described below, and its sublines were cultured in F-12 medium containing 400 µg/ml Hygromycin B [Calbiochem]. LP11 cells were maintained in F-12 medium containing 3–15 µg/ml Puromycin [SIGMA, St. Louis, Mo.].

3. Cotransfection of EC3/7C5 cells with plasmids [pH132, pCH110 available from Pharmacia, see, also Hall et al. (1983) *J. Mol. Appl. Gen.* 2:101–109] and with λDNA was made using the calcium phosphate DNA precipitation method [see, e.g., Chen et al. (1987) *Mol. Cell. Biol.* 7:2745–2752], using 2–5 µg plasmid DNA and 20 µg λ phage DNA per 5×10$^6$ recipient cells.

4. Cell Fusion

Mouse and hamster cells were fused using polyethylene glycol [Davidson et al. (1976) *Som. Cell Genet.* 2:165–176). Hybrid cells were selected in HAT medium containing 400 µg/ml Hygromycin B.

Approximately 2×10$^7$ recipient and 2×10$^6$ donor cells were fused using polyethylene glycol [Davidson et al. (1976) *Som. Cell Genet.* 2:165–176]. Hybrids were selected and maintained in F-12/HAT medium [Szybalsky et al. (1962) *Natl. Cancer Inst. Monogr.* 7:75–89] containing 10% FCS and 400 µg/ml G418. The presence of "parental" chromosomes in the hybrids cell lines was verified by in situ hybridizations with species-specific probes using biotin labeled human and hamster genomic DNA, and a mouse long interspersed repetitive DNA [pMCPE1.51].

5. Microcell Fusion

Microcell-mediated chromosome transfer was done according to Saxon et al. [(1985) *Mol. Cell. Biol.* 1:140–146] with the modifications of Goodfellow et al. [(1989) Techniques for mammalian genome transfer. In *Genome Analysis a Practical Approach*. K. E. Davies, ed., IRL Press, Oxford, Washington D.C. pp. 1–17] and Yamada et al. [(1990) *Oncogene* 5:1141–1147]. Briefly, 5×10$^6$ EC3/7C5 cells in a T25 flask were treated first with 0.05 µg/ml colcemid for 48 hr and then with 10 µg/ml cytochalasin B for 30 min. The T25 flasks were centrifuged on edge and the pelleted microcells were suspended in serum free DME medium. The microcells were filtered through first a 5 micron and then a 3 micron polycarbonate filter, treated with 50 µg/ml of phytohemagglutin, and used for polyethylene glycol mediated fusion with recipient cells. Selection of cells containing the MMCneo was started 48 hours after fusion in medium containing 400–800 µg/ml G418.6

B. Chromosome Banding

Trypsin G-banding of chromosomes was performed using the method of Wang & Fedoroff [(1972) *Nature* 235:52–54], and the detection of constitutive heterochromatin with the BSG. C-banding method was done according to Sumner [(1972) *Cell Res.* 75:304–306]. For the detection of chromosome replication by bromodeoxyuridine [BrdU] incorporation, the Fluorescein Plus Giemsa [FPG] staining method of Perry & Wolff [(1974) *Nature* 251:156–158] was used.

C. Immunolabelling of Chromosomes and in situ Hybridization

Indirect immunofluorescence labelling with human anti-centromere serum LU851 [Hadlaczky et al. (1986) *Exp. Cell Res.* 167:1–15, and indirect immunofluorescence and in situ hybridization on the same preparation were performed as described previously [see, Hadlaczky et al. (1991) *Proc. Natl. Acad. Sci. U.S.A.* 88:8106–8110, see also U.S. application Ser. No. 08/375,271]. Immunolabelling with fluorescein-conjugated anti-BrdU monoclonal antibody [Boehringer] was performed according to the procedure recommended by the manufacturer, except that for treatment of mouse A9 chromosomes, 2 M hydrochloric acid was used at 37° C. for 25 min, and for chromosomes of hybrid cells, 1 M hydrochloric acid was used at 37° C. for 30 min.

D. Scanning Electron Microscopy

Preparation of mitotic chromosomes for scanning electron microscopy using osmium impregnation was performed as described previously [Sumner (1991) *Chromosoma* 100:410–418]. The chromosomes were observed with a Hitachi S-800 field emission scanning electron microscope operated with an accelerating voltage of 25 kV.

E. DNA manipulations, plasmids and probes

1. General Methods

All general DNA manipulations were performed by standard procedures [see, e.g., Sambrook et al. (1989) *Molecular cloning: A Laboratory Manual* Cold Spring Harbor Laboratory Press, Cold Spring Harbor, N.Y.]. The mouse major satellite probe was provided by Dr. J. B. Rattner [University of Calgary, Alberta, Canada]. Cloned mouse satellite DNA probes [see, Wong et al. (1988) *Nucl. Acids Res.* 16:11645–11661], including the mouse major satellite probe, were gifts from Dr. J. B. Rattner, University of Calgary. Hamster chromosome painting was done with total hamster genomic DNA, and a cloned repetitive sequence specific to the centromeric region of the chromosome 2 [Fátyol et al. (1994) *Nucl. Acids Res.* 22:3728–3736] was also used. Mouse chromosome painting was done with a cloned long interspersed repetitive sequence [pMCP1.51] specific for the mouse euchromatin.

For cotransfection and for in situ hybridization, the pCH110 β-galactosidase construct [Pharmacia or Invitrogen], and λct 875 Sam7 phage DNA [New England Biolabs] were used.

2. Construction of Plasmid pPuroTel

Plasmid pPuroTel, which carries a Puromycin resistance gene and a cloned 2.5 kb human telomeric sequence [see, SEQ ID No 3], was constructed from the pBabe-puro retroviral vector [Morgenstern et al. (1990) *Nucl. Acids Res.* 18:3587–3596; provided by Dr. L. Székely (Microbiology and Tumorbiology Center, Karolinska Institutet, Stockholm); see, also Tonghua et al. (1995) *Chin. Med. J.* (Beijing, Engl. Ed.) 108:653–659; Couto et al. (1994) *Infect. Immun.* 62:2375–2378; Dunckley et al. (1992) *FEBS Lett.* 296:128–34; French et al. (1995) *Anal. Biochem.* 228:354–355; Liu et al. (1995) *Blood* 85:1095–1103; International PCT application Nos. WO 9520044; WO 9500178, and WO 9419456].

F. Deposited Cell Lines

Cell lines KE1 2/4, EC3/7C5, TF1004G19C5, 19C5xHa4, G3D5 and H1D3 and have been deposited in accord with the Budapest Treaty at the European Collection of Animal cell Culture (ECACC) under Accession Nos. 96040924, 96040925, 96040926, 96040927, 96040928 and 96040929, respectively.

EXAMPLE 2

Preparation EC3/7, EC3/7C5 and Related Cell Lines

The EC3/7 cell line is an LMTK$^-$ mouse cell line that contains the neo-centromere. The EC3/7C5 cell line is a single-cell subclone of EC3/7 that contains the neo-minichromosome.

A. EC3/7 Cell Line

As described in U.S. Pat. No. 5,288,625 [see, also Praznovszky et al. (1991) *Proc. Natl. Acad. Sci. U.S.A.* 88:11042–11046 and Hadlaczky et al. (1991) *Proc. Natl. Acad. Sci. U.S.A.* 88:8106–8110] de novo centromere formation occurs in a transformed mouse LMTK-fibroblast cell line [EC3/7] after cointegration of λ constructs [λCM8 and λgtWESneo] carrying human and bacterial DNA.

By cotransfection of a 14 kb human DNA fragment cloned in lambda [λCM8] and a dominant marker gene [λgtWESneo], a selectable centromere linked to a dominant marker gene [neo-centromere] was formed in mouse LMTK$^-$ cell line EC3/7 [Hadlaczky et al. (1991) *Proc. Natl. Acad. Sci. U.S.A.* 88:8106–8110, see FIG. 1] Integration of the heterologous DNA [the λ DNA and marker gene-encoding DNA] occurred into the short arm of an acrocentric chromosome [chromosome 7 (see, FIG. 1B)], where an amplification process resulted in the formation of the new centromere [neo-centromere (see FIG. 1C)]. On the dicentric chromosome (FIG. 1C) the newly formed centromere region contains all the heterologous DNA (human, lambda, and neo) introduced into the cell, and an active centromere.

Having two functionally active centromeres on the same chromosome causes regular breakages between the centromeres [see, FIG. 1E]. The distance between the two centromeres on the dicentric chromosome is estimated to be ~10–15 Mb, and the breakage that separates the minichromosome occurred between the two centromeres. Such specific chromosome breakages result in the appearance [in approximately 10% of the cells] of a chromosome fragment that carries the neo-centromere [FIG. 1F]. This chromosome fragment is principally composed of human, lambda, plasmid, and neo gene DNA, but it also has some mouse chromosomal DNA. Cytological evidence suggests that during the stabilization of the MMCneo, there was an inverted duplication of the chromosome fragment bearing the neo-centromere. The size of minichromosomes in both cell lines is approximately 20–30 Mb; this finding indicates a two-fold increase in size.

From the EC3/7 cell line, which contains the dicentric chromosome [FIG. 1E], two sublines [EC3/7C5 and EC3/7C6] were selected by repeated single-cell cloning. In these cell lines, the neo-centromere was found exclusively on a small chromosome [neo-minichromosome], while the formerly dicentric chromosome carried detectable amounts of the exogenously-derived DNA sequences but not an active neo-centromere [FIGS. 1F and 1G].

The minichromosomes of cell lines EC3/7C5 and EC3/7C6 are similar. No differences are detected in their architectures at either the cytological or molecular level. The minichromosomes were indistinguishable by conventional restriction endonuclease mapping or by long-range mapping using pulsed field electrophoresis and Southern hybridization. The cytoskeleton of cells of the EC3/7C6 line showed an increased sensitivity to colchicine, so the EC3/7C5 line was used for further detailed analysis.

B. Preparation of the EC3/7C5 and EC3/7C6 cell lines

Integration of the "foreign" DNA, and subsequent amplification of mouse and "foreign" DNA that leads to the formation of a dicentric chromosome, occurs at the centromeric region of the short arm of a mouse chromosome, identified by G-banding as mouse chromosome 7. Because of the presence of two functionally active centromeres on the same chromosome, regular breakages occur between the centromeres. Such specific chromosome breakages give rise to the appearance [in approximately 10% of the cells] of a chromosome fragment carrying the neo-centromere and the remaining portion of he formerly dicentric chromosome. From the EC3/7 cell line carrying either the dicentric chromosome or a chromosome fragment with the neo-centromere, two sublines [EC3/7C5 and EC3/7C6] were selected by repeated single-cell cloning. In these cell lines, the neo-centromere was found exclusively on a minichromosome (neo-minichromosome), while the formerly dicentric chromosome carried traces of "foreign" DNA sequences.

The EC3/7C5 cells, which contain the dicentric chromosome, were produced by subcloning the EC3/7 cell line in high concentrations of G418 [40-fold the lethal dose] for 350 generations. Two single cell-derived stable cell lines [EC3/7C5 and EC3/7C6] were established. These cell lines carry the neo-centromere on minichromosomes and also contain the remaining fragment of the dicentric chromosome. Indirect immunofluorescence with anti-centromere antibodies and subsequent in situ hybridization experiments demonstrated that the minichromosomes derived from the dicentric chromosome. In EC3/7C5 and EC3/7C6 cell lines (140 and 128 metaphases, respectively) no dicentric chromosomes were found and minichromosomes were detected in 97.2% and 98.1% of the cells, respectively. The minichromosomes have been maintained for over 150 cell generations. They do contain the remaining portion of the formerly dicentric chromosome.

Multiple copies of telomeric DNA sequences were detected in the marker centromeric region of the dicentric chromosome by in situ hybridization. This indicates that mouse telomeric sequences were coamplified with the foreign DNA sequences. These stable minichromosome-carrying cell lines provide direct evidence that the extra centromere containing human DNA is functioning and is capable of maintaining the minichromosomes [see, U.S. Pat. No. 5,288,625].

The chromosome breakage in the EC3/7 cells, which separates the neo-centromere from the mouse chromosome, occurred in the G-band positive "foreign" DNA region. This is supported by the observation of traces of λ and human DNA sequences at the broken end of the formerly dicentric chromosome. Comparing the G-band pattern of the chromosome fragment carrying the neo-centromere with that of the stable neo-minichromosome, reveals that the neo-minichromosome is an inverted duplicate of the chromosome fragment that bears the neo-centromere. This is also evidenced by the observation that although the neo-minichromosome carries only one functional centromere, both ends of the minichromosome are heterochromatic, and mouse satellite DNA sequences were found in these heterochromatic regions by in situ hybridization.

These two cell lines EC3/7C5 and EC3/7C6, thus, carry a selectable mammalian minichromosome [MMCneo] with a centromere linked to a dominant marker gene Hadlaczky et al. (1991) Proc. Natl. Acad. Sci. U.S.A. 88:8106–8110]. MMCneo is intended to be used as a vector for minichromosome-mediated gene transfer and has been used as model of a minichromosome-based vector system.

Long range mapping studies of the MMCneo indicated that human DNA and the neo gene constructs integrated into the mouse chromosome separately, followed by the amplification of the chromosome region that contains the exogenous DNA. The MMCneo contains about 30–50 copies of the λCM8 and λgtWESneo DNA in the form of approximately 160 kb repeated blocks, which together cover at least a 3.5 Mb region. In addition to these, there are mouse telomeric sequences [Praznovszky et al. (1991) Proc. Natl. Acad. Sci. U.S.A. 88:11042–11046] and any DNA of mouse origin necessary for the correct higher-ordered structural organization of chromatids.

Using a chromosome painting probe mCPE1.51 [mouse long interspersed repeated DNA], which recognizes exclusively euchromatic mouse DNA, detectable amounts of interspersed repeat sequences were found on the MMCneo by in situ hybridization. The neo-centromere is associated with a small but detectable amount of satellite DNA. The chromosome breakage that separates the neo-centromere from the mouse chromosome occurs in the "foreign" DNA region. This is demonstrated by the presence of lambda and human DNA at the broken end of the formerly dicentric chromosome. At both ends of the MMCneo, however, there traces of mouse major satellite DNA occur as evidence by in situ hybridization. This observation suggests that the doubling in size of the chromosome fragment carrying the neo-centromere during the stabilization of the MMCneo is a result of an inverted duplication. Although mouse telomere sequences, which coamplified with the exogenous DNA sequences during the neo-centromere formation, may provide sufficient telomeres for the MMCneo, the duplication could have supplied the functional telomeres for the minichromosome.

C. Isolation and Partial Purification of Minichromosomes

Mitotic chromosomes of EC3/7C5 cells were isolated as described by Hadlaczky et al. [(1981) *Chromosoma* 81:537–555], using a glycine-hexylene glycol buffer system [Hadlaczky et al. (1982) *Chromosoma* 86:643–659]. Chromosome suspensions were centrifuged at 1,200× g for 30 minutes. The supernatant containing minichromosomes was centrifuged at 5,000× g for 30 minutes and the pellet was resuspended in the appropriate buffer. Partially purified minichromosomes were stored in 50% glycerol at −20° C.

D. Stability of the MMCneo maintenance and neo expression

EC3/7C5 cells grown in non-selective medium for 284 days and then transferred to selective medium containing 400 μg/ml G418 showed a 96% plating efficiency (colony formation) compared to control cells cultured permanently in the presence of G418. Cytogenetic analysis indicated that the MMCneo is stably maintained at one copy per cell both under selective and non-selective culture conditions. Only two metaphases with two MMCneo were found in 2,270 metaphases analyzed.

Southern hybridization analysis showed no detectable changes in DNA restriction patterns, and similar hybridization intensities were observed with a neo probe when DNA from cells grown under selective or non-selective culture conditions were compared.

Northern analysis of RNA transcripts from the neo gene isolated from cells grown under selective and non-selective conditions showed only minor and not significant differences. Expression of the neo gene persisted in EC3/7C5 cells maintained in F-12 medium free of G418 for 290 days under non-selective culture conditions. The long term expression of the neo gene(s) from the minichromosome may be influenced by the nuclear location of the MMCneo. In situ hybridization experiments revealed a preferential peripheral location of the MMCneo in the interphase nucleus. In more than 60% of the 2,500 nuclei analysis, the minichromosome was observed at the perimeter of the nucleus near the nuclear envelope.

EXAMPLE 3

Minichromosome Transfer and Production of the λ-neo-chromosome

A. Minichromosome Transfer

The neo-minichromosome [referred MMCneo, FIG. 2C] has been used for gene transfer by fusion of minichromosome containing cells [EC3/7C5 or EC3/7C6] with different mammalian cells, including hamster and human. Thirty-seven stable hybrid cell lines have been produced. All established hybrid cell lines proved to be true hybrids as evidenced by in situ hybridization using biotinylated human, and hamster genomic, or pMCPE1.51 mouse long interspersed repeated DNA probes for "chromosome painting".

The MMCneo has also been successfully transferred into mouse A9, L929 and pluripotent F9 teratocarcinoma cells by fusion of microcells derived from EC3/7C5 cells. Transfer was confirmed by PCR, Southern blotting and in situ hybridization with minichromosome-specific probes. The cytogenetic analysis confirmed that, as expected for microcell fusion, a few cells [1–5%] received [or retained] the MMCneo.

These demonstrate that the MMCneo is tolerated by a wide range of cells. The prokaryotic genes and the extra dosage for the human and lambda sequences carried on the minichromosome seem to be not disadvantageous for tissue culture cells.

The MMCneo is the smallest chromosome of the EC3/7C5 genome and is estimated to be approximately 20–30 Mb, which is significantly smaller than the majority of the host cell (mouse) chromosomes. By virtue of the smaller size, minichromosomes can be partially purified from a suspension of isolated chromosomes by a simple differential centrifugation. In this way, minichromosome suspensions of 15–20% purity have been prepared. These enriched minichromosome preparations can be used to introduce, such as by microinjection or lipofection the minichromosome into selected target cells. Target cells include therapeutic cells that can be use in methods of gene therapy, and also embryonic cells for the preparation of transgenic animals.

The MMCneo is capable of autonomous replication, is stably maintained in cells, and permits persistent expression of the neo gene(s), even after long-term culturing under non-selective conditions. It is a non-integrative vector that appears to occupy a territory near the nuclear envelope. Its peripheral localization in the nucleus may have an important role in maintaining the functional integrity and stability of the MMCneo. Functional compartmentalization of the host nucleus may have an effect on the function of foreign sequences. In addition, contains megabases of lambda DNA sequences that should serve as a target site for homologous recombination and thus integration of desired gene(s) into the MMCneo. It can be transferred by cell and microcell fusion, microinjection, electroporation, or chromosome uptake. The neo-centromere of the MMCneo is capable of maintaining and supporting the normal segregation of a larger 150–200 Mb λneo chromosome. This result (B) demonstrates that the MMCneo chromosome should be useful for carrying large fragments of heterologous DNA.

B. Production of the λ-neo-chromosome

In one hybrid cell line KE1-2/4 made by fusion of EC3/7 and Chinese hamster ovary cells [FIG 2D], the separation of the neo-centromere from the dicentric chromosome was associated with a further amplification process. This amplification resulted in the formation of a stable, chromosome of average size [i.e., the λ neo-chromosome; see, Praznovszky et al. (1991) *Proc. Natl. Acad. Sci. U.S.A.* 88:11042–11046]. The λ neo-chromosome carries a terminally located functional centromere, and is composed of seven large amplicons containing multiple copies of λ, human, bacterial, and mouse DNA sequences [see FIG. 2]. The amplicons are separated by mouse major satellite DNA [Praznovszky et al. (1991) *Proc. Natl. Acad. Sci. U.S.A.* 88:11042–11046] which forms narrow bands of constitutive heterochromatin between the amplicons.

EXAMPLE 4

Formation of the "Sausage Chromosome" [SC]

The findings set forth in the above EXAMPLES demonstrate that the centromeric region of the mouse chromosome 7 has the capacity for largescale amplification [other results indicate that this capacity is not unique to chromosome 7]. This conclusion is further supported by results from cotransfection experiments, in which a second dominant selectable marker gene and a non-selected marker gene were introduced into EC3/7 cells carrying the formerly dicentric chromosome 7 and the neo-minichromosome.

The EC3/7C5 cell line was transformed with λ phage DNA, a hygromycin construct [pH132], and β-galactosidase construct [pCH110]. Stable transformants were selected in the presence of high concentrations [400 μg/ml] Hygromycin B, and analysed by Southern hybridization. Established transformant cell lines showing multiple copies of integrated exogenous DNA were studied by in situ hybridization to localize the integration site(s), and by LacZ staining to detect β-galactosidase expression.

A. Materials and Methods

1. Construction of pH132

The pH 132 plasmid carries the hygromycin B resistance gene and the anti-HIV-1 gag ribozyme [see, SEQ ID NO. 6 for DNA sequence that corresponds to the sequence of the ribozyme] under control of the β-actin promoter. This plasmid was constructed from pHyg plasmid [Sugden et al. (1985) Mol. Cell. Biol. 5:410–413; a gift from Dr. A. D. Riggs, Beckman Research Institute, Duarte; see, also, e.g., U.S. Pat. No. 4,997,764], and from pPC-RAG12 plasmid [see, Chang et al. (1990) Clin Biotech 2:23–31; provided by Dr. J. J. Rossi, Beckman Research Institute, Duarte; see, also U.S. Pat. Nos. 5,272,262, 5,149,796 and 5,144,019, which describes the anti-HIV gag ribozyme and construction of a mammalian expression vector containing the ribozyme insert linked to the β-actin promoter and SV40 late gene transcriptianl termination and polyA signals]. The ribozyme insert flanked by BamHI linkers was inserted into BamHI-digested pHβ-Apr-1gpt [see, Gunning et al. (1987) Proc. Natl. Acad. Sci. U.S.A. 84:4831–4835, see, also U.S. Pat. No. 5,144,019]. An EcoRI/Xhol fragment of this vector was inserted into EcoRI/Xhol-digested pHyg.

Plasmid pH132 was constructed as follows. First, pPC-RAG12 [described by Chang et al. (1990) Clin. Biotech. 2:23–31] was digested with BamHI to excise a fragment containing an anti-HIV ribozyme gene [referred to as ribozyme D by Chang et al. [(1990) Clin. Biotech. 2:23–31]; see also U.S. Pat. No. 5,144,019 to Rossi et al., particularly FIG. 4 of the patent] flanked by the human β-actin promoter at the 5' end of the gene and the SV40 late transcriptional termination and polyadenylation signals at the 3' end of the gene. As described by Chang et al. [(1990) Clin. Biotech. 2:23–31], ribozyme D is targeted for cleavage of the translational initiation region of the HIV gag gene. This fragment of pPC-RAG12 was subcloned into pBluescript-KS(+) [Stratagene, La Jolla, Calif.] to produce plasmid 132. Plasmid 132 was then digested with XhoI and EcoRI to yield a fragment containing the ribozyme D gene flanked by the β-actin promoter at the 5' end and the SV40 termination and polyadenylation signals at the 3' end of the gene. This fragment was ligated to the largest fragment generated by digestion of pHyg [Sugden et al. (1985) Mol. Cell. Biol. 5:410–413] with EcoRI and SalI to yield pH132. Thus, pH132 is an ~9.3 kb plasmid containing the following elements: the β-actin promoter linked to an anti-HIV ribozyme gene followed by the SV40 termination and polyadenylation signals, the thymidine kinase gene promoter linked to the hygromycin resistance gene followed by the thymidine kinase gene polyadenylation signal, and the E. coli ColE1 origin of replication and the ampicillin-resistance gene.

The plasmid pHyg [see, e.g., U.S. Pat. Nos. 4,997,764, 4,686,186 and 5,162,215], which confers resistance to hygromycin B using transcriptional controls from the HSV-1 tk gene, was originally constructed from pKan2 [Yates et al. (1984) Proc. Natl. Acad. Sci. U.S.A. 81:3806–3810] and pLG89 [see, Gritz et al. (1983) Gene 25:179–188]. Briefly pKan2 was digested with Smal and Bglll to remove the sequences derived from transposon Tn5. The hygromycin-resistance hph gene was inserted into the digested pKan2 using blunt-end ligation at the Snal site and "sticky-end" ligation [using 1 Weiss unit of T4 DNA ligase (BRL) in 20 microliter volume] at the BglII site. The SmaI and BglII sites of pKan2 were lost during ligation.

The resulting plasmid pH132, produced from introduction of the antiHIV ribozyme construct with promoter and polyA site into pHyg, includes the anti-HIV ribozyme under control of the β-actin promoter as well as the Hyg gene under control of the TK promoter.

2. Chromosome Banding

Trypsin G-banding of chromosomes was performed as described in EXAMPLE 1.

3. Cell Cultures

TF1004G19 and TF1004G19C5 mouse cells and the 19xHa4 hybrid, described below, and its sublines were cultured in F-12 medium containing 400 μg/ml Hygromycin B [Calbiochem].

B. Cotransfection of EC3/7C5 to produce TF1004G-19

Cotransfection of EC3/7C5 cells with plasmids [pH132, pCH110 available from Pharmacia, see, also Hall et al. (1983) J. Mol. Appl. Gen. 2:101–109] and with λ DNA [λcI 875 Sam 7(New England Biolabs)] was made using the calcium phosphate DNA precipitation method [see, e.g., Chen et al. (1987) Mol. Cell. Biol. 7:2745–2752], using 2–5 μg plasmid DNA and 20 μg λ phage DNA per 5×10$^6$ recipient cells.

C. Cell Lines Containing the Sausage Chromosome

One transformant TF1004G-19 was identified. It has a high copy number of integrated pH132 and pCH110 sequences, and a high level of β-galactosidase expression. G-banding and in situ hybridization with a human probe [CM8; see, e.g., U.S. application Ser. No. 08/375,271] revealed unexpectedly that integration had occurred in the formerly dicentric chromosome 7 of the EC3/7C5 cell line. Furthermore, this chromosome carried a newly formed heterochromatic chromosome arm. The size of this heterochromatic arm varied between ~150 and ~800 Mb in individual metaphases.

By single cell cloning from the TF1004G-19 cell line, a subclone TF1004G-19C5 [FIG 2D], which carries a stable chromosome 7 with a ~100–150 Mb heterochromatic arm [the sausage chromosome] was obtained. This cell line has been deposited in the ECACC under Accession No. 96040926. This chromosome arm is composed of four to five satellite segments rich in satellite DNA, and evenly spaced integrated heterologous "foreign" DNA sequences. At the end of the compact heterochromatic arm of the sausage chromosome, a less condensed euchromatic terminal segment is regularly observed. This subclone was used for further analyses.

D. Demonstration that the Sausage Chromosome is Derived from the Formerly Dicentric Chromosome In situ hybridization with lambda phage and pH132 DNA on the TF1004G-19C5 cell line showed positive hybridization only on the minichromosome and on the heterochromatic arm of the "sausage" chromosome [FIG. 2D]. It appears that the "sausage" chromosome [herein also referred to as the SC] developed from the formerly dicentric chromosome (FD) of the EC3/7C5 cell line.

To establish this, the integration sites of pCH110 and pH132 plasmids was determined. This was accomplished by in situ hybridization on these cells with biotin-labeled subfragments of the hygromycin resistance gene and the β-galactosidase gene. Both experiments resulted in narrow hybridizing bands on the heterochromatic arm of sausage chromosome. The same hybridization pattern was detected on the sausage chromosome using a mixture of biotin-labeled λ probe and pH132 plasmid, proving the cointegration of lambda phages, pH132 and pCH110 plasmids.

To examine this further, the cells were cultured in the presence of the DNA-binding dye Hoechst 33258. Culturing of mouse cells in the presence of this dye results in under-condensation of the pericentric heterochromatin of metaphase chromosomes, thereby permitting better observation of the hybridization pattern. Using this technique the heterochromatic arm of sausage chromosome of 19C5 cell showed regular under-condensation revealing the details of the structure of "sausage" chromosome by in situ hybridization. Results of in situ hybridization on Hoechst-treated TF1004G/19C5 cells with biotin-labeled subfragments of hygromycin resistance and β-galactosidase genes shows that these genes are localized only in the heterochromatic arm of the sausage chromosome. In addition an equal banding hybridization pattern was observed. This pattern of repeating units [amplicons] clearly indicates that the sausage chromosome was formed by an amplification process and that the lambda phage, pH132 and pCH110 plasmid DNA sequences border the amplicons.

In another series of experiments, using fluorescence in situ hybridization [FISH] was carried out with mouse major satellite DNA, the main component of the mouse pericentric heterochromatin, the results confirmed that the amplicons of the sausage chromosome are primarily composed of satellite DNA.

E. The Sausage Chromosome has one Centromere

To determine whether mouse centromeric sequences had participated in the amplification process forming the "sausage" chromosome and whether or not the amplicons carry inactive centromeres, in situ hybridization was carried out with mouse minor satellite DNA. Mouse minor satellite DNA is localized specifically near the centromeres of all mouse chromosome. Positive hybridization was detected in all mouse centromeres including the sausage chromosome, which, however, only showed a positive signal at the beginning of the heterochromatic arm.

Indirect immunofluorescence with human anti-centromere antibody [LU 851] that only which can recognizes the functional centromeres [see, e.g., Hadlaczky et al. (1989) *Chromosoma* 97:282–288] proved that sausage chromosome has only one active centromere. The centromere comes from the formerly dicentric part of the chromosome and co-localizes with the in situ hybridization signal of the mouse minor DNA probe.

F. The Selected and Non-selected Heterologous DNA in the Heterochromatin of the Sausage Chromosome is Expressed 1. High Levels of the Heterologous Genes are Expressed The TF1004G/19C5 cell line thus carries multiple copies of hygromycin resistance and β-galactosidase genes localized only in the heterochromatic arm of the sausage chromosome. The 19C5 cells can grow very well in the presence of 200 μg/ml or even 400 μg/ml hygromycin B. (The level of expression was determined by Northern hybridization with subfragment of hygromycin resistance gene and single copy gene).

The expression of the non-selected β-galactosidase gene in the TF1004G/19C5 transformant, was detected with LacZ staining of the cells. By this method one hundred percent of the cells stained dark blue, showing that there is a high level of γ-galactosidase expression in all of 19C5 cells.

2. The Heterologous Genes that are Expressed are in the Heterochromatin

To demonstrate that the genes localized in the constitutive heterochromatin of the sausage chromosome provide the hygromycin resistance and the LacZ staining capability of 19C5 transformant [i.e. β-gal express], PEG induced cell fusion between a TF1004G/19C5 mouse cell and Chinese hamster ovary cell was performed. The hybrids were selected and maintained in HAT medium containing G418 [400 μg/ml] and hygromycin [200 μg/ml]. Two hybrid clones designated 19C5xHa3 and 19C5xHa4, which has been deposited in the ECACC under Accession No. 96040927, were selected. Both carry the sausage chromosome and the minichromosome.

Twenty-seven single cell derived colonies of 19C5xHa4 hybrid were maintained and analyzed as individual subclones. In situ hybridization with hamster and mouse chromosome painting probes and hamster chromosome 2 specific probes verified that the 19C5xHa4 clone contains the complete Chinese hamster genome and a partial mouse genome. All 19C5xHa4 subclones retained the hamster genome, but different subclones showed different number of mouse chromosomes indicating the preferential elimination of mouse chromosomes.

To promote further elimination of mouse chromosomes hybrid cells were repeatedly treated with Brd U. The BrdU treatments, which destabilize the genome, result in significant loss of mouse chromosomes. The BrdU treated 19C5xHa4 hybrid cells were divided to three groups. One group of the hybrid cells (GH) was maintained in the presence of hygromycin (200 μg/ml) and G418 (400 μg/ml), and the other two groups of the cells were cultured under G418 (G) or hygromycin (H) selection conditions to promote the elimination of sausage or minichromosome.

One month later, single cell derived subclones were established from these three subcultures of the TF1004G/19C5xHa4 hybrid line. The subclones were monitored by in situ hybridization with biotin-labeled lambda phage and hamster chromosome painting probes. Four individual clones [G2B5, G3C5, G4D6, G2B4] selected in the presence of G418 that have lost the sausage chromosome but retained minichromosome were found. Under hygromycin selection only one subclone [H1D3] lost the minichromosome. In this clone the sausage chromosome was present.

Since hygromycin resistance and β-galactosidase genes were thought to be expressed from the sausage chromosome, the expression of these genes were analyzed in the four subclones that had lost the sausage chromosome. In the presence of 200 μg/ml hygromycin, one hundred percent of the cells of four individual subclones died. In order to detect the β-galactosidase expression hybrid subclones were analyzed by LacZ staining. One hundred percent of the cells of the four subclones that lost the sausage chromosome also lost the LacZ staining capability. All of the other hybrid subclones that not lost the sausage chromosome under the non-selective culture conditions showed positive LacZ staining.

These findings demonstrate that the expression of hygromycin resistance and β-galactosidase genes is linked to the presence of the sausage chromosome and results of in situ hybridizations show that the heterologous DNA is expressed from the constitutive heterochromatin of the sausage chromosome.

By in situ hybridization in three other hybrid subclones [G2C6, G2D1, and G4D5] the presence of the sausage chromosome was not detected. By the LacZ staining method some stained cells were detected in these hybrid lines and when these subclones were transferred to hygromycin selection some colonies survived. Cytological analysis and in situ hybridization of these hygromycin resistance colonies revealed the presence of the sausage chromosome, suggesting that only the cells of G2C6, G2D1 and G4D5 hybrids that had not lost the sausage chromosome were able to preserve the hygromycin resistance and β-galactosidase expression. These results confirmed that the expression of these genes is linked to the presence of the sausage chromosome. The level of β-galactosidase expression was determined by the immunoblot technique using monoclonal antibody.

Hygromycin resistance and β-galactosidase expression of the cells which contained the sausage chromosome were provided by the genes localized in the mouse pericentric heterochromatin. This was demonstrated by performing Southern DNA hybridizations on the hybrid cells that lack the sausage chromosome with PCR amplified subfragments of hygromycin resistance and β-galactosidase genes. None of the subclones showed hybridization with these probes, however, all of the analyzed clones contained the minichromosome as well. Other hybrid clones that contain the sausage chromosome showed intense hybridization with these DNA probes. These results lead to the conclusion that hygromycin resistance and β-galactosidase expression of the cells that contain the sausage chromosome were provided by the genes localized in the mouse pericentric heterochromatin.

EXAMPLE 5

The Gigachromosome

As described in Example 4, the sausage chromosome was transferred into Chinese hamster cells by cell fusion. Using Hygromycin B/HAT selection, two hybrid clones 19C5xHa3 and 19C5xHa4 were produced that carry sausage chromosome. In situ hybridization, using hamster and mouse chromosome-painting probes and a hamster chromosome 2 specific probe, verified that clone 19C5xHa4 contains a complete Chinese hamster genome as well as partial mouse genomes. Twenty-seven separate colonies of 19C5xHa4 cells were maintained and analyzed as individual subclones. Twenty-six out of 27 subclones contained a morphologically unchanged sausage chromosome.

In one clone 19C5xHa47 [see FIG. 2E], the heterochromatic arm of the sausage chromosome became unstable and showed continuous intrachromosomal growth. In extreme cases, the amplified chromosome arm exceeded 1000 Mb in size (gigachromosome).

EXAMPLE 6

The Stable Megachromosome

A. Formation of the Megachromosome

All 19C5xHa4 subclones retained a complete hamster genome, but different subclones showed different numbers of mouse chromosomes, indicating the preferential elimination of mouse chromosomes. As described in Example 4, to promote further elimination of mouse chromosomes, hybrid cells were repeatedly treated with $10^{-4}$ M BrdU for 16 hours and single cell subclones were established. The BrdU treatments appeared to destabilize the genome, resulting in a change in the sausage chromosome as well. A gradual increase in a cell population in which a further amplification had occurred was observed. In addition to the ~100–150 Mb heterochromatic arm of the sausage chromosome, an extra centromere and a ~150–250 Mb heterochromatic chromosome arm were formed, which differed from those of mouse chromosome 7. By the acquisition of another euchromatic terminal segment, a new submetacentric chromosome (megachromosome) was formed. Seventy-nine individual subclones were established from these BrdU-treated cultures, by single-cell cloning: 42 subclones carried the intact megachromosome, 5 subclones carried the sausage chromosome, and in 32 subclones fragments or translocated segments of the megachromosome were observed. Twenty-six subclones were cultured under non-selective conditions over a 2 month period. In 19 out of 26 subclones, the megachromosome was retained. Those subclones which lost the megachromosomes all became sensitive to Hygromycin B and had no β-galactosidase expression, indicating that both markers were linked to the megachromosome.

Two sublines (G3D5 and H1D3), which were chosen for further experiments, showed no changes in the morphology of the megachromosome during more than 100 generations under selective conditions.

B. Structure of the Megachromosome

Figure 3:
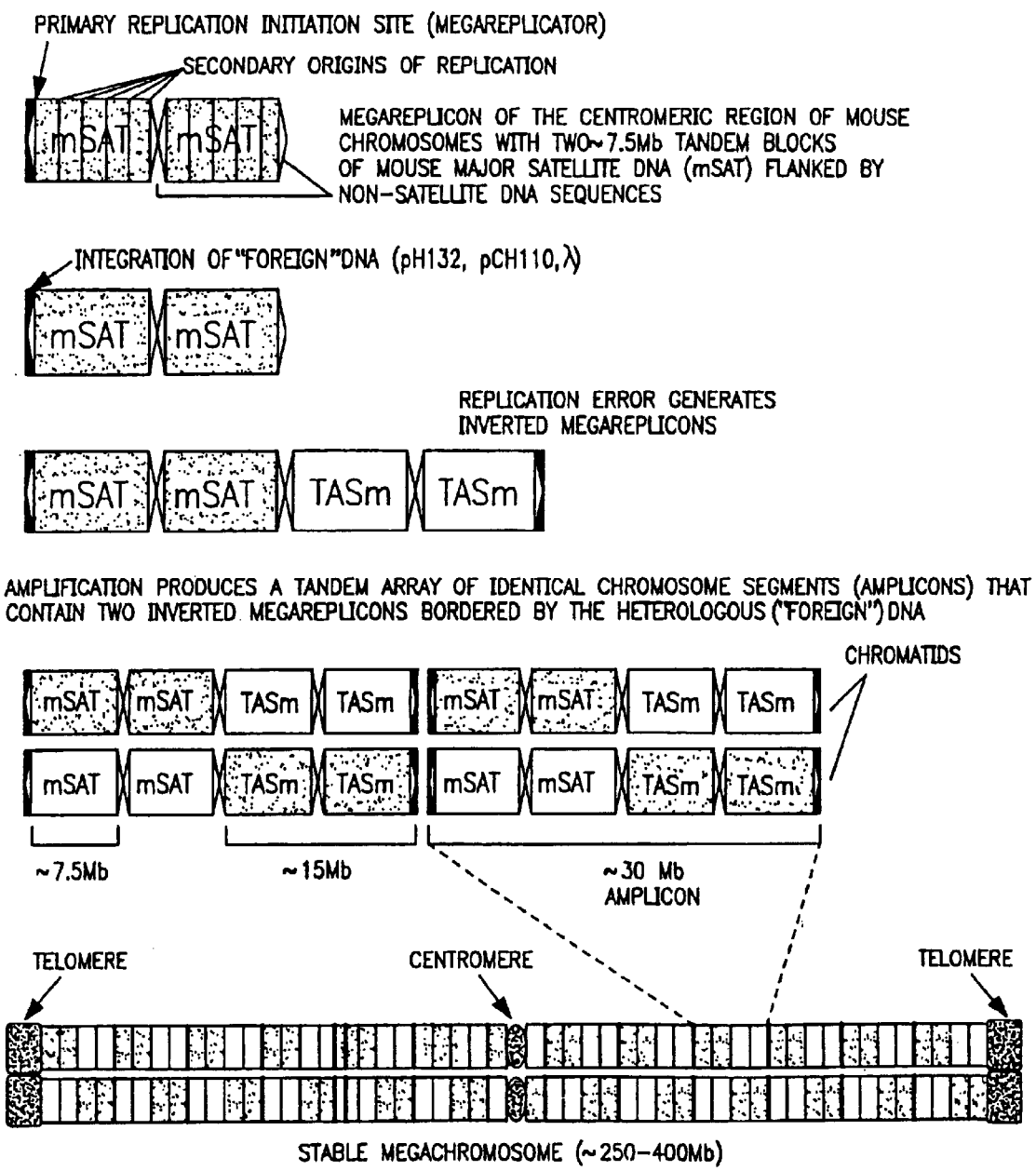
FIG. 3 Schematic diagram of the replicon structure and a scheme by which the megachromosome could be produced.

The following results demonstrate that, apart from the euchromatic terminal segments, the whole megachromosome is constitutive heterochromatin, containing a tandem array of at least 40 [~7.5 Mb] blocks of mouse major satellite DNA [see FIGS. 2 and 3]. Four satellite DNA blocks are organized into a giant palindrome [amplicon] carrying integrated exogenous DNA sequences at each end. The long and short arms of the submetacentric megachromosome contains 6 and 4 amplicons, respectively.

1. The Megachromosome is Composed Primarily of Heterochromatin

Except for the terminal regions, the megachromosome is composed primarily of heterochromatin. This was demonstrated by G-banding of the megachromosome, which resulted in positive staining characteristic of constitutive heterochromatin. Apart from the terminal regions, the whole megachromosome appears to be heterochromatic. Mouse major satellite DNA is the main component of the pericentric, constitutive heterochromatin of mouse chromosomes and represents ~10% of the total DNA [Waring et al. (1966) *Science* 154:791–794]. Using a mouse major satellite DNA probe for in situ hybridization, strong hybridization was observed throughout the megachromosome, except for its terminal regions. The hybridization showed a segmented pattern: four large blocks appeared on the short arm and usually 4–7 blocks were seen on the long arm. By comparing these segments with the pericentric regions of normal mouse chromosomes that carry approximately ~15 Mb of major satellite, the size of the blocks of major satellite on the megachromosome was estimated to be ~30 Mb.

Using a mouse probe specific to euchromatin [pMCPE1.51; a mouse long interspersed repeated DNA probe], positive hybridization was detected only on the terminal segments of the megachromosome of the H1D3 hybrid subline. In the G3D5 hybrids, hybridization with a hamster-specific probe revealed that several megachromosomes contained terminal segments of hamster origin on the long arm. This observation indicated that the acquisition of the terminal segments on these chromosomes happened in the hybrid cells, and that the long arm of the megachromosome was the recently formed one. When a mouse minor satellite probe was used, specific to the centromeres of mouse chromosomes [Wong et al. (1988) *Nucl. Acids Res.* 16:11645–11661], a strong hybridization signal was detected only at the primary constriction of the megachromosome, which colocalized with the positive immunofluorescence signal produced with human anti-centromere serum [LU 851].

In situ hybridization experiments with pH132, pCH110, and λDNA probes revealed that all heterologous DNA was located in the gaps between the mouse major satellite segments. Each segment of mouse major satellite was bordered by a narrow band of integrated heterologous DNA, except at the second segment of the long arm where a double band existed, indicating that the major satellite segment was missing or considerably reduced in size here. This chromosome region served as a useful cytological marker in identifying the long arm of the megachromosome. At a frequency of $10^{-4}$, "restoration" of these missing satellite DNA blocks was observed in one chromatid, when the formation of a whole segment on one chromatid occurred.

After Hoechst 33258 treatment (50 μg/ml for 16 hours), the megachromosome showed undercondensation throughout its length except for the terminal segments. This made it possible to study the architecture of the megachromosome at higher resolution. In situ hybridization with the mouse major satellite probe on undercondensed megachromosomes demonstrated that the ~30 Mb major satellite segments were composed of four blocks of ~7.5 Mb separated from each other by a narrow band of nonhybridizing sequences [FIG. 3]. Similar segmentation can be observed in the large block of pericentric heterochromatin in metacentric mouse chromosomes from the LMTK⁻ and A9 cell lines.

2. The Megachromosome is Composed of Segments Containing Two Tandem ~7.5 Mb Blocks are Followed by Two Inverted Blocks Because of the asymmetry in thymidine content between the two strands of the DNA of the mouse major satellite, when mouse cells are grown in the presence of BrdU for a single S phase, the constitutive heterochromatin shows lateral asymmetry after FPG staining. Also, in the 19C5xHa4 hybrids, the thymidine-kinase the [Tk] deficiency of the mouse fibroblast cells was complemented by the hamster Tk gene, permitting BrdU incorporation experiments.

A striking structural regularity in the megachromosome was detected using the FPG technique. In both chromatids, alternating dark and light staining that produced a checkered appearance of the megachromosome was observed. A similar picture was obtained by labelling with fluoresce-inconjugated anti-BrdU antibody. Comparing these pictures to the segmented appearance of the megachromosome, showed that one dark and one light FPG band corresponded to one ~30 Mb segment of the megachromosome.

These results suggest that the two halves of the ~30 Mb segment have an inverted orientation. This was verified by combining in situ hybridization and immunolabelling of the incorporated BrdU with fluoresce-inconjugated anti-BrdU antibody on the same chromosome. Since the ~30 Mb segments of the megachromosome are composed of four blocks of mouse major satellite, it can be concluded that two tandem ~7.5 Mb blocks are followed by two inverted blocks within one segment.

Large-scale mapping of megachromosome DNA by pulsed-field electrophoresis and Southern hybridization with "foreign" DNA probes revealed a simple pattern of restriction fragments. Using endonucleases with none, or only a single cleavage site in the integrated foreign DNA sequences, followed by hybridization with a hyg probe, 1–4 predominant fragments were detected. Since the megachromosome contains 10–12 amplicons with an estimated 3–8 copies of hyg sequences per amplicon (30–90 copies per megachromosome), the small number of hybridizing fragments indicates the homogeneity of DNA in the amplified segments.

3. Scanning Electron Microscopy of the Megachromosome Confirmed the Above Findings The homogeneous architecture of the heterochromatic arms of the megachromosome was confirmed by high resolution scanning electron microscopy. Extended arms of megachromosomes, and the pericentric heterochromatic region of mouse chromosomes, treated with Hoechst 33258, showed similar structure. The constitutive heterochromatic regions appeared more compact than the euchromatic segments. Apart from the terminal regions, both arms of the megachromosome were completely extended, and showed faint grooves, which should correspond to the border of the satellite DNA blocks in the non-amplified chromosomes and in the megachromosome. Without Hoechst treatment, the grooves seemed to correspond to the amplicon borders on the megachromosome arms. In addition, centromeres showed a more compact, finely fibrous appearance than the surrounding heterochromatin.

C. Formation of the Megachromosome

FIG. 2 schematically sets forth the events leading to the formation of the stable megachromosome: (A) A single E-type amplification in the centromeric region of chromosome 7 generates the neo-centromere linked to the integrated foreign DNA, and forms a dicentric chromosome. Multiple E-type amplification forms the λ neo-chromosome, which was derived from chromosome 7 and stabilized in a mouse-hamster hybrid cell line; (B) Specific breakage between the centromeres of a dicentric chromosome 7 generates a chromosome fragment with the neo-centromere, and a chromosome 7 with traces of foreign DNA at the end; (C) Inverted duplication of the fragment bearing the neo-centromere results in the formation of a stable neo-minichromosome; (D) Integration of exogenous DNA into the foreign DNA region of the formerly dicentric chromosome 7 initiates H-type amplification, and the formation of a heterochromatic arm. By capturing a euchromatic terminal segment, this new chromosome arm is stabilized in the form of the "sausage" chromosome; (E) BrdU treatment and/or drug selection appears to induce further H-type amplification, which results in the formation of an unstable gigachromosome: (F) Repeated BrdU treatments and/or drug selection induce further H-type amplification including a centromere duplication, which leads to the formation of another heterochromatic chromosome arm. It is split off from the chromosome 7 by chromosome breakage and acquires a terminal segment to form the stable megachromosome.

EXAMPLE 7

Summary of Some of the Cell Lines with SATACS and Minichromosomes that have been Constructed LMTK⁻-derived cell line, which is a mouse fibroblast cell line, was transfected with λCM8 and λgtWESneo DNA[see, EXAMPLE 2] to produce transformed cell lines. Among these cell lines was EC3/7, deposited at the European Collection of Animal cell Culture (ECACC) under Accession No. 90051001 [see, U.S. Pat. No. 5,288,625; see, also Hadlaczky et al. (1991) *Proc. Natl. Acad. Sci. U.S.A.* 88:8106–8110 and U.S. application Ser. No. 08/375,271]. This cell line contains the dicentric chromosome with the neo centromere. Recloning and selection produced cell lines such as EC3/7C5, which are cell lines with the stable neo-minichromosome [see, FIG. 2C].

Fusion of EC3/7 with CHO-K2O cells and selection with G418/HAT produced hybrid cell lines, among these was KE1 2/4, which has been deposited with the ECACC under Accession No. 96040924. KE1 2/4 is a table cell line that contains the λ neo-chromosome [see, FIG. 2D; see, also U.S. Pat. No. 5,288,625], produced by E type amplifications. KE1 2/4 as been transfected with vectors containing lambda DNA, selectable markers, such as puromycin resistance, and genes of interest, such as p53, anti-HIV ribozymes. These vectors target the gene of interest into the λ neo-chromosome by virtue of homologous recombination with the heterologous DNA in the chromosome.

The EC3/7C5 cell line has been co-transfected with pH132, pCH110 and λ DNA[see, EXAMPLE 2] as well as other constructs. Various clones and subclones have been selected. For example transformation with a construct that includes p53 encoding DNA, produced cells designated C5pMCT53.

As discussed above, cotransfection of EC3/7C5 cells with plasmids [pH132, pCH110 available from Pharmacia, see, also Hall et al. (1983) *J. Mol. Appl. Gen.* 2:101–109] and with λ DNA [λcl 875 Sam 7(New England Biolabs)] produced transformed cells. Among these is TF1004G24, which contains the DNA encoding the anti-HIV ribozyme in the neo-minichromosome. Recloning of TF1004G24 produced numerous cell lines. Among these the NHHL24 cell line. This cell line also has the anti-HIV ribozyme in the neo-minichromosome and expresses high levels of β-gal. It has been fused with CHO-K2O cells to produce various hybrids.

Recloning and selection of the TF1004G transformants produced the cell line TF1004G-19, discussed above in EXAMPLE 4, which contains the unstable sausage chromosome. Single cell cloning produced the TF1004G19-C5 [see FIG. 4] cell line, which has a stable sausage chromosome. TF1004G-19C5 has been fused with CHO cells and the hybrids grown under selective conditions to produce the 19C5xHa4 cell line [see, EXAMPLE 4] and others. BrdU treatment of 19C5xHa4 cells and growth under selective conditions (neomycin (G) and/or hygromycin (H)] has produced hybrid cell lines with the gigachromsome [see FIG. 2E] and the G3D5 and G4D6 cell lines and others. G3D5 has the neo-minichromosome and the megachromosome, G4D6 has only the neo-minichromosome.

Recloning of G3D5 in GH medium produced numerous clones. Among these is H1D3 [see FIG. 4], which has the stable megachromosome. Repeated BrDU treatment and recloning has produced the HB31 cell line, which has been used for transformations with the pTEMPUD, pTEMPU and pTEMPU3 vectors [see, Example 12, below].

H1D3 has been fused with a CD4$^+$ Hela cell line that carries DNA encoding CD4 and neomycin resistance on a plasmid [see, e.g., U.S. Pat. Nos. 5,413,914, 5,409,810, 5,266,600, 5,223,263, 5,215,914 and 5,144,019, which describe these Hela cells]. Selection with GH has produced hybrids, including H1xHE41 [see FIG. 4], which carries the megachromosome and also a single human chromosome that includes the CD4neo construct. Repeated BrdU treatment and single cell cloning has produced cell lines with the megachromosome [cell line 1B3, see FIG. 4], cell lines, such as 1B4 and others that have a dwarf megachromosome [~150–200 Mb] and cell lines , such as 1C3, which has micromegachromosome [~60–90 Mb]. About 25% of the 1B3 cells have a truncated megachromosome [~90–120 Mb].

EXAMPLE 8

Replication of the Megachromosome

This homogeneous architecture of the megachromomes provides a unique opportunity to perform a detailed analysis of the replication of the constitutive heterochromatin.

A. Materials and Methods

1. Culture of Cell Lines

H1D3 mouse-hamster hybrid cells carrying the megachromosome [see, EXAMPLE 4] were cultured in F-12 medium containing 10% fetal calf serum [FCS] and 400 μg/ml Hygromycin B [Calbiochem]. G3D5 hybrid cells [see, Example 4] were maintained in F-12 medium containing 10% FCS, 400 μg/ml Hygromycin B (Calbiochem), and 400 μg/ml G418[SIGMA]. Mouse A9 fibroblast cells were cultured in F-12 medium supplemented with 10% FCS.

2. BrdU Labelling

In typical experiments, 20–24 parallel semi-confluent cell cultures were set up in 10 cm Petri dishes. Bromodeoxyuridine (BrdU) (Fluka) was dissolved in distilled water alkalized with a drop of NaOH, to make a $10^{-2}$ M stock solution. Aliquots of 10–50 μl of this BrdU stock solution were added to each 10 ml culture, to give a final BrdU concentration of 10–50 μM. The cells were cultured in the presence of BrdU for 30 min, and then washed with warm complete medium, and incubated without BrdU until required. At this point, 5 μg/ml colchicine was added to a sample culture every 1 or 2 h. After 1–2 h colchicine treatment, mitotic cells were collected by "shake-off" and regular chromosome preparations were made for immunolabelling.

3. Immunolabelling of Chromosomes and in situ Hybridization

Immunolabelling with fluorescein-conjugated anti-BrdU monoclonal antibody (Boehringer) was done according to the manufacturer's recommendations, except that for mouse A9 chromosomes, 2 M hydrochloric acid was used at 37° C. for 25 min, while for chromosomes of hybrid cells, 1 M hydrochloric acid was used at 37° C. for 30 min. In situ hybridization with biotin-labelled probes, and indirect immunofluorescence and in situ hybridization on the same preparation, were performed as described previously [Hadlaczky et al. (1991) *Proc. Natl. Acad. Sci. U.S.A.* 88:8106–8110, see, also U.S. Pat. No. 5,288,625].

4. Microscopy

All observations and microphotography were made by using a Vanox AHBS (Olympus) microscope. Fujicolor 400 Super G or Fujicolor 1600 Super HG high-speed colour negatives were used for photographs.

B. Results

The replication of the megachromosome was analyzed by BrdU pulse labelling followed by immunolabelling. The basic parameters for DNA labelling in vivo were first established. Using a 30 min pulse of 50 μM BrdU in parallel cultures, samples were taken and fixed at 5 min intervals from the beginning of the pulse, and every 15 min up to 1 h after the removal of BrdU. Incorporated BrdU was detected by immunolabelling with fluorescein-conjugated anti-BrdU monoclonal antibody. At the first time point (5 min) 38% of the nuclei were labelled, and a gradual increase in the number of labelled nuclei was observed during incubation in the presence of BrdU, culminating in 46% in the 30 min sample, at the time of the removal of BrdU. At further time points (60, 75, and 90 min) no significant changes were observed, and the fraction of labelled nuclei remaining constant [44.5–46%].

These results indicate that (i) the incorporation of the BrdU is a rapid process, (ii) the 30 min pulse-time is sufficient for reliable labelling of S-phase nuclei, and (iii) the BrdU can be effectively removed from the cultures by washing.

The length of the cell cycle of the 19C5xHa4 hybrid cells was estimated by measuring the time between the appearance of the earliest BrdU signals on the extreme late replicating chromosome segments and the appearance of the same pattern only on one of the chromatids of the chromosomes after one completed cell cycle. The length of G2 period was determined by the time of the first detectable BrdU signal on prophase chromosomes and by the labelled mitoses method [Qastler et al. (1959) *Exp. Cell Res.* 17:420–438]. The length of the S-phase was determined in three ways: (i) on the basis of the length of cell cycle and the fraction of nuclei labelled during the 30–120 min pulse; (ii) by measuring the time between the very end of the replication of the extreme late replicating chromosomes and the detection of the first signal on the chromosomes at the beginning of S phase; (iii) by the labelled mitoses method.

In repeated experiments, the duration of the cell cycle was found to be 22–26 h, the S phase 10–14 h, and the G2 phase 3.5–4.5 h.

Analyses of the replication of the megachromosome were made in parallel cultures by collecting mitotic cells at two hour intervals following two hours of colchicine treatment. In a repeat experiment, the same analysis was performed using one hour sample intervals and one hour colchicine treatment. Although the two procedures gave comparable results, the two hour sample intervals were viewed as more appropriate since approximately 30% of the cells were found to have a considerably shorter or longer cell cycle than the average. The characteristic replication patterns of the individual chromosomes, especially some of the late replicating hamster chromosomes, served as useful internal markers for the different stages of S-phase. To minimize the error caused by the different lengths of cell cycles in the different experiments, samples were taken and analyzed throughout the whole cell cycle until the appearance of the first signals on one chromatid at the beginning of the second S-phase.

The sequence of replication in the megachromosome is as follows. At the very beginning of the S-phase, the replication of megachromosome starts at the ends of the chromosomes. The first initiation of replication in an interstitial position can usually be detected at the centromeric region. Soon after, but still in the first quarter of the S-phase, when the terminal region of the short arm has almost completed its replication, discrete initiation signals appear along the chromosome arms. In the second quarter of the S-phase, as replication proceeds, the BrdU-labelled zones gradually widen, and the checkered pattern of the megachromosome becomes clear [see, e.g., FIG. 2F]. At the same time, pericentric regions of mouse chromosomes also show intense incorporation of BrdU. The replication of the megachromosome peaks at the end of the second quarter and in the third quarter of the S-phase. At the end of the third quarter, and at the very beginning of the last quarter of the S-phase, the megachromosome and the pericentric heterochromatin of the mouse chromosomes complete their replication. By the end of S-phase only the very late replicating segments of mouse and hamster chromosomes are still incorporating BrdU.

The replication of the whole genome occurs in distinct phases. The signal of incorporated BrdU increased continuously until the end of the first half of the S-phase, but at the beginning of the third quarter of the S-phase chromosome segments other than the heterochromatic regions hardly incorporated BrdU. In the last quarter of the S-phase, the BrdU signals increased again when the extreme late replicating segments showed very intense incorporation.

Similar analyses of the replication in mouse A9 cells were performed as controls. To increase the resolution of the immunolabelling pattern, pericentric regions of A9 chromosomes were decondensed by treatment with Hoechst 33258. Because of the intense replication of the surrounding euchromatic sequences, precise localization of the initial BrdU signal in the heterochromatin was normally difficult, even on undercondensed mouse chromosomes. On those chromosomes where the initiation signal(s) were localized unambiguously, the replication of the pericentric heterochromatin of A9 chromosomes was similar to that of the megachromosome. Chromosomes of A9 cells also exhibited replication patterns and sequences similar to those of the mouse chromosomes in the hybrid cells. These results indicate that the replicators of the megachromosome and mouse chromosomes retained their original timing and specificity in the hybrid cells.

By comparing the pattern of the initiation sites obtained after BrdU incorporation with the location of the integration sites of the "foreign" DNA in a detailed analysis of the first quarter of the S-phase, an attempt was made to identify origins of replication (initiation sites) in relation to the amplicon structure of the megachromosome. The double band of integrated DNA on the long arm of the megachromosome served as a cytological marker. The results showed a colocalization of the BrdU and in situ hybridization signals found at the cytological level, indicating that the "foreign" DNA sequences are in close proximity to the origins of replication, presumably integrated into the non-satellite sequences between the replicator and the satellite sequences [see, FIG. 3]. In the pericentric region of several other chromosomes, dot-like BrdU signals can also be observed that are comparable to the initiation signals on the megachromosome. These signals may represent similar initiation sites in the heterochromatic regions of normal chromosomes.

At a frequency of $10^{-4}$, "uncontrolled" amplification of the integrated DNA sequences was observed in the megachromosome. Consistent with the assumption (above) that "foreign" sequences are in the proximity to the replicators, this spatially restricted amplification is likely to be a consequence of uncontrolled repeated firings of the replication origin(s) without completing the replication of the whole segment.

C. Discussion

It has generally been thought that the constitutive heterochromatin of the pericentric regions of chromosomes is late replicating [see, e.g., Miller (1976) *Chromosoma* 55:165–170]. On the contrary, these experiments evidence that the replication of the heterochromatic blocks starts at a discrete initiation site in the first half of the S-phase and continues through approximately three-quarters of S-phase. This difference can be explained in the following ways: (i) in normal chromosomes, actively replicating euchromatic sequences that surround the satellite DNA obscure the initiation signals, and thus the precise localization of initiation sites is obscured; (ii) replication of the heterochromatin can only be detected unambiguously in a period during the second half of the S-phase, when the bulk of the heterochromatin replicates and most other chromosomal regions have already completed their replication, or have not yet started it. Thus, low resolution cytological techniques, such as analysis of incorporation of radioactively labelled precursors by autoradiography, only detect prominent replication signals in the heterochromatin in the second half of S-phase, when adjacent euchromatic segments are no longer replicating.

In the megachromosome, the primary initiation sites of replication colocalize with the sites where the "foreign" DNA sequences are integrated at the amplicon borders. Similar initiation signals were observed at the same time in the pericentric heterochromatin of mouse chromosomes that do not have "foreign" DNA, indicating that the replication initiation sites at the borders of amplicons may reside in the non-satellite flanking sequences of the satellite DNA blocks. The presence of a primary initiation site at each satellite DNA doublet implies that this large chromosome segment is a single huge unit of replication [megareplicon] delimited by the primary initiation site and the termination point at each end of the unit. Several lines of evidence indicate that, within this higher-order replication unit, "secondary" origins and replicons contribute to the complete replication of the megareplicon:

1. The total replication time of the heterochromatic regions of the megachromosome was ~9–11 h. At the rate of movement of replication forks, 0.5–5 kb per minute, that is typical of eukaryotic chromosomes [Kornberg et al. (1992) *DNA Replication.* 2nd. ed., New York: W. H. Freeman and Co, p. 474], replication of a ~15 Mb replicon would require 50–500 h. Alternatively, if only a single replication origin was used, the average replication speed would have to be 25 kb per minute to complete replication within 10 h. By comparing the intensity of the BrdU signals on the euchromatic and the heterochromatic chromosome segments, no evidence for a 5- to 50-fold difference in their replication speed was found.

2. Using short BrdU pulse labelling, a single origin of replication would produce a replication band that moves along the replicon, reflecting the movement of the replication fork. In contrast, a widening of the replication zone that finally gave rise to the checkered pattern of the megachromosome and within the replication period the most intensive BrdU incorporation occurred in the second half of the S-phase was observed. This suggests that once the megareplicator has been activated, it permits the activation and firing of "secondary" origins, and that the replication of the bulk of the satellite DNA takes place from these "secondary" origins during the second half of the S-phase. This is supported by the observation that in certain stages of the replication of the megachromosome, the whole amplicon can apparently be labelled by a short BrdU pulse.

Megareplicators and secondary replication origins seem to be under strict temporal and spatial control. The first initiation within the megachromosomes usually occurred at the centromere, and that shortly afterward all the megareplicators become active. The last segment of the megachromosome to complete replication was usually the second segment of the long arm. Results of control experiments with mouse A9 chromosomes indicate that replication of the heterochromatin of mouse chromosomes corresponds to the replication of the megachromosome amplicons. Therefore, the pre-existing temporal control of replication in the heterochromatic blocks is preserved in the megachromosome. Positive [Hassan et al. (1994) *J. Cell. Sci.* 107:425–434] and negative [Haase et al. (1994) *Mol. Cell. Biol.* 14:2516–2524] correlations between transcriptional activity and initiation of replication have been proposed. In the megachromosome, transcription of the integrated genes seems to have no effect on the original timing of the replication origins. The concerted, precise timing of the megareplicator initiations in the different amplicons suggests the presence of specific, cis-acting sequences, origins of replication.

Considering that pericentric heterochromatin of mouse chromosomes contains thousands of short, simple repeats spanning 7–15 Mb, and the centromere itself may also contain hundreds of kilobases, the existence of a higher-order unit of replication seems probable. The observed uncontrolled intrachromosomal amplification restricted to a replication initiation region of the megachromosome is highly suggestive of a rolling-circle type amplification, and provides additional evidence for the presence of a replication origin in this region.

The finding that a specific replication initiation site occurs at the boundaries of amplicons suggests that replication might play a role in the amplification process. These results suggest that each amplicon of the megachromosome can be regarded as a huge megareplicon defined by a primary initiation site [megareplicator] containing "secondary" origins of replication. Fusion of replication bubbles from different origins of bi-directional replication [DePamphilis (1993) *Ann. Rev. Biochem.* 62:29–63] within the megareplicon could form a giant replication bubble, which would correspond to the whole megareplicon. In the light of this, the formation of megabase-size amplicons can be accommodated by a replication-directed amplification mechanism. In both H and E-type amplifications, intrachromosomal multiplication of the amplicons was observed [see, above EXAMPLES], which is consistent with the unequal sister chromatid exchange model. Induced or spontaneous unscheduled replication of a megareplicon in the constitutive heterochromatin may also form new amplicon(s) leading to the expansion of the amplification or to the heterochromatic polymorphism of "normal" chromosomes. The "restoration" of the missing segment on the long arm of the megachromosome may well be the result of the re-replication of one amplicon limited to one strand.

Taken together, without being bound by any theory, a replication-directed mechanism is a plausible explanation for the initiation of large-scale amplifications in the centromeric regions of mouse chromosomes, as well as for the de novo chromosome formations. If specific [amplificator] sequences play a role in promoting the amplification process, sequences at the primary replication initiation site [megareplicator] of the megareplicon are possible candidates.

Preliminary sequence data indicates the presence of highly G+C -rich sequence elements less than 10 kb from the integrated heterologous "foreign" DNA in the megachromosome. These sequences may represent the non-satellite DNA flanking of the A+T-rich satellite DNA blocks.

EXAMPLE 9

Generation of Chromosomes with Amplified Regions Derived from Mouse Chromosome 1

To show that the events described in EXAMPLES 2–7 are not unique to mouse chromosome 7 and to show that the EC7/3 cell line is not required for formation of these chromosomes, the experiments have been repeated using different initial cell lines and DNA fragments. Any cell or cell line should be amenable to use or can readily be determined to be amenable or not.

A. Materials

The LP11 cell line was produced by the "scrape-loading" transfection method [Fechheimer et al. (1987) *Proc. Natl. Acad. Sci. U.S.A.* 84:8463–8467] using 25 $\mu$g plasmid DNA for 5×10$^6$ recipient cells. LP11 cells were maintained in F-12 medium containing 3–15 $\mu$g/ml Puromycin [SIGMA].

B. Amplification in LP11 cells

The large-scale amplification described in the above Examples is not restricted to the transformed EC3/7 cell line or to the chromosome 7 of mouse. In an independent transformation experiment, using a selectable puromycin construct pPuroTel, an LMTK$^-$ cell line [LP11] was established, carrying chromosome(s) with amplified chromosome segments of different lengths [~150–600 Mb]. Cytological analysis of the LP11 cells indicated that the amplification occurred in the pericentric region of the long arm of a submetacentric chromosome formed by Robertsonian translocation. This chromosome arm was identified by G-banding as chromosome 1. C-banding and in situ hybridization with mouse major satellite DNA probe showed that an E-type amplification had occurred: the newly formed region was composed of an array of euchromatic chromosome segments containing different amounts of heterochromatin. The size and C-band pattern of the amplified segments were heterogeneous. In several cells, the number of these amplified units exceeded 50; single-cell subclones of LP11 cell lines, however, carry stable marker chromosomes with 10–15 segments and constant C-band patterns.

EXAMPLE 10
Purification of Artificial Chromosomes
I. Cell Sorting Based on Base Composition and Size
    A. Cell Lines 1B3 mouse-hamster-human hybrid cells [see, FIG. 4] carrying the megachromosome or the truncated megachromosome were grown in F-12 medium supplemented with 10% fetal calf serum, 150 µg/ml hygromycin B and 400 µg/ml G418. GHB-42 [a cell line recloned from G3D5] mouse-hamster hybrid cells carrying the megachromosome and the mini-chromosome were cultured in F-12 medium containing 10% fetal calf serum, 150 µg/ml hygromycin B and 400 µg/ml G418. The doubling time of both cell lines was about 24 hours.

B. Chromosome Isolation

To accumulate mitotic cells, 5 µg/ml colchicine was added for 12 hours to the cultures. Mitotic cells were then harvested by gentle pipetting of the medium on the layer cells. The mitotic index obtained was 60–80%. The mitotic cells by were collected by selective detachment. The cells were sedimented by centrifugation of 200 g for 10 minutes.

Two procedures were used to prepare metaphase chromosomes from these cells, one based on polyamine buffer system. [Cram et al. (1990) *Methods in Cell Biology* 33:377–382] and the other on modified hexylene glycol buffer system [Hadlaczky et al. (1982) *Chromosoma* 86:643–65].

1. Polyamine procedure

In the polyamine procedure, about $10^7$ mitotic cells were incubated in 10 ml hypotonic buffer (75 mM KCl, 0.2 mM spermine, 0.5 mM spermidine) for 10 minutes at room temperature to swell the cells. The cells were then centrifuged at 100 g for 8 minutes. The cell pellet was drained carefully and about $10^7$ cells were resuspended in 1 ml polyamine buffer [15 mM Tris-HCl, 20 mM NaCl, 80 mM KCl, 2 mM EDTA, 0.5 mM EGTA, 14 mM β-mercaptoethanol, 0.1% digitonin, 0.2 mM Spermine, 0.5 mM spermidine]. Chromosomes were then released by gently drawing the cell suspension up and expelling it through a 22 G needle attached to a 3 ml plastic syringe. The chromosome concentration was about $1-3\times10^8$ chromosomes/ml.

2. Hexylene Glycol Buffer System

In the second procedure, about $8\times10^6$ mitotic cells were resuspended in 10 ml glycine-hexylene glycol buffer [100 mM glycine, 1% hexylene glycol, pH 8.4–8.6 adjusted with saturated Ca-hydroxide solution] and incubated for 10 minutes at 37° C., followed by centrifugation for 10 minutes to pellet the nuclei. The supernatant was centrifuged again at 200 g for 20 minutes to pellet the chromosomes. Chromosomes were resuspended in 1 ml isolation buffer/$1-3\times10^8$ chromosomes.

C. Staining of Chromosomes with DNA Specific Dyes

Subsequent to isolation, the chromosome preparation was stained with Hoechst 33258 at 6 µg/ml and chromocycin A3 at 200 µg/ml. Fifteen minutes prior to analysis, 25 mM Na-sulphite and 10 mM Na-citrate were added to the chromosome suspension.

D. Flow Sorting of Chromosomes

Chromosomes in suspension were passed through a dual-laser cell sorter [FACStar Plus and FAXStar Vantage Becton Dickinson Immunocytometry System] in which two lasers were set to excite the dyes separately, allowing a bivariate analysis of the chromosome by size and base-pair composition. Because of the difference between the base composition of the MACs and the other chromosomes and the resulting difference in interaction with the dyes, as well as size differences, the artificial chromosomes were separated from the other chromosomes.

E. Storage of the Sorted Artificial Chromosomes

The sorted chromosomes are stored in GH buffer (100 mM glycine, 1% hexylene glycol pH 8.4–8.6 adjusted with saturated Ca-hydroxide solution [see, e.g., Hadlaczky et al. (1982) *Chromosoma* 86:643–659] for one day and embedded by centrifugation into agarose. The sorted chromosomes were centrifuged into an agarose bed and the plugs are stored in 500 mM EDTA at 4° C. They are stored for microinjection in 30% glycerol at –20° C.

F. Quality Control

1. Analysis of the Purity

The purity of the sorted chromosomes was checked by fluorescence in situ hybridization (FISH) with biotin labeled mouse satellite DNA probe [see, Hadlaczky et al. (1991) *Proc. Natl. Acad. Sci. U.S.A.* 88:8106–8110. Purity of the sorted chromosomes was 97–99%.

2. Characteristics of the Sorted Chromosomes

Pulsed field gel electrophoresis and Southern hybridization were carried out to determine the size distribution of the DNA content of the sorted artificial chromosomes.

C. Functioning of the Artificial Chromosomes

To check whether their activity is preserved, the artificial chromosomes are microinjected into primary cells, somatic cells and stem cells.

II. Sorting of Mammalian Artificial Chromosome Containing Microcells

A. Micronucleation

Cells were growns to 80–90% confluency in 4 T150 flasks. Colcemid was added to a final concentration of 0.06 µg/ml, and then incubated with the cells at 37° C. for 24 hours.

B. Enucleation

Ten µg/ml cytochalasin B was added and the resulting microcells were centrifuged the at 15,000 rpm for 70 minutes at 28–33° C.

C. Purification of Microcells by Filtration

The microcells were purified using Swinnex filter units and Nucleopore filters [5 µm and 3 µm].

D. Staining and Sorting Microcells

As above, the cells were stained Hoechst and chromomycin A3 dyes. The microcells were sorted by cell sorter to isolate the microcells that contain the mammalian artificial chromosome.

E. Fusion

The microcells that contain the artificial chromosome are fused to selected primary cells, somatic cells, embryonic stem cells to generate transgenic animals for gene therapy purposes, and other cells to deliver the chromosomes to the cells.

EXAMPLE 11
Introduction of Mammalian Artificial Chromosomes into Insect Cells Insect cells should be useful hosts for MACs, particularly for production of gene products for a number of reasons, including:

1. A mammalian artificial chromosome provides extra genomic specific integration site for introduction of genes encoding proteins of interest [reduced chance of mutation in production system].

2. The large size of artificial chromosome permits megabase size DNA integration so that genes encoding an entire pathway leading to a protein or nonprotein of therapeutic value, such as an alkaloid [digitalis, morphine, taxol].

3. Amplification of genes encoding useful proteins can be accomplished in the artificial mammalian chromosome to obtain higher protein yields in insect cells.

4. Insect cells support required post translational modifications (glycosylation, phosphorylation) essential for protein biological function.

5. Insect cells do not support mammalian viruses—eliminates cross-contamination of product with human infectious agents.

6. The ability to introduce chromosomes, circumvents traditional recombinant baculovirus systems for production of nutritional, industrial or medicinal proteins in insect cell systems.

7. The low temperature optimum for insect cell growth (28° C.) permits reduced energy cost of production.

8. Serum free growth medium for insect cells will result in lower production costs.

9. Artificial chromosome containing cells can be stored indefinitely at low temperature.

10. Insect larvae will serve as biological factories for the production of nutritional, medicinal or industrial proteins by microinjection of fertilized insect eggs.

A. Demonstration that Insect Cells Recognize Mammalian Promoters

Gene constructs containing a mammalian promoter, such as CMV linked to DNA encoding a detectable marker gene fusions [Renilla luciferase gene (see, e.g., U.S. Pat. No. 5,292,658 for a description of DNA encoding the Renilla luciferase, and plasmid pTZrLuc-1, which can provide the starting material for construction of such vectors, see SEQ ID No. 10] and also including the simian virus 40 (SV40) promoter operably linked to the beta galactosidase gene] was introduced into the cells of two species *Trichoplusia ni* [cabbage looper] and *Bombyx mori* [silk worm].

After transferring the constructs into the insect cell lines either by electroporation or by microinjection, expression of the marker genes was detected after a 24 h incubation. In each case a positive result was obtained in the samples containing the genes which was absent in samples in which the genes were omitted. In addition, a β-actin promoter—Renilla luciferase fusion was introduced into the *T. ni* and *B. mori* cells yielding light emission. Thus, mammalian promoters function to direct expression of these marker genes in insects. Therefore, MACs are candidates for expression of heterologous genes in insect cells.

B. Construction of Vectors for Use in Insect Cells and Fusion with Mammalian Cells 1. Transform LMTK⁻ cells with expression vector with:
    a. *B. mori* β-actin promoter—Hyg$^r$ selectable marker gene for insect cells, and.
    b. SV40 or CMV promoters controlling a puromycin$^r$ selectable marker gene for mammalian cells.
2. Detect expression of the mammalian promoter in LMTk cells (puromycin$^r$ LMTk cells)
3. Use pur$^r$ cells in fusion experiments with Bombyx and Trichoplusia cells, select Hyg$^r$ cells.

C. Insertion of the MACs into Insect Cells

These experiments are designed to detect expression of a detectable marker gene [such as β-gal expressed under the control of a mammalian promoter, such as pSV40 ] located on a MAC. Data indicate that β-gal was expressed.

Insect cells of each species are fused with mammalian cells containing either the mini chromosome [EC3/7C5 ] or the mini and the megachromosome [such as GHB-42, which is a cell line recloned from G3D5] or a cell line that carries only the megachromosome [such as H1D3 or a redone therefrom]. Fusion is carried out as follows:

1. mammalian+insect cells (50/50%) in log phase growth are mixed;
2. calcium/PEG cell fusion: (10 min –0.5 h);
3. heterokaryons (+72 h) are selected.

The following selection conditions to select for insect cells that contain a MAC can be used: [+=positive selection;–=negative selection]:

1. growth at 28° C. (+insect cells, –mammalian cells);
2. Graces insect cell medium [SIGMA] (–mammalian cells);
3. no exogenous CO2 (–mammalian cells); and/or
4. antibiotic selection (Hyg or G418) (+transformed insect cells).

Immediately following the fusion protocol, many heterokaryons [fusion events] are observed between the mammalian and each species of insect cells [up to 90% heterokaryons]. After growth [2+weeks] on insect medium containing G418 and/or hygromycin at selection levels used for selection of transformed mammalian cells, individual colonies are detected growing on the fusion plates. By virtue of selection for the antibiotic resistance conferred by the MAC and selection for insect cells, these colonies should contain MACs.

EXAMPLE 12

Preparation of the Chromosome Fragmentation Vector and Other Vectors for Targeted Integration of DNA into MACs Fragmentation of the megachromosome, should ultimately result in smaller stable chromosomes that contain about 15 Mb to 50 Mb that will be easily manipulated for use as vectors. Vectors to effect such fragmentation should also aid in determination and identification of the elements required for preparation of an in vitro-produced artificial chromosome.

Reduction in the size of the megachromosome can be achieved in a number of different ways including: stress treatment, such as by starvation, or cold or heat treatment; treatment with agents that destabilize the genome or nick DNA, such as BrdU, coumarin, EMS and others; treatment with ionizing radiation [see, e.g., Brown (1992) *Curr. Opin. Genes Dev.* 2:479–486]; and telomere-directed in vivo chromosome fragmentation [see, e.g., Far et al. (1995) *EMBO J.* 14:5444–5454].

A. Preparation Vectors for Fragmentation of the Artificial Chromosome and also for Targeted Integration of Selected Gene Products 1. Construction of pTEMPUD Plasmid pTEMPUD [see, FIG. 5] is a mouse homologous recombination "killer" vector for in vivo chromosome fragmentation, and also for inducing large-scale amplification via site specific integration. With reference to FIG. 5, the PstI to SalI fragment was derived from pBabe-puro retroviral vector [see, Morgenstern et al. (1990) *Nucleic Acids Res.* 18:3587–3596]. This fragment contains DNA encoding ampicillin resistance, the pUC origin of replication, and the puromycin N-acetyl transferase gene under control of the SV40 early promoter. The URA3 portion comes from the pYAC5 cloning vector [SIGMA]. URA3 was cut out of pYAC5 with SalI-XhoI digestion, cloned into pNEB193 [New England Biolabs], which was then cut with EcoRI-SalI and ligated to the SalI site of pBabepuro to produce pPU.

A 1293 bp fragment [see SEQ ID No. 1] encoding the mouse major satellite, was isolated as an EcoRI fragment from a DNA library produced from mouse LMTK⁻ fibroblast cells and inserted into the EcoRI site of pPU to produce pMPU.

The TK promoter driven diphtheria toxin gene [DT-A] was derived from pMC1DT-A [see, Maxwell et al. (1986) *Cancer Res.* 46:4660–4666] by BglII-XhoI digestion and cloned into the pMC1neo poly A expression vector [STRATAGENE, La Jolla, Calif.] by replacing the neo coding sequence. The TK promoter, DT-A gene and poly A sequence were removed from this vector, cohesive ends were filled with Klenow and the resulting fragment blunt end-ligated and ligated into the SnaB1 [TACGTA] of pMPU to produce pMPUD.

The Hutel 2.5 fragment [see SEQ ID No. 31 was inserted at the PstI site [see the 6100 PstI–3625 PstI fragment on PTEMPUD] of pMPUD to produce pTEMPUD. This fragment includes a human telomere. It includes a unique BglII site [see nucleotides 1042–1047 of SEQ ID No. 3], which will be used as a site for introduction of a synthetic telomere that will include multiple repeats [80] of GGGATT with BamHI and BglII ends for insertion into the BglII site which will then remain unique, since the BamHI overhang is compatible with the BglII site. Ligation of BamHI fragment to a BglII destroys the BglII site, so that only a single BglII site will remain. Selection for the unique BglII site insures that the synthetic telomere will be inserted in the correct orientation. The unique BglII site is the site at which the vector is linearized.

2. Use of pTEMPUD for in vivo Chromosome Fragmentation

Linearization of pTEMPUD by BglII results in a linear molecule with a human telomere at one end. Integration of this linear fragment into the chromosome, such as the megachromosome in hybrid cells or any mouse chromosome, which is contains repeats of the mouse major satellite sequence, results integration of the selectable marker puromycin and cleavage of the plasmid by virtue of the telomeric end. The DT gene prevents that entire linear fragment from integrating by random events, since upon integration and expression it is toxic. Thus random integration will be toxic. Thus, site directed integration into the targeted DNA will be selected. Such integration will produce fragmented chromosomes.

The fragmented truncated chromosome with the new telomere will survive, and the other fragment without the centromere will be lost. Repeated in vivo fragmentations will ultimately result in selection of the smallest functioning minichromosome possible.

Thus this vector can be used to produce minichromosomes from mouse chromosomes, or to fragment the megachromosome.

3. pTEMPhu and pTEMPhu3

Vectors that specifically target human chromosomes can be constructed from pTEMPUD. These vectors can be used to fragment specific human chromosomes, depending upon the selected satellite sequence, to produce human minichromosomes, and also to isolate human centromeres.

a. pTEMPhu

To render pTEMPUD suitable for fragmenting human chromosomes, the mouse major satellite sequence is replaced with human satellite sequences. Unlike mouse chromosomes, each human chromosome has a unique satellite sequence. For example, the mouse major satellite has been replace with a human hexameric α-satellite [or alphoid satellite] DNA sequence. This sequence is an 813 bp fragment Inucleotide 232–1044 of SEQ ID No. 2] from clone pS12, deposited in the EMBL database under Accession number X60716, isolated from a human colon carcinoma cell line Colo320 [deposited under Accession No. ATCC CCL 220.1]. The 813 bp alphoid fragment can be obtained from the pS12 clone by nucleic acid amplification using synthetic primers, which each contain an EcoRI site, as follows:

GGGGAATTCAT TGGGATGTTT CAGTTGA forward primer [SEQ ID No. 4]
CGAAAGTCCCC CCTAGGAGAT CTTAAGGA reverse primer [SEQ ID No. 5].

Digestion of the amplified product with EcoRI results in a fragment with EcoRI ends that includes the human α-satellite sequence. This sequence is inserted into pTEMPUD in place of the EcoRI fragment that contains the mouse major satellite.

b. pTEMPhu3

In pTEMPhu3, the mouse major satellite sequence is replaced by the 3 kb human chromosome 3-specific α-satellite from D3Z1 [deposited under ATCC Accession No. 85434; see, also Yrokov (1989) Cytogenet. Cell Genet. 51:1114].

4. Use of the pTEMPHU3 to Induce Amplification on Human Chromosome #3

Each human chromosome contains unique chromosome-specific alphoid sequence. Thus, use of pTEMPHU3, which is targeted to the chromosome 3-specific α-satellite can be introduced into human cells under selective conditions, whereby large scale amplification of the chromosome 3 centromeric region and production of a de novo chromosome. Such induced large-scale amplification provides a means for inducing de novo chromosome formation and also for in vivo cloning of defined human chromosome fragments up to megabase size.

For example, the break-point in human chromosome #3 is on the short arm near the centromere. this region is involved in renal cell carcinoma formation. By targeting pTEMPhu3 to this region, the induced large-scale amplification may contain this region, which can then be cloned using the bacterial and yeast markers in the pTEMPhu3 vector.

The pTEMPhu3 cloning vector allows not only selection for homologous recombinants, but also direct cloning of the integration site in YACS. This vector can also be used to target human chromosome #3, preferably with a deleted short arm, in a mouse-human monochromosomal microcell hybrid line. Homologous recombinants can be screened by nucleic acid amplification (PCR) and amplification can be screened by DNA hybridization, Southern hybridization, and in situ hybridization. The amplified region can be cloned into YAC. This vector and these methods also permit a functional analysis of cloned chromosome regions by reintroducing the cloned amplified region into mammalian cells.

B. Preparation of Libraries in YAC Vectors for Cloning of Centromeres and Identification of Functional Chromosomal Units Another method that may be used to obtain smaller-sized functional mammalian artificial chromosome units and to clone centromeric DNA involves screening of mammalian DNA YAC vector-based libraries and functional analysis of potential positive clones in a transgenic mouse model system. A mammaliam DNA library is prepared in a YAC vector, such as YRT2 [see Schedl et al. (1993) Nuc. Acids Res. 21:4783–4787], which contains the murine tyrosinase gene. The library is screened for hybridization to mammalian telomere and centromere sequence probes. Positive clones are isolated and microinjected into pronuclei of fertilized oocytes of NMRI/Han mice following standard techniques. The embryos are then transferred into NMRI/Han foster mothers. Expression of the tyrosinase gene in transgenic offspring confers an identifiable phenotype (pigmentation). The clones that give rise to tyrosinase-expressing transgenic mice are thus confirmed as containing functional mammalian artificial chromosome units.

Alternatively, fragments of SATACs may be introduced into the YAC vectors and then introduced into pronuclei of fertilized oocytes of NMRI/Han mice following standard techniques as above. The clones that give rise to tyrosinase-expressing transgenic mice are thus confirmed as containing functional mammalian artificial chromosome units, particularly centromeres.

C. Incorporation of Heterologous Genes into Mammalian Artificial Chromosomes through The Use of Homology Targeting Vectors As described above, the use of mammalian artificial chromosomes for expression of heterologous genes obviates certain negative effects that may result from random integration of heterologous plasmid DNA into the recipient cell genome. An essential feature of the mammalian artificial chromosome that makes it a useful tool in avoiding the negative effects of random integration is its presence as an extra-genomic gene source in recipient cells. Accordingly, methods of specific, targeted incorporation of heterologous genes exclusively into the mammalian artificial chromosome, without extraneous random integration into the genome of recipient cells, are desired for heterologous gene expression from a mammalian artificial chromosome.

One means of achieving site-specific integration of heterologous genes into artificial chromosomes is through the use of homology targeting vectors. The heterologous gene of interest in subcloned into a targeting vector which contains nucleic acid sequences that are homologous to nucleotides present in the artificial chromosome. The vector is then introduced into cells containing the artificial chromosome for specific site-directed integration into the artificial chromosome through a recombination event at sites of homology between the vector and the chromosome. The homology targeting vectors may also contain selectable markers for ease of identifying cells that have incorporated the vector into the artificial chromosome as well as lethal selection genes that are expressed only upon extraneous integration of vector into the recipient cell genome. Two exemplary homology targeting vectors, λCF-7 and pλCF-7-DTA, are described below.

1. Construction of Vector λCF-7

Vector λCF-7 contains the cystic fibrosis transmembrane conductance regulator [CFTR] gene as an exemplary therapeutic moleculeencoding nucleic acid that may be incorporated into mammalian artificial chromosomes for use in gene therapy applications. This vector, which also contains the puromycin-resistance gene as a selectable marker, as well as the *Saccharomvces cerevisiae* ura3 gene [orotidine-5-phosphate decarboxylase], was constructed in a series of steps as follows.

a. Construction of pURA

Plasmid pURA was prepared by ligating a 2.6-kb SalI/XhoI fragment from the yeast artificial chromosome vector pYAC5 [Sigma; see also Burke et al. (1987) *Science* 236:806–812 for a description of YAC vectors as well as GenBank Accession no. U01086 for the complete sequence of pYAC5] containing the *S. cerevisiae* ura3 gene with a 3.3-kb SalI/SmaI fragment of pHyg [see, e.g., U.S. Pat. Nos. 4,997,764, 4,686,186 and 5,162,215, and the description above]. Prior to ligation the XhoI end was treated with Klenow polymerase for blunt end ligation to the SmaI end of the 3.3 kb fragment of pHyyg. Thus, pURA contains the *S. cerevisiae* ura3 gene, and the *E. coli* ColE1 origin of replication and the ampicillin-resistance gene. The uraE gene is included to provide a means to recover the integrated construct from a mammalian cell as a YAC clone.

b. Construction of pUP2

Plasmid pURA was digested with SalI and ligated to a 1.5-kb SalI fragment of pCEPUR. Plasmid pCEPUR is produced by ligating the 1.1 kb SnaBI-NhaI fragment of pBabe-puro [Morgenstern et al. (1990) *Nucl. Acids Res.* 18:3587–3596; provided by Dr. L. Székely (Microbiology and Tumorbiology Center, Karolinska Institutet, Stockholm); see, also Tonghua et al. (1995) *Chin. Med. J.* (Beijing, Engl. Ed.) 108:653–659; Couto et al. (1994) *Infect. Immun.* 62:2375–2378; Dunckley et al. (1992) *FEBS Lett.* 296:128–34; French et al. (1995) *Anal. Biochem.* 228:354–355; Liu et al. (1995) *Blood* 85:1095–1103; International PCT application Nos. WO 9520044; WO 9500178, and WO 9419456] to the NheI-NruI fragment of pCEP4 [Invitrogen].

The resulting plasmid, pUP2, contains the all the elements of pURA plus the puromycin-resistance gene linked to the SV40 promoter and polyadenylation signal from pCEPUR.

C. Construction of pUP-CFTR

The intermediate plasmid pUP-CFTR was generated in order to combine the elements of pUP2 into a plasmid along with the CFTR gene. First, a 4.5-kb SalI fragment of pCMV-CFTR that contains the CFTR-encoding DNA [see, also, Riordan et al. (1989) *Science* 245:1066–1073, U.S. Pat. No. 5,240,846, and Genbank Accession no. M28668 for the sequence of the CFTR gene] containing the CFTR gene only was ligated to XhoI-digested pCEP4 [Invitrogen and also described herein] in order to insert the CFTR gene in the multiple cloning site of the Epstein Barr virus-based (EBV) vector pCEP4 [Invitrogen, San Diego, Calif.; see also Yates et al. (1985) *Nature* 313:812–815; see, also U.S. Pat. No. 5,468,615] between the CMV promoter and SV40 polyadenylation signal. The resulting plasmid was designated pCEP-CFTR. Plasmid pCEP-CFTR was then digested with SalI and the 5.8-kb fragment containing the CFTR gene flanked by the CMV promoter and SV40 polyadenylation signal was ligated to SalI-digested pUP2 to generate pUP-CFTR. Thus, pUP-CFTR contains all elements of pUP2 plus the CFTR gene linked to the CMV promoter and SV40 polyadenylation signal.

d. Construction of λCF-7

Plasmid pUP-CFTR was then linearized by partial digestion with EcoRI and the 13 kb fragment containing the CFTR gene was ligated with EcoRI-digested Charon 4Aλ [see Blattner et al. (1977) *Science* 196:161; Williams and Blattner (1979) *J. Virol.* 29:555 and Sambrook et al. (1989) *Molecular Cloning, A Laboratory Manual,* Second Ed., Cold Spring Harbor Laboratory Press, Volume 1, Section 2.18, for descriptions of Charon 4Aλ]. The resulting vector, λCF8, contains the Charon 4Aλ bacteriophage left arm, the CFTR gene linked to the CMV promoter and SV40 polyadenylation signal, the ura3 gene, the puromycin-resistance gene linked to the SV40 promoter and polyadenylation signal, the thymidine kinase promoter [TK], the ColE1 origin of replicaton, the amplicillan resistance gene and the Charon 4Aλ bacteriophage right arm. The λCF8 construct was then digested with XhoI and the resulting 27.1 kb was ligated to the 0.4 kb XhoI/EcoRI fragment of pJBP86 [described below], containing the SV40 polyA signal and the EcoRI-digested Charon 4A λ right arm. The resulting vector λCF-7 contains the Charon 4A λ left arm, the CFTR encoding DNA linked to the CMV promoter and SV40 polyA signal, the ura3 gene, the puromycin resistance gene linked to the SV40 promoter and polyA signal and the Charon 4A λ right arm. The λ DNA fragments provide sequences homologous to nucleotides present in the exemplary artificial chromosomes.

The vector is then introduced into cells containing the artificial chromosomes exemplified herein. Accordingly, when the linear λCF-7 vector is introduced into megachromosome-carrying fusion cell lines, such as described herein, it will be specifically integrated into the megachromosome through recombination between the homologous bacteriophage λ sequences of the vector and the artificial chromosome.

2. Construction of Vector λCF-7-DTA

Vector λCF-7-DTA also contains all the elements contained in λCF-7, but additionally contains a lethal selection marker, the diptheria toxin-A (DT-A) gene as well as the ampicillin-resistance gene and an origin of replication. This vector was constructed in a series of steps as follows.

a. Construction of pJBP86

Plasmid pJBP86 was used in the construction of λCF-7, above. A 1.5-kb SalI fragment of pCEPUR containing the puromycin-resistance gene linked to the SV40 promoter and polyadenylation signal was ligated to HindIII-digested pJB8 [see, e.g., Ish-Horowitz et al. (1981) Nucleic Acids Res. 9:2989–2998; available from ATCC as Accession No. 37074; commercially available from Amersham, Arlington Heights, Ill.]. Prior to ligation the SalI ends of the 1.5 kb fragment of pCEPUR and th4 HindIII linearized pJB8 ends were treated with Klenow polymerase before ligation. The resulting vector pJBP86 contains the puromycin resistance gene linked to the SV40 promoter and polyA signal, the 1.8 kb COS region of Charon 4Aλ, the ColE1 origin of replication and the ampicillin resistance gene.

b. Construction of pMEP-DTA

A 1.1-kb XhoI/SalI fragment of pMC1-DT-A [see, e.g., Maxwell et al. (1986) Cancer Res. 46:4660–4666] containing the diptheria toxin-A gene was ligated to XhoI-digested pMEP4 [Invitrogen, San Diego, Calif.] to generate pMEP-DTA. To produce pMC1-DT-A, the coding region of the DTA gene was isolated as a 800 bp PstIHindIII fragment from p2249-1 and inserted into pMC1neopolyA [pMC1 available from Stratagene] in place of the neo gene and under the control of the TK promotoer. The resulting construct pMC1DT-A was digested with HindIII, the ends filled by Klenow and SalI linkers were ligated to produce a 1061 bp TK-DTA gene cassette with an XhoI end [5'] and a SalI end containing the 270 bp TK promoter and the ~790 bp DT-A fragment. This fragment was ligated into XhoI-digested pMEP4.

Plasmid pMEP-DTA thus contains the DT-A gene linked to the TK promoter and SV40, ColE1 origin of replication and the ampicillin-resistance gene.

C. Construction of pJB83-DTA9

Plasmid pJB8 was digested with HindIII and ClaI and ligated with an oligonucleotide [see SEQ ID NOs. 7 and 8 for the sense and antisense strands of the oligonucleotide, respectively] to generate pJB83. The oligonucleotide that was ligated to ClaI/HindIII-digested pJB8 contained the recognition sites of SwaI, PacI and SrfI restriction endonucleases. These sites will permit ready linearization of the pλCF-7-DTA construct.

Next, a 1.4-kb XhoI/SalI fragment of pMEP-DTA, containing the DT-A gene was ligated to SalI-digested pJB83 to generate pJB83-DTA9.

d. Construction of λCF-7-DTA

The 12-bp overhangs of λCF-7 were removed by Mung bean nuclease and subsequent T4 polymerase treatments. The resulting 41.1-kb linear λCF-7 vector was then ligated to pFB83-DTA9 which had been digested with ClaI and treated with T4 polymerase. The resulting vector, λCF-7-DTA, contains all the elements of λCF-7 as well as the DT-A gene linked to the TK promoter and the SV40 polyadenylation signal, the 1.8 kB Charon 4A λ COS region, the ampicdlin-resistance gene[from pJB83-DTA9] and the Col E1 origin of replication [from pJB83-DT9A].

3. pMCT-RUC,

Plasmid pMCT-RUC [14 kbp] was constructed for site-specific targeting of the Renilla luciferase [see, e.g., U.S. Pat. Nos. 5,292,658 and 5,418,155 for a description of DNA encoding Renilla luciferase, and plasmid pTZrLuc-1, which can provide the starting material for construction of such vectors] gene to a mammalian chromosome. The relevant features of this plasmid are the Renilla luciferase gene under transcriptional control of the human cytomegalovirus immediate-early gene enhancer/promoter; the hygromycin gene under the transcriptional control of the thymidine kinase promoter; and a unique HpaI site is for linearizing the plasmid.

This construct was introduced into C5 cells [see, Lorenz et al. (1996) J. Biolum. Chemilum. 11:31–37]. C5 mouse fibroblasts were maintained as a monolayer [see, Gluzman (1981) Cell 23:175–183]. Cells at 50% confluency in 100 mm Petri dishes were used for calcium phosphate transfection [see, Harper et al. (1981) Chromosoma 83:431–439] using 10 μg of linearized pMCT-RUC per plate. Colonies originating from single transfected cells were isolated and maintained in F-12 medium containing hygromycin (300 μg/mL) and 10% fetal bovine serum. Cells were grown in 100 mm Petri dishes prior to the Renilla luciferase assay.

The Renilla luciferase assay was performed [see, e.g., Matthews et al. (1977) Biochemistry 16:85–91]. Hygromycin-resistant cell lines obtained after transfection of mouse fibroblasts with linearized plasmid pMCT-RUC ["B" cell lines] were grown to 100% confluency for measurements of light emission in vivo and in vitro. Light emission was measured in vivo after about 30 generations as follows: growth medium was removed and replaced by 1 mL RPMI 1640 containing coelenterazine [1 mmol/L final concentration]. Light emission from cells was then visualized by placing the Petri dishes in a low light video image analyzer [Hamamatsu Argus-100]. An image was formed after 5 min. of photon accumulation using 100% sensitivity of the photon counting tube. For measuring light emission in vitro, cells were trypsinized and harvested from one Petri dish, pelleted, resuspended in 1 mL assay buffer [0.5 mol/L NACl, 1 mmol/L EDTA, 0.1 mol/L potassium phosphate, pH 7.4] and sonicated on ice for 10 s. Lysates were than assayed in a Turner TD-20e lukminometer for 10 s after rapid injection of 0.5 mL of 1 mmol/L coelenterazine, and the average value of light emission was recorded as LU [1 LU=1.6×106 hu/s for this instrument].

Independent cell lines of mouse fibroblasts transfected with linearized plasmid pMCT-RUC showed different levels of Renilla luciferase activity. Similar differences in light emission were observed when measurements were performed on lysates of the same cell lines. This variation in light emission was probably due to a position effect resulting from the random integration of plasmid pMCT-RUC into the mouse genome, since enrichment for site targeting of the luciferase gene was not performed in this experiment.

D. Protein Secretion Targeting Vectors

Isolation of heterologous proteins produced intracellularly in mammalian cell expression systems requires cell disruption under potentially harsh conditions and purification of the recombinant protein from cellular contaminants. The process of protein isolation may be greatly facilitated by secretion of the recombinantly produced protein into the extracellular medium where there are fewer contaminants to remove during purification. Therefore, secretion targeting vectors have been constructed for use with the mammalian artificial chromosome system.

A useful model vector for demonstrating production and secretion of heterologous protein in mammalian cells contains DNA encoding a readily detectable reporter protein fused to an efficient secretion signal that directs transport of the protein to the cell membrane and secretion of the protein from the cell. Vectors pLNCX-ILRUC and pLNCX-ILRUCλ, described below, are examples of such vectors. These vectors contain DNA encoding an interleukin-2 (IL2) signal peptide-*Renilla reniformis* luciferase fusion protein. The IL-2 signal peptide [encoded by the sequence set forth in SEQ ID No. 9] directs secretion of the luciferase protein, to which it is linked, from mammalian cells. Upon secretion from the host mammalian cell, the IL-2 signal peptide is cleaved from the fusion protein to deliver mature, active, luciferase protein to the extracellular medium. Successful production and secretion of this heterologous protein can be readily detected by performing luciferase assays which measure the light emitted upon exposure of the medium to the bioluminescent luciferin substrate of the luciferase enzyme.

1. Construction of Protein Secretion Vector pLNCX-ILRUC

Vector pLNCX-ILRUC contains a human IL-2 signal peptide-*R. reniformis* fusion gene linked to the human cytomegalovirus (CMV) immediate early promoter for constitutive expression of the gene in mammalian cells. The construct was prepared as follows.

a. Preparation of the IL-2 Signal Sequence-encoding DNA

A 69-bp DNA fragment containing DNA encoding the human IL-2 signal peptide was obtained through nucleic acid amplification, using appropriate primers for IL-2, of an HEK 293 cell line [see, e.g., U.S. Pat. No. 4,518,584 for an IL-2 encoding DNA; see, also SEQ ID No. 9; the IL-2 gene and corresponding amino acid sequence is also provided in the Genbank Sequence Database as accession nos. K02056 and J00264]. The signal peptide includes the first 20 amino acids shown in the translations provided in both of these Genbank entries and in SEQ ID NO. 9. The corresponding nucleotide sequence encoding the first 20 amino acids is also provided in these entries [see, e.g., nucleotides 293–52 of accession no. K02056 and nucleotides 478–537 of accession no. J00264], as well as in SEQ ID NO. 9. The amplification primers included an EcoRI site [GAATTC] that for subcloning of the DNA fragment into EcoRI-digested pGEMT [Promega]. The forward primer is set forth in SEQ ID No. 11 and the sequence of the reverse primer is set forth in SEQ ID No. 12.

TTTGAATTCATGTACAGGATGCAACTCCTG forward [SEQ ID No. 11]

TTTGAATTCAGTAGGTGCACTGTTTGTGAC reverse [SEQ ID No. 12]

b. Preparation of the *R. reniformis* Luciferase-encoding DNA

The initial source of the *R. reniformis* luciferase gene was plasmid pLXSN-RUC. Vector pLXSN [see, e.g., U.S. Pat. Nos. 5,324,655, 5,470,730, 5,468,634, 5,358,866 and Miller et al. (1989) *Biotechniques* 7:980] is a retroviral vector capable of expressing heterologous DNA under the transcriptional control of the retroviral LTR; it also contains the neomycin-resistance gene operatively linked for expression to the SV40 early region promoter. The *R. reniformis* luciferase gene was obtained from plasmid pTZrLuc-1 [see, e.g., U.S. Pat. No. 5,292,658; see also the Genbank Sequence Database accession no. M63501; and see also Lorenz et al. (1991) *Proc. Natl. Acad. Sci. U.S.A.* 88:4438–4442] and is shown as SEQ ID NO. 10. The 0.97 kb EcoRI/SmaI fragment of pTZrLuc-1 contains the coding region of the Renilla luciferase-encodig DNA. Vector pLXSN was digested with and ligated with the luciferase gene contained on a pLXSN-RUC, which contains the luciferase gene located operably linked to the viral LTR and upstream of the SV40 promoter, which directs expression of the neomycin-resistance gene.

c. Fusion of DNA encoding the IL-2 Signal Peptide and the *R. reniformis* Luciferase Gene to Yield pLXSN-ILRUC The pGEMT vector containing the IL-2 signal peptide-encoding DNA described in 1.a. above was digested with EcoRI, and the resulting fragment encoding the signal peptide was ligated to EcoRI-digested pLXSN-RUC. The resulting plasmid, called pLXSN-ILRUC, contains the IL-2 signal peptide-encoding DNA located immediately upstream of the *R. reniformis* gene in pLXSN-RUC. Plasmid pLXSN-ILRUC was then used as a template for nucleic acid amplification of the fusion gene in order to add a SmaI site at the 3' end of the fusion gene. The amplification product was subcloned into EcoRI/SmaI-digested pGEMT (Promega) to generate ILRUC-pGEMT.

d. Introduction of the Fusion Gene into a Vector Containing Control Elements for Expression in Mammalian Cells Plasmid ILRUC-pGEMT was digested with KspI and SmaI to release a fragment containing the IL-2 signal peptide-luciferase fusion gene which was ligated to HpaI-digested pLNCX. Vector pLNCX [see, e.g., U.S. Pat. Nos. 5,324,655 and 5,457,182; see, also Miller and Rosman (1989) *Biotechnigues* 7:980–990] is a retroviral vector for expressing heterologous DNA under the control of the CMV promoter; it also contains the neomycin-resistance gene under the transcriptional control of a viral promoter. The vector resulting from the ligation reaction was designated pLNCX-ILRUC. Vector pLNCX-ILRUC contains the IL-2 signal peptide-luciferase fusion gene located immediately downstream of the CMV promoter and upstream of the viral 3' LTR and polyadenylation signal in pLNCX. This arrangement provides for expression of the fusion gene under the control of the CMV promoter. Placement of the heterologous protein-encoding DNA [i.e., the luciferase gene] in operative linkage with the IL-2 signal peptide-encoding DNA provides for expression of the fusion in mammalian cells transfected with the vector such that the heterologous protein is secreted from the host cell into the extracellular medium.

2. Construction of Protein Secretion Targeting Vector pLNCX-ILRUCλ

Vector pLNCX-ILRUC may be modified so that it can be used to introduce IL-2 signal peptide-luciferase fusion gene into a mammalian artificial chromosome in a host cell. To facilitate specific incorporation of the pLNCX-ILRUC expression vector into a mammalian artificial chromosome, nucleic acid sequences that are homologous to nucleotides present in the artificial chromosome are added to the vector to permit site directed recombination.

Exemplary artificial chromosomes described herein contain lambda phage DNA. Therefore, protein secretion targeting vector pLNCX-ILRUCλ was prepared by addition of lambda phage DNA [from Charon 4A arms] to produce the secretion vector pLNCX-ILRUC.

3. Expression and Secretion of *R. reniformis* Luciferase from Mammalian Cells a. Expression of *R. reniformis* Luciferase Using pLNCX-ILRUC Mammalian cells [LMTK⁻ from the ATCC] were transiently transfected with vector pLNCX-ILRUC [~10 μg] by electroporation [BIORAD, performed according to the manufacturer's instructions]. Stable transfectants produced by growth in G418 for neo selection have also been prepared.

Transfectants were grown and then analyzed for expression of luciferase. To determine whether active luciferase was secreted from the transfected cells, culture media were assayed for luciferase by addition of coelentrazine [see, e.g., Matthews et al. (1977) *Biochemistry* 16:85–91].

The results of these assays establish that vector pLNCX-ILRUC is capable of providing constitutive expression of heterologous DNA in mammalian host cells. Furthermore, the results demonstrate that the human IL-2 signal peptide is capable of directing secretion of proteins fused to the C-terminus of the peptide. Additionally, these data demonstrate that the *R. reniformis* luciferase protein is a highly effective reporter molecule, which is stable in a mammalian cell environment, and forms the basis of a sensitive, facile assay for gene expression.

b. Expression of *R. reniformis* Luciferase Using pLNCX-ILRUCλ

To express the IL-2 signal peptide-*R. reniformis* fusion gene from an artificial mammalian chromosome, vector pLNCX-ILRUCλ is targeted for site-specific integration into an artificial mammalian chromosome through homologous recombination of the lambda DNA sequences contained in the chromosome and the vector. This is accomplished by introduction of pLNCX-ILRUCλ into either a fusion cell line harboring mammalian artificial chromosomes or mammalian host cells that contain artificial mammalian chromosomes. If the vector is introduced into a fusion cell line harboring the artificial chromosomes, for example through microinjection of the vector or transfection of the fusion cell line with the vector, the cells are then grown under selective conditions, i.e. artificial chromosomes, which have incorporated vector pLNCX-ILRUCλ, are isolated from the surviving cells, using purification procedures as described above, and then injected into the mammalian host cells.

Alternatively, the mammalian host cells may first be injected with mammalian artificial chromosomes which have been isolated from a fusion cell line. The host cells are then transfected with vector pLNCX-ILRUCλ and grown.

The recombinant host cells are then assayed for luciferase expression as described above.

D. Other Targeting Vectors

These vector rely on positive and negative selection to insure insertion and selection for the double recombinants. A single crossover results in incorporation of the DT-A, which kills the cell, double crossover recombinations delete the DT-1 gene.

1. Plasmid pNEM1 contains:

DT-A: Diphtheria toxin gene (negative selectable marker)
Hyg: Hygromycin gene (positive selectable marker)
ruc: Renilla luciferase gene (non-selectable marker)
1: LTR-MMTV promoter
2: TK promoter
3: CMV promoter
MMR: Homology region (plasmid pAG60)

2. plasmid pNEM-2 and -3 are similar to pNEM 1 except for different negative selectable markers:

pNEM-1: diphtheria toxin gene as "-" selectable marker
pNEM-2: hygromycin antisense gene as "-" selectable marker
pNEM-3: thymidine kinase HSV-1 gene as "-" selectable marker 3. Plasmid—lambda DNA based homology:

pNEMλ-1: base vector
pNEMλ-2: base vector containing p5=gene
1: LTR MMTV promoter
2: SV40 promoter
3: CMV promoter
4: μTIIA promoter (metallothionein gene promoter)— homology region (plasmid pAG60)

λ L.A. and λ R.A. homology regions for λ left and right arms (λ gt-WES).

EXAMPLE 13

Microinjection of Mammalian Cells with Plasmid DNA

These procedure will be used to microinject MACS into eukaryotic cells, including mammalian and insect cells.

The microinjection technique is based on the use of small glass capillaries as a delivery system into cells and has been used for introduction of DNA fragments into nuclei [see, e.g., Chalfie et al. (1994) *Science* 263:802–804]. It allows the transfer of almost any type of molecules, e.g., hormones, proteins, DNA and RNA, into either the cytoplasm or nuclei of recipient cells This technique has no cell type restriction and is more efficient than other methods, including $Ca^{2+}$-mediated gene transfer and liposome-mediated gene transfer. About 20–30% of the injected cells become successfully transformed.

Microinjection is performed under a phase-contrast microscope. A glass microcapillary, prefilled with the DNA sample, is directed into a cell to be injected with the aid of a micromanipulator. An appropriate sample volume (1–10 pl) is transferred into the cell by gentle air pressure exerted by a transjector connected to the capillary. Recipient cells are grown on glass slides imprinted with numbered squares for convenient localization of the injected cells.

a. Materials and Equipment

Nunclon tissue culture dishes 35×10 mm, Mouse cell line EC3/7C5 Plasmid DNA pCH110 [Pharmacia], Purified Green Florescent Protein (GFP) [GFPs from Aequorea and Renilla have been purified and also DNA encoding GFPs has been cloned; see, e.g., Prasher et al. (1992) *Gene* 111:229–233; International PCT Application No. WO 95/07463, which is based on U.S. application Ser. No. 08/119,678 and U.S. application Ser. No. 08/192,274], ZEISS Axiovert 100 microscope, Eppendorf transjector 5246, Eppendorf micromanipulator 5171, Eppendorf Cellocate coverslips, Eppendorf microloaders, Eppendorf femtotips and other standard equipment.

b. Protocol (1) Fibroblast cells are grown in Ø 35 mm tissue culture dishes (37° C., 5% $CO_2$) until the cell density reaches 80% confluency. The dishes are removed from the incubator and medium to added to about a 5 mm depth.

(2) The dish is placed onto the dish holder and the cells observed with 10× objective; the focus is desirably above the cell surface.

(3) Plasmid or chromosomal DNA solution [1 ng/μl] and GFP protein solution are further purified by centrifuging the DNA sample at force sufficient to removed any particular debris [typically about 10,000 rpm for 10 minutes in a microcentrifuge].

(4) Two 2 μl of the DNA solution (1 ng/μl) is loaded into a microcapillary with an Eppendorf microloader. During loading, the loader is inserted to the tip end of the microcapillary. GFP (1 mg/ml) is loaded wit the same procedure.

(5) The protecting sheath is removed from the microcapillary and the microcapillary is fixed onto the capillary holer connected with the micromanipulator.

(6) The capillary tip lowered to the surface of the medium and focus on the cells gradually until the tip of the capillary reaches the surface of a cell. Lower the capillary further so that the capillary is inserted into the cell. Various parameters, such as the level of the capillary, the time and pressure are determined for the particular equipment. For example, using the fibroblast cell line C5 and the above-noted equipment, the best conditions are: injection time 0.4 second, pressure 80 psi. DNA can then be automatically injected into the nuclei of the cells.

(7) After injection, the cells are returned to the incubator, and incubated for about 18–24 hours.

(8) After incubation the number of transformants can be determined by a suitable method, which depends upon the selection marker. For example, if green fluorescent protein is used, the assay can be performed using UV light source and fluorescent filter set at 0–24 hours after injection. If β-gal-containing DNA, such as DNA-derived from pHC110, has been injected, then the transformants can be assayed for β-gal.

i. Detection of β-galactosidase in cells injected with plasmid DNA. The medium is removed from the culture plate and the cells are fixed by addition of 5 ml of fixation Solution I: (1% glutaraldehyde; 0.1 M sodium phosphate buffer, pH 7.0; 1 mM $MgCl_2$), and incubated for 15 minutes at 37° C. Fixation Solution I is replaced with 5 ml of X-gal Solution II: [0.2% X-gal, 10 mM sodium phosphate buffer (pH 7.0), 150 mM NaCl, 1 mM $MgCl_2$, 3.3 mM $K_4Fe(CN)_6H_2O$, 3.3 mM $K_3Fe(CN)_6$], and the plates are incubated for 30–60 minutes at 37° C.

The X-gal solution is removed and 2 ml of 70% glycerol is added to each dish. Blue stained cells are identified under a light microscope.

This will be used to introduce a MAC, particular the MAC with the anti-HIV megachromome, to produce a mouse model for anti-HIV activity.

EXAMPLE 14

Transgenic Animals

Transgenic animals can be generated that express heterologous genes which confer desired traits, e.g., disease resistance, in the animals. A transgenic mouse is prepared to serve as model of a disease-resistant animal. Genes that encode vaccines or that encode therapeutic molecules can be introduced into embryos or ES cells to produce animals that express the gene product and thereby are resistant to or less susceptible to a particular disorder.

The mammalian artificial megachromosome can be used to generate transgenic animals that stably express genes conferring desired traits, such as genes conferring resistance to pathogenic viruses. Transgenic mice containing a transgene encoding an anti-HIV ribozyme provide a useful model for the development of stable transgenic animals using these methods.

1. Development of Control Transgenic Mice Expressing Anti-HIV Ribozyme

Control transgenic mice are generated in order to compare stability and amounts of transgene expression in mice developed using transgene DNA carried on a vector (control mice) with expression in mice developed using transgenes carried in an artificial megachromosome.

a. Development of Control Transgenic Mice Expressing β-galactosidase

One set of control transgenic mice was generated by microinjection of mouse embryos with the β-galactosidase gene alone. The microinjection procedure used to introduce the plasmid DNA into the mouse embryos is as described in Example 13, but modified for use with embryos [see, e.g., Hogan et al. (1994) *Manipulating the Mouse Embryo, A :Laboratory Manual,* Cold Spring Harbor Laboratory Press, Cold Spring Harbor, N.Y., see, especially pages 255–264 and Appendix 3]. Fertilized mouse embryos [Strain CB6 obtained from Charles River Co.] were injected with 1 ng of plasmid pCH110 (Pharmacia) which had been linearized by digestion with BamHI. This plasmid contains the β-galactosidase gene linked to the SV40 late promoter. The β-galactosidase gene product provides a readily detectable marker for successful transgene expression. Furthermore, these control mice provide confirmation of the microinjection procedure used to introduce the plasmid into the embryos. Additionally, because the megachromosome that is transferred to the mouse embryos in the model system (see below) also contains the β-galactosidase gene, the control transgenic mice that have been generated by injection of pCH110 into embryos serve as an analogous system for comparison of heterologous gene expression from a plasmid versus from a gene carried on an artifical chromosome.

After injection, the embryos are cultured in modified HTF medium under 5% $CO_2$ at 37° C. for one day until they divide to form two cells. The two-cell embryos are then implanted into surrogate mother female mice [for procedures see, *Manipulating the Mouse Embryo, A Laboratory Manual* (1994) Hogan et al., eds., Cold Spring Harbor Laboratory Press, Cold Spring Harbor, N.Y., pp. 127 et seq.].

b. Development of Control Transgenic Mice Expressing Anti-HIV Ribozyme

One set of anti-HIV ribozyme gene-containing control transgenic mice was generated by microinjection of mouse embryos with plasmid pCEPUR-132 which contains three different genes: (1) DNA encoding an anti-HIV ribozyme, (2) the puromycin-resistance gene and (3) the hygromycin-resistance gene. Plasmid pCEPUR-132 was constructed by ligating portions of plasmid pCEP-132 containing the anti-HIV ribozyme gene (referred to as ribozyme D by Chang et al. [(1990) *Clin. Biotech.* 2:23–31]; see also U.S. Pat. No. 5,144,019 to Rossi et al., particularly FIG. 4 of the patent) and the hygromycin-resistance gene with a portion of plasmid pCEPUR containing the puromycin-resistance gene.

Plasmid pCEP-132 was constructed as follows. Vector pCEP4 (Invitrogen, San Diego, Calif.; see also Yates et al. (1985) *Nature* 313:812–815) was digested with XhoI which cleaves in the multiple cloning site region of the vector. This ~10.4-kb vector contains the hygromycin-resistance gene linked to the thymidine kinase gene promoter and polyadenylation signal, as well as the ampicillin-resistance gene and ColE1 origin of replication and EBNA-1 (Epstein-Barr virus nuclear antigen) genes and OriP. The multiple cloning site is flanked by the cytomegalovirus promoter and SV40 polyadenylation signal.

XhoI-digested pCEP4 was ligated with a fragment obtained by digestion of plasmid 132 (see Example 4 for a description of this plasmid) with XhoI and SalI. This XhoI/SalI fragment contains the anti-HIV ribozyme gene linked at the 3' end to the SV40 polyadenylation signal. The plasmid resulting from this ligation was designated pCEP-132. Thus, in effect, pCEP-132 comprises pCEP4 with the anti-HIV ribozyme gene and SV40 polyadenylation signal inserted in the multiple cloning site for CMV promoter-driven expression of the anti-HIV ribozyme gene.

To generate pCEPUR-132, pCEP-132 was ligated with a fragment of pCEPUR. pCEPUR was prepared by ligating a 7.7-kb fragment generated upon NheI/NruI digestion of pCEP4 with a 1.1-kb NheI/SnaBI fragment of pBabe [see Morgenstern and Land (1990) *Nucleic Acids Res.* 18:3587–3596 for a description of pBabe] that contains the puromycin-resistance gene linked at the 5' end to the SV40 promoter. Thus, pCEPUR is made up of the ampicillin-resistance and EBNA1 genes, as well as the ColE1 and OriP elements from pCEP4 and the puromycin-resistance gene from pBabe. The puromycin-resistance gene in pCEPUR is flanked by the SV40 promoter (from pBabe) at the 5' end and the SV40 polyadenylation signal (from pCEP4) at the 3' end.

Plasmid pCEPUR was digested with XhoI and SalI and the fragment containing the puromycin-resistance gene linked at the 5' end to the SV40 promoter was ligated with XhoI-digested pCEP-132 to yield the ~12.1-kb plasmid designated pCEPUR-132. Thus, pCEPUR-132, in effect, comprises pCEP-132 with puromycin-resistance gene and SV40 promoter inserted at the XhoI site. The main elements of pCEPUR-132 are the hygromycin-resistance gene linked to the thymidine kinase promoter and polyadenylation signal, the anti-HIV ribozyme gene linked to the CMV promoter and SV40 polyadenylation signal, and the puromycin-resistance gene linked to the SV40 promtoer and polyadenylation signal. The plasmid also contains the ampicillin-resistance and EBNA1 genes and the ColE1 origin of replication and OriP.

Zygotes were prepared from (C57BL/6JxCBA/J) F1 female mice [see, e.g., *Manipulating the Mouse Embryo, A Laboratory Manual* (1994) Hogan et al., eds., Cold Spring Harbor Laboratory Press, Cold Spring Harbor, N.Y., p. 429], which had been previously mated with a (C57BL/6JxCBA/J) F1 male. The male pronuclei of these F2 zygotes were injected [see, *Manipulating the Mouse Embryo, A Laboratory Manual* (1994)Hogan et al., eds., Cold Spring Harbor Laboratory Press, Cold Spring Harbor, N.Y.] with pCEPUR-132 (~3 μg/ml), which had been linearized by digestion with NruI. The injected eggs were then implanted in surrogate mother female mice for development into transgenic offspring.

These primary carrier offspring were analyzed (as described below) for the presence of the transgene in DNA isolated from tail cells. Seven carrier mice that contained transgenes in their tail cells (but that may not carry the transgene in all their cells, i.e., they may be chimeric) were allowed to mate to produce non-chimeric or germ-line heterozygotes. The heterozygotes were, in turn, crossed to generate homozygote transgenic offspring.

2. Development of Model Transgenic Mice Using Mammalian Artificial Chromosomes

Fertilized mouse embryos are microinjected (as described above) with megachromosomes (1–10 pL containing 0–1 chromosomes/pL) isolated from fusion cell line G3D5* or H1D3* (described above). The megachromosomes are isolated as described herein. Megachromosomes isolated from either cell line carry the anti-HIV ribozyme (ribozyme D) gene as well as the hygromycin-resistance and β-galactosidase genes. The injected embryos are then developed into transgenic mice as described above.

Alternatively, the megachromosome-containing cell line G3D5* or H1D3* is fused with mouse embryonic stem cells [see, e.g., U.S. Pat. No. 5,453,357, commercially available; see *Manipulating the Mouse Embryo, A Laboratory Manual* (1994) Hogan et al., eds., Cold Spring Harbor Laboratory Press, Cold Spring Harbor, N.Y., pages 253–289] following standard procedures see also, e.g., *Guide to Techniques in Mouse Development* in *Methods in Enzymology* Vol. 25, Wassarman and De Pamphilis, eds. (1993), pages 803–932]. (It is also possible to deliver isolated megachromosomes into embryonic stem cells using the Microcell procedure [such as that described above].) The stem cells are cultured in the presence of a fibroblast [e.g., STO fibroblasts that are resistant to hygromycin and puromycin]. Cells of the resultant fusion cell line, which contains megachromosomes carrying the transgenes [i.e., anti-HIV ribozyme, hygromycin-resistance and β-galactosidase genes], are then transplanted into mouse blastocysts, which are in turn implanted into a surrogate mother female mouse where development into a transgenic mouse will occur.

Mice generated by this method are chimeric in that the transgenes will be expressed in only certain areas of the mouse, e.g., the head, and thus may not be expressed in all cells.

3. Analysis of Transgenic Mice for Transgene Expression

Beginning when the transgenic mice, generated as described above, are three-to-four weeks old, they can be analyzed for stable expression of the transgenes that were transferred into the embryos [or fertilized eggs] from which they develop. The transgenic mice may be analyzed in several ways as follows.

a. Analysis of Cells Obtained from the Transgenic Mice

Cell samples [e.g., spleen cells, lymphocytes, tail cells] are obtained from the transgenic mice. Any cells may be tested for transgene expression. If, however, the mice are chimeras generated by microinjection of fertilized eggs with fusions of embryonic stem cells with megachromosome-containing cells, only cells from areas of the mouse that carry the transgene are expected to express the transgene. If the cells survive growth on hygromycin [or hygromycin and puromycin or neomycin, if the cells are obtained from mice generated by transfer of both antibiotic-resistance genes], this is one indication that they are stably expressing the transgenes. RNA isolated from the cells according to standard methods may also be analyzed by northern blot procedures to determine if the cells express transcripts that hybridize to nucleic acid probes based on the antibiotic-resistance genes.

Additionally, cells obtained from the transgenic mice may also be analyzed for β-galactosidase expression using standard assays for this marker enzyme [for example, by direct staining of the product of a reaction involving β-galactosidase and the X-gal substrate, see, e.g., Jones (1986) *EMBO* 5:3133–3142, or by measurement of β-galactosidase activity, see, e.g., Miller (1972) in *Experiments in Molecular Genetics* pp. 352–355, Cold Spring Harbor Press]. Analysis of β-galactosidase expression is particularly used to evaluate transgene expression in cells obtained from control transgenic mice in which the only transgene transferred into the embryo was the β-galactosidase gene.

Stable expression of the anti-HIV ribozyme gene in cells obtained from the transgenic mice may be evaluated in several ways. First, DNA isolated from the cells according to standard procedures may be subjected to nucleic acid amplification using primers corresponding to the ribozyme gene sequence. If the gene is contained within the cells, an amplified product of pre-determined size is detected upon hybridization of the reaction mixture to a nucleic acid probe based on the ribozyme gene sequence. Furthermore, DNA isolated from the cells may be analyzed using Southern blot methods for hybridization to such a nucleic acid probe. Second, RNA isolated from the cells may be subjected to northern blot hybridization to determine if the cells express RNA that hybridizes to nucleic acid probes based on the ribozyme gene. Third, the cells may be analyzed for the presence of anti-HIV ribozyme activity as described, for example, in Chang et al. (1990) *Clin. Biotech.* 2:23–31. In this analysis, RNA isolated from the cells is mixed with radioactively labeled HIV gag target RNA which can be obtained by in vitro transcription of gag gene template under reaction conditions favorable to in vitro cleavage of the gag target, such as those described in Chang et al. (1990) *Clin. Biotech.* 2:23–31. After the reaction has been stopped, the mixture is analyzed by gel electrophoresis to determine if cleavage products smaller in size than the whole template are detected; presence of such cleavage fragments is indicative of the presence of stably expressed ribozyme.

b. Analysis of Whole Transgenic Mice

Whole transgenic mice that have been generated by transfer of the anti-HIV ribozyme gene [as well as selection and marker genes] into embryos or fertilized eggs can additionally be analyzed for transgene expression by challenging the mice with infection with HIV. It is possible for mice to be infected with HIV upon intraperitoneal injection with high-producing HIV-infected U937 cells [see, e.g., Locardi et al. (1992) *J. Virol.* 66:1649–1654]. Successful infection may be confirmed by analysis of DNA isolated from cells, such as peripheral blood mononuclear cells, obtained from transgenic mice that have been injected with HIV-infected human cells. The DNA of infected transgenic mice cells will contain HIV-specific gag and env sequences, as demonstrated by, for example, nucleic acid amplification using HIV-specific primers. If the cells also stably express anti-HIV ribozyme, then analysis of RNA extracts of the cells should reveal the smaller gag fragments arising by cleavage of the qaq transcript by the ribozyme.

Additionally, the transgenic mice carrying the anti-HIV ribozyme gene can be crossed with transgenic mice expressing human CD4 (i.e., the cellular receptor for HIV) [see Gillespie et al. (1993) *Mol. Cell. Biol.* 13:2952–2958; Hanna et al. (1994) *Mol. Cell. Biol.* 14:1084–1094; and Yeung et al. (1994) *J. Exp. Med.* 180:1911–1920, for a description of transgenic mice expressing human CD4]. The offspring of these crossed transgenic mice expressing both the CD4 and anti-HIV ribozyme transgenes should be more resistant to infection [as a result of a reduction in the levels of active HIV in the cells] than mice expressing CD4 alone [without expressing anti-HIV ribozyme].

Since modifications will be apparent to those of skill in this art, it is intended that this invention be limited only by the scope of the appended claims.

What is claimed:

1. A method for producing a transgenic non-human mammal, comprising:
    introducing a cell comprising a satellite artificial chromosome into a female non-human mammal, wherein the cell develops into an embryo in a female non-human mammal; and
    allowing the embryo to develop into a transgenic non-human mammal comprising a satellite artificial chromosome.

2. The method of claim 1, wherein the satellite artificial chromosome comprises heterologous DNA that encodes a therapeutic product.

3. The method of claim 1, wherein the cell contains the satellite artificial chromosome in a pronucleus.

4. The method of claim 1, wherein the cell is a zygote.

5. The method of claim 1, wherein the cell is a fertilized ovum.

6. The method of claim 1, wherein the satellite artificial chromosome is a megachromosome derived from a cell line having all of the identifying characteristics of the cell line deposited under ECACC accession number 96040928 or 96040929.

7. The method of claim 1, wherein the cell is a mouse cell.

8. The method of claim 1, wherein the cell is an ovum that develops into an embryo or zygote.

9. The method of claim 1, wherein the embryo and the female non-human mammal are of the same species.

10. A method of producing a trransgenic embryo, comprising:
    introducing a satellite artificial chromosome into a cell, wherein the cell develops in culture into an embryo; and
    culturing the cell under conditions whereby it develops into an embryo.

11. The method of claim 10, wherein the cell comprises a fertilized oocyte, an ovum, a fertilized ovum or a zygote.

12. The method of claim 10, wherein the cell is a mouse embryonic stem cell.

13. A method for producing a transgenic non-human mammal, comprising:
    introducing an embryo comprising a satellite artificial chromosome into a female non-human mammal; and
    allowing the embryo to develop into a transgenic non-human mammal comprising a satellite artificial chromosome.

14. The method of claim 13, wherein the embryo is produced by introducing a SATAC into a cell that develops into an embryo, wherein introduction is effected by a method selected from the group consisting of direct uptake, incubation with polyethylene glycol (PEG), lipofection, microinjection, cell fusion, microcell fusion, electroporation, electrofusion, particle bombardment, projectile bombardment, calcium phosphate precipitation and site-specific targeting.

15. The method of claim 14, wherein the cell is selected from the group consisting of an ovum, a zygote, a mouse embryonic stem cell and a fertilized oocyte.

16. The method of claim 13, wherein the embryo and the female non-human mammal are of the same species.

17. A method for producing a transgenic non-human mammal, comprising:
    introducing a fertilized oocyte comprising a satellite artificial chromosome into a female non-human mammal; and
    allowing the resulting embryo to develop into a transgenic non-human mammal comprising a satellite artificial chromosome.

18. A method for producing a transgenic mouse, comprising:
    introducing a mouse embryonic stem cell comprising a satellite artificial chromosome into an embryo;
    introducing the embryo into a female mouse; and
    allowing the embryo to develop into a transgenic mouse comprising a satellite artificial chromosome.

19. A method for producing a transgenic non-human mammal, comprising:
    introducing an ovum comprising a satellite artificial chromosome (SATAC) into a female non-human mammal, wherein the ovum develops into a zygote or embryo; and
    allowing the embryo or zygote to develop into a transgenic non-human animal comprising the SATAC.

20. The method of claim 19, wherein the satellite artificial chromosome is a megachromosome derived from a cell line having all of the identifying characteristics of the cell line deposited under ECACC accession number 96040928 or 96040929.

\* \* \* \* \*

UNITED STATES PATENT AND TRADEMARK OFFICE
CERTIFICATE OF CORRECTION

PATENT NO.     : 6,743,967 B2
DATED          : June 1, 2004
INVENTOR(S)    : Gyula Hadlaczy and Aladar Szalay It is certified that error appears in the above-identified patent and that said Letters Patent is hereby corrected as shown below:

Title page,
Item [57], ABSTRACT,
Line 62, replace "heteroaromatic" with -- heterochromatin --;

Column 3,
Line 6, replace "germane" with -- germline --;

Column 7,
Lines 25, 28, 29, 50 and 53, replace "heteroaromatic" with -- heterochromatin --;

Column 17,
Line 16, replace "ctivated" with -- activated --;

Column 29,
Line 49, replace "SaII" with -- SalI --;
Line 64, replace "Bg111" with -- Bg1II --;

Column 30,
Line 2, replace "BgIII" with -- BglII --;

Column 36,
Line 57, replace "table" with -- stable --;

Column 37,
Line 60 replace "$\mu$g/mI" with -- $\mu$g/ml --;

Column 46,
Line 58, replace "SaII" with -- SalI --;
Line 58, replace "SalI" with -- SalI --;

Column 47,
Line 11, replace "BgIII" with BglII --;
Line 60, replace "Inucleotide 232-10044 of SEQ ID No.2]" with -- [nucleotide 232-10044 of SEQ ID No.2] --;

Column 49,
Line 42, replace "moleculeencoding" with -- molecule-encoding --;
Lines 50 and 67, replace "SaII" with -- SalI --;

UNITED STATES PATENT AND TRADEMARK OFFICE
CERTIFICATE OF CORRECTION

PATENT NO. : 6,743,967 B2
DATED : June 1, 2004
INVENTOR(S) : Gyula Hadlaczy and Aladar Szalay It is certified that error appears in the above-identified patent and that said Letters Patent is hereby corrected as shown below:

Column 50,
Lines 19 and 34, replace "SaII" with -- SalI --;

Column 51,
Lines 19, 27, 37, 38, 54 and 55, replace "SaII" with -- SalI --;

Column 58,
Lines 44, 45 and 65, replace "SaII" with -- SalI --;

Column 61,
Line 16, replace "qaq" with -- gag --;

Column 75,
Line 41, Claim 10 should read as follows:
    10. A method of producing a transgenic non-human embryo, comprising:

introducing a satellite artificial chromosome into a cell, wherein the cell develops in culture into an non-human embryo; and culturing the cell under conditions whereby it develops into an embryo.

Signed and Sealed this

Seventh Day of December, 2004

JON W. DUDAS
*Director of the United States Patent and Trademark Office*